United States Patent [19]
Calenoff

[11] Patent Number: 6,025,477
[45] Date of Patent: Feb. 15, 2000

[54] ATHEROSCLEROTIC PLAQUE SPECIFIC ANTIGENS, ANTIBODIES THERETO, AND USES THEREOF

[76] Inventor: Emanuel Calenoff, 750 N. Rush St., Apt. 3402, Chicago, Ill. 60611

[21] Appl. No.: 08/386,221

[22] Filed: Feb. 9, 1995

Related U.S. Application Data

[63] Continuation of application No. 07/828,860, Jan. 31, 1992, abandoned, which is a continuation-in-part of application No. 07/388,129, Jul. 31, 1989, abandoned, which is a continuation-in-part of application No. 07/067,995, Jun. 29, 1987, abandoned, which is a continuation-in-part of application No. 07/067,993, Jun. 29, 1987, abandoned, which is a continuation-in-part of application No. 07/067,986, Jun. 29, 1987, abandoned, which is a continuation-in-part of application No. 06/876,741, Jun. 20, 1986, abandoned, which is a continuation-in-part of application No. 06/871,811, Jun. 6, 1986, abandoned, which is a continuation-in-part of application No. 06/846,401, Mar. 31, 1986, abandoned.

[30] Foreign Application Priority Data

Jul. 31, 1990 [WO] WIPO ............... PCT/US90/04272

[51] Int. Cl.[7] ............ C07K 16/18; C07K 17/00; C12N 5/18
[52] U.S. Cl. ............ 530/388.2; 530/387.3; 530/391.1; 435/332
[58] Field of Search ............ 435/7.2, 7.9, 240.27, 435/960, 968, 972; 530/388.2, 389.5, 391.1, 391.3, 387.3; 436/518, 548, 800, 804, 811; 424/1.49

[56] References Cited

U.S. PATENT DOCUMENTS

| | | | |
|---|---|---|---|
| 4,343,734 | 8/1982 | Lian et al. | 530/389.1 |
| 4,628,027 | 12/1986 | Gay | 436/548 |
| 4,816,567 | 3/1989 | Cabilly et al. | 530/387.3 |
| 5,026,537 | 6/1991 | Daddona et al. | 424/1.1 |
| 5,110,738 | 5/1992 | Takano et al. | 435/240.27 |
| 5,196,324 | 3/1993 | Bumol et al. | 435/70.21 |

FOREIGN PATENT DOCUMENTS

| | | |
|---|---|---|
| 0267690 | 5/1988 | European Pat. Off. . |

OTHER PUBLICATIONS

Curtiss, L.K. and Witztum, J.L., A Novel Method for Generating Region—Specific Monoclonal Antibodies To Modified Proteins. The Journal Of Clinical Investigation. (Oct. 1983) 72:4 1427–1438.

Haberland, M.E., et al. Malondialdehyde–Altered Protein Occurs In Atheroma Of Watanabe Heritable Hyperlipidemic Rabbits. Science (Jul. 8, 1988) 241: 215–218.

Kimura, J., et al., Monoclonal Antibodies Recognizing Lipid–Laden Cells And Extracellular Regions With Lipid–Deposits In Atherosclerotic Aorta. Virchows Arch. (1986) 410(2): 159–164.

Shih, I.L., et al., Focal Accumulation of An Apolipoprotein B– Based Synthetic Oligopeptide In The Healing Rabbit Arterial Wall. Proc. Nat'l. Acad. Sci. (Feb. 1990) 87: 1436–1440.

*Primary Examiner*—Marian C. Knode
*Assistant Examiner*—Donna C. Wortman
*Attorney, Agent, or Firm*—Albert P. Halluin; Pennie & Edmonds LLP

[57] ABSTRACT

This invention provides purified antigens which are indicative of the presence of atherosclerotic plaque. Different concentrations of these antigens have been found to coincide with the progression of atherosclerosis. The subject invention also provides different hybridoma cell lines which produce monoclonal antibodies directed to antigens associated with atherosclerosis and a hybridoma cell line which produces monoclonal antibodies directed to antigen associated with normal artery and not with plaque. The atherosclerotic plaque antigen, and monoclonal antibodies made thereto, are used in various methods for detecting in a biological sample an antigen present in, and indicative of the presence of, atherosclerotic plaque. The monoclonal antibodies are also used in methods of imaging atherosclerotic plaque, and treating atherosclerosis. The methods of treating atherosclerosis include a method of digesting atherosclerotic plaque with enzymes, and a method of ablating atherosclerotic plaque using radiation. The subject invention also provides a method of treating atherosclerotic plaque by directly delivering a drug to the plaque. The subject invention further provides a method for treating atherosclerosis by blocking the synthesis of atherosclerotic plaque or by blocking binding of antibodies to the antigen.

7 Claims, 55 Drawing Sheets

NON-SPECIFIC IgM MAb

FIG. 17A

```
                       10v           20v              30v                40v                50v
VH1BACK(1,22)     AGGTSMARCTGCAGSAGTCWGG
Z2VH1(1,220)'                          CTGCAGGAGTCWGGAGGAGGCTTGGTGCAACCTGGGGGGTCA
Z2VH12(1,218)'                         CTGCAGGAGTCWGGAGGAGGCTTGGTGCAACCTGGGGGGTCA
Z2VH7(1,220)'                          CTGCAGGAGTCWGGAGGAGGCTTGGTGCAACCTGGGGGGTCA
Z2VH9(1,218)'                          CTGCAGGAGTCTGGAGGAGGCTTGGTGCAACCTGGGGGGTCG
Z2VH20A(1,237)                         CTGCAGGAGTCAGGAGGAGGCTTGGTGCAACCTGGGGGGTCA
Z2VH2(1,220)                           CTGCAGGAGTCAGGAGGAGGCTTGGTGCAACCTGGGGGGTCA
Z2VH5(1,220)                                       AGGCTTGGTGCAACCTGGGGGGTCA
Z2VH6(1,220)                                       AGGCTTGGTGCAACCTGGGGGGTCA
Z2VH8(1,219)                                       AGGCTTGGTGCAACCTGGGGGGTCA
Z2VH10(1,218)                                       GGCTTGGTGCAACCTGGGGGGTCA
                                                    GCTTGGTGCAACCTGGGGGGTCA consensus         AGGTSMARCTGCAGGAGTCWGGAGGAGGCTTGGTGCAACCTGGGGGGTCA
```

FIG. 17B

```
                       60v           70v           80v           90v          100v
Z2VH1(1,220)'   CGGGGACTCTCTTGTGAAGGCTCAGGGTTTACTTTTAGTGGCTTCTGGAT
Z2VH12(1,218)'  CGGGGACTCTCTTGTGAAGGCTCAGGGTTTACTTTTAGTGGCTTCTGGAT
Z2VH7(1,220)'   CGGGGACTCTCTTGTGAAGGCTCAGGGCTTACTTTTAGTGGCTTCTGGAT
Z2VH9(1,218)'   CGGGGACTCTCTTGTGAAGGCTCAGGGTTTACTTTTAGTGGCTTCTGGAT
Z2VH20A(1,237)  CGGGGACTCTCTTGTGAAGGCTCAGGGTTTACTTTTAGTGGCTTCTGGAT
Z2VH2(1,220)    CGGGGACTCTCTTGTGAAGGCTCAGGGTTTACTTTTAGTGGCTTCTGGAT
Z2VH5(1,220)    CGGGGACTCTCTTGTGAAGGCTCAGGGTTTACTTTTAGTGGCTTCTGGAT
Z2VH6(1,220)    CGGGGACTCTCTTGTGAAGGCTCAGGGTTTACTTTTAGTGGCTTCTGGAT
Z2VH8(1,219)    CGGGGACTCTCTTGTGAAGGCTCAGGGTTTACTTTTAGTGGCTTCTGGAT
Z2VH10(1,218)   CGGGGACTCTCTTGTGAAGGCTCAGGGTTTACTTTTAGTGGCTTCTGGAT consensus       CGGGGACTCTCTTGTGAAGGCTCAGGGTTTACTTTTAGTGGCTTCTGGAT
```

FIG. 17C

```
                             110v          120v          130v          140v          150v
Z2VH1(1,220)'    GAGCTGGGTTCGACAGAGACACCTGGGAAGACCCTGGAGTGGATTGGAGACA
Z2VH12(1,218)'   GAGCTGGGTTCGACAGAGACACCTGGGAAGACCCTGGAGTGGATTGGAGACA
Z2VH7(1,220)'    GAGCTGGGTTCGACAGAGACACCTGGGAAGACCCTGGAGTGGATTGGAGACA
Z2VH9(1,218)'    GAGCTGGGTTCGACAGAGACACCTGGGAAGACCCTGGAGTGGATTGGAGACA
Z2VH20A(1,237)   GAGCTGGGTTCGACAGAGACACCTGGGAAGACCCTGGAGTGGATTGGAGACA
Z2VH2(1,220)     GAGCTGGGTTCGACAGAGACACCTGGGAAGACCCTGGAGTGGATTGGAGACA
Z2VH5(1,220)     GAGCTGGGTTCGACAGAGACACCTGGGAAGACCCTGGAGTGGATTGGAGACA
Z2VH6(1,220)     GAGCTGGGTTCGACAGAGACACCTGGGAAGACCCTGGAGTGGATTGGAGACA
Z2VH8(1,219)     GAGCTGGGTTCGACAGAGACACCTGGGAAGACCCTGGAGTGGATTGGAGACA
Z2VH10(1,218)    GAGCTGGGTTCGACAGAGACACCTGGGAAGACCCTGGAGTGGATTGGAGACA consensus        GAGCTGGGTTCGACAGAGACACCTGGGAAGACCCTGGAGTGGATTGGAGACA
```

FIG. 17D

```
                  160v           170v           180v           190v           200v
Z2VH1(1,220)'    TTAATTCTGATGGCAGTGCAATAAACTACGCACCATCCATAAAGGATCGA
Z2VH12(1,218)'   TTAATTCTGATGGCAGTGCAATAAACTACGCACCATCCATAAAGGATCGA
Z2VH7(1,220)'    TTAATTCTGATGGCAGTGCAATAAACTACGCACCATCCATAAAGGATCGA
Z2VH9(1,218)'    TTAATTCTGATGGCAGTGCAATAAACTACGCACCATCCATAAAGGATCGA
Z2VH20A(1,237)   CTAATTCTGATGGCAGTGCAATAAACTACGCACCATCCATAAAGGATCGA
Z2VH2(1,220)     TTAATTCTGATGGCAGTGCAATAAACTACGCACCATCCATAAAGGATCGA
Z2VH5(1,220)     TTAATTCTGATGGCAGTGCAATAAACTACGCACCATCCATAAAGGATCGA
Z2VH6(1,220)     TTAATTCTGATGGCAGTGCAATAAACTACGCACCATCCATAAAGGATCGA
Z2VH8(1,219)     TTAATTCTGATGGCAGTGCAATAAACTACGCACCATCCATAAAGGATCGA
Z2VH10(1,218)    TTAATTCTGATGGCAGTGCAATAAACTACGCACCATCCATAAAGGATCGA

TTAATTCTGATGGCAGTGCAATAAACTACGCACCATCCATAAAGGATCGA  consensus
```

ZZVH1(1,220)'   TTCACTATCTTCAGAGACAATGACAAGA
ZZVH12(1,218)'  TTCACTATCTTCAGAGACAATGACAA
ZZVH7(1,220)'   TTCACTATCTTCAGAGACAATGACAAGA
ZZVH9(1,218)'   TTCACTATCTTCAGAGACAATGACAA
ZZVH20A(1,237)  TTCACTATCTTCAGAGACAATGACAAGAGCACCCTGTACCTGCAG
ZZVH2(1,220)    TTCACTATCTTCAGAGACAATGACAAGAGCACCCTGTACCTGCAG
ZZVH5(1,220)    TTCACTATCTTCAGAGACAATGACAAGAGCACCCTGTACCTGCAG
ZZVH6(1,220)    TTCACTATCTTCAGAGACAATGACAAGAGCACCCTGTACCTGCAG
ZZVH8(1,219)    TTCACTATCTTCAGAGACAATGACAAGAGCACCCTGTACCTGCAG
ZZVH10(1,218)   TTCACTATCTTCAGAGACAATGACAAGAGCACCCTGTACCTGCAG
ZZVH21(1,147)   TTCACTATCTTCAGAGACAATGACAAGAGCACCCTGTACCTGCAG  CTGCAGATGAG
ZZVH17(1,114)'                                          CTGCAGATGAG concensus       TTCACTATCTTCAGAGACAATGACAAGAGCACCCTGTACCTGCAGATGAG
```

```
                        260v       270v       280v       290v       300v
ZZVH21(1,147)    CAATGTGCGATCTGAGGACACAGCCACGTATTTCTGTATGAGATATGATG
ZZVH17(1,114)'   CAATGTGCGATCTGAGGACACAGCCACGTATTTCTGTATGAGATATGATG consensus        CAATGTGCGATCTGAGGACACAGCCACGTATTTCTGTATGAGATATGATG 310v       320v       330v       340v       350v
ZZVH21(1,147)    GTTACTACTGGTACTTCGATGTCTGGGGCGCAGGGACCACGGTCACCGTC
ZZVH17(1,114)'   GTTACTACTGGTACTTCGATGTCTGGGGCGCAGGGACCACGGTCACCGTC consensus        GTTACTACTGGTACTTCGATGTCTGGGGCGCAGGGACCACGGTCACCGTC 360v       370v       380v       390v       400v
ZZVH21(1,147)    TCCTCAGAGAGTCAGTCCTTCCCAA--GTCTTAAGCTT
ZZVH17(1,114)'   TCC
CM1FOR(1,34)'            GAGAGTCAGTCCTTCCCAAATGTCTTAAGCTTCC consensus        TCCTCAGAGAGTCAGTCCTTCCCAAatGTCTTAAGCTTCC
```

```
                    P    M   P     M    HF
            PMH M   L    A   L     A    NI
            SNN N   E    E   E     E    FN
            TLF L   1    3   1     1    11
            111 1   ///
AGGTSMARCTGCAGGAGTCWGGAGGAGGCTTGGTGCAACCTGGGGGGTCACGGGGACTCT
---+---------+---------+---------+---------+---------+
TCCASKTYGACGTCCTCAGWCCTCCTCCGAACCACGTTGGACCCCCAGTGCCCCTGAGA
                                                    60 v k/q l   q  e  s  g  g  g  l  v  q  p  g  g  s  r  g  l  s
```

FIG. 18B

```
        D              A                  FT         ESBB
        D              L                  OA         CESS
        E              U                  KQ         RCAA
        1              1                  11         21JJ
                                           /          //
                                                              120
CTTGTGAAAGGCTCAGGGTTTACTTTTTAGTGGCTTCTGGATGAGCTGGGTTCGACAGACAC
----+----+----+----+----+----+----+----+----+----+----+----+
GAACACTTTCCGAGTCCCAAATGAAAAATCACCGAAGACCTACTCGACCCAAGCTGTCTGTG c  e  g  s  g  f  t  f  s  g  f  w  m  s  w  v  r  q  t  p
----+----+----+----+----+----+----+----+----+----+----+----+
```

FIG. 18C

```
AS B           B           AM                F
PC B          BSEBBEASMA   SS                O
YR V          SECBSCPCBL   EE                K
11 2          ACPSARYROW   11                1
              J111J21122
              ////                                            180
         CTGGGAAGACCCTGGAGTTGGATTGGAGACATTAATTCTGATGGCAGTGCAATAAAACTACG
         ---------+---------+---------+---------+---------+---------+
         GACCCTTCTGGGACCTCACCTAACCTCTGTAATTAAGACTACCGTCACGTTATTTGATGC g  k  t  l  e  w  i  g  d  i  n  s  d  g  s  a  i  n  y  a
```

FIG. 18D

```
               A    B        HN   R
BMDDCTTHM      L    S        GS   S
IBPPLAFNB      W    M        IP   A
NONNAQIFO      2    2        A2   1
112111112                                                    240
  /   //                       /
        CACCATCCATAAAGGATCGATTCCACTATCTTCAGAGACAATGACAAGAGCACCCTGTACC
        ----.----+----.----+----.----+----.----+----.----+----.----+
        GTGGTAGGTATTTCCTAGCTAAGTGATAGAAGTCTCTGTTACTGTTCTCGTGGGACATGG p  s  i  k  d  r  f  t  i  f  r  d  n  d  k  s  t  l  y  l
```

FIG. 18E

```
P B           M MDD D              M              M
S S           N BPP D              A              A
T P           L ONN E              E              E
1 1           1 121 1              2              3
              /
TGCAGATGAGCAATGTGCGATCTGAGGACACAGCCACGTATTTCTGTATGAGATATGATG
----+----.----+----.----+----.----+----.----+----.----+----
ACGTCTACTCGTTACACGCTAGACTCCTGTGTCGGTGCATAAAGACATACTCTATACTAC
                                                    300
 q m s n v r s e d t a t y f c m r y d g
```

FIG. 18F

```
                                                    →CH1
        R  T       H H    ANAFDDSBBBMH    BD    AH
        S  A       I H    VLSISSESSSAP    SD    LN
        A  Q       N A    AAUNAACAATEH    ME    WF
        1  1       P 1    241111JJE31     21    21
                          / ///////        /
                                                      360
GTTACTACTGGTACTTCGATGTCTGGGGGCGCAGGGACCACGGTCACCGTCTCCTCAGAGA
----+----+----+----+----+----+----+----+----+----+----+----+
CAATGATGACCATGAAGCTACAGACCCCCGCGTCCCTGGTGCCAGTGGCAGAGGAGTCTCT y  y  w  y  f  d  v  w  g  a  g  t  t  v  t  v  s  s  e  s
```

FIG. 18G

```
                          A M H A
         M P              F S I L
M   P    L E              L E N U
N   L    E 1              2 1 3 1
L   1    1
         GTCAGTCCTTCCCAAATGTCTCTTAAGCTTCC
         ----:----+----:----.----:----+----   390
         CAGTCAGGAAGGGTTTACAGAATTCGAAGG q  s  f  p  n  v
         ----:----+----:----.----:----+
```

FIG. 19

```
              10v              20v              30v              40v          50v
ZZD3MUVH  XVXLQESGGGLVQPGGSRGLSCEGSGFTFS GFWMS WVRQTPGKTLEWIG DI
              V L ESGGGLVQPGGS  LSC  SGF FS   WMS  WVRQ PGK LEWIG  I
MUVHIIIB  EVKLLESGGGLVQPGGSLKLSCAASGFDFS RYWMS WVRQAPGKGLEWIG EI 60v              70v              80v              90v         100v
ZZD3MUVH  N--SDGSAINYAPSIKD RFTIFRDNDKSTLYLQMSNVRSEDTATYFCMR YD
              D S INY PS KD   F I RDN K TLYLQMS VRSEDTA Y C R
MUVHIIIB  NPKADSSTINYTPSLKD KFIISRDNAKNTLYLQMSKVRSEDTALYYCAR L-

110v
ZZD3MUVH  GYYWYFDV WGAGTTVTVSS
          GYY YF   WG GTTVTVSS
MUVHIIIB  GYYGYFAY WGQGTTVTVSS
```

FIG. 20A

```
                    10v       20v       30v       40v       50v
VK1BACK(1,24)    GACATTCAGCTGACCCAGTCTCCA
Z2VK34(1,291)            CTGACCCAGTCTCTCCATCCTCCATGTATGCATCGCTGGGAGA
Z2VK10(1,140)            CTGACCCAGTCTCTCCATCCTCCATGTATGCATCGCTGGGAGA
Z2VK17(1,92)             CTGACCCAGTCTCTCCATCCTCCATGTATGCATCGCTGGGAGA
Z2VK23(1,152)            CTGACCCAGTCTCTCCATCCTCCATGTATGCATCGCTGGGAGA
Z2VK3(1,141)                     CTCCATCCTCCATGTATGCATCGCTGGGAGA
Z2VK11A(1,84)                     TCCATCCTCCATGTATGCATCGCTGGGAGA
Z2VK7(1,140)                      TCCATCCTCCATGTATGCATCGCTGGGAGA
Z2VK8A(1,140)                     TCCATCCTCCATGTATGCATCGCTGGGAGA
Z2VK28(1,265)                              TGCATCGCTGGGAGA
Z2VK29(1,265)                              TGCATCGCTGGGAGA
Z2VK30(1,265)                              TGCATCGCTGGGAGA
Z2VK31(1,264)                               GCATCGCTGGGAGA
Z2VK32(1,264)                               GCATCGCTGGGAGA
Z2VK36(1,263)'                               CATCGCTGGGAGA
Z2VK25(1,260)'                                 CGCTGGGAGA consensus        GACATTCAGCTGACCCAGTCTCTCCATCCTCCATGTATGCATCGCTGGGAGA
```

FIG. 20B

```
                              60v           70v           80v           90v           100v
Z2VK34(1,291)'    GAGAGTCACTATCACTTGCAAGGCGAGTCAGGACATTAAAAGCTATTTAA
Z2VK10(1,140)'    GAGAGTCACTATCACTTGCAAGGCGAGTCAGGACATTAAAAGCTATTTAA
Z2VK17(1,92)'     GAGAGTCACTATCACTTGCAAGGCGAGTCAGGACATTAAAAGCTATTTAA
Z2VK23(1,152)     GAGAGTCACTATCACTTGCAAGGCGAGTCAGGACATTAAAAGCTATTTAA
Z2VK3(1,141)      GAGAGTCACTATCACTTGCAAGGCGAGTCAGGACATTAAAAGCTATTTAA
Z2VK11A(1,84)     GAGAGTCACTATCACTTGCAAGGCGAGTCAGGACATTAAAAGCTATTTAA
Z2VK7(1,140)      GAGAGTCACTATCACTTGCAAGGCGAGTCAGGACATTAAAAGCTATTTAA
Z2VK8A(1,140)     GAGAGTCACTATCACTTGCAAGGCGAGTCAGGACATTAAAAGCTATTTAA
Z2VK28(1,265)     GAGAGTCACTATCACTTGCAAGGCGAGTCAGGACATTAAAAGCTATTTAA
Z2VK29(1,265)     GAGAGTCACTATCACTTGCAAGGCGAGTCAGGACATTAAAAGCTATTTAA
Z2VK30(1,265)     GAGAGTCACTATCACTTGCAAGGCGAGTCAGGACATTAAAAGCTATTTAA
Z2VK31(1,264)     GAGAGTCACTATCACTTGCAAGGCGAGTCAGGACATTAAAAGCTATTTAA
Z2VK32(1,264)     GAGAGTCACTATCACTTGCAAGGCGAGTCAGGACATTAAAAGCTATTTAA
Z2VK36(1,263)'    GAGAGTCACTATCACTTGCAAGGCGAGTCAGGACATTAAAAGCTATTTAA
Z2VK25(1,260)'    GAGAGTCACTATCACTTGCAAGGCGAGTCAGGACATTAAAAGCTATTTAA
Z2VK18B(1,88)'                    AAGGCGAGTCAGGACATTAAAAGCTATTTAA consensus         GAGAGTCACTATCACTTGCAAGGCGAGTCAGGACATTAAAAGCTATTTAA
```

FIG. 20C

```
                        110v          120v          130v          140v          150v
Z2VK34(1,291)'   GCTGGTACCAGCAGAAACCATGGAAATCTCCTAAGACCCTGATCTATTAT
Z2VK10(1,140)'   GCTGGTACCAGCAGAAACCATGGAAATCTCCTAAGACCCTGATCTATTA
Z2VK17(1,92)'    G
Z2VK23(1,152)    GCTGGTACCAGCAGAAACCATGGAAATCTCCTAAGACCCTGATCTATTAT
Z2VK3(1,141)     GCTGGTACCAGCAGAAACCATGGAAATCTCCTAAGACCCTGATCTATTAT
Z2VK11A(1,84)    GCTG
Z2VK7(1,140)     GCTGGTACCAGCAGAAACCATGGAAATCTCCTAAGACCCTGATCTATTAT
Z2VK8A(1,140)    GCTGGTACCAGCAGAAACCATGGAAATCTCCTAAGACCCTGATCTATTAT
Z2VK28(1,265)    GCTGGTACCAGCAGAAACCATGGAAATCTCCTAAGACCCTGATCTATTAT
Z2VK29(1,265)    GCTGGTACCAGCAGAAACCATGGAAATCTCCTAAGACCCTGATCTATTAT
Z2VK30(1,265)    GCTGGTACCAGCAGAAACCATGGAAATCTCCTAAGACCCTGATCTATTAT
Z2VK31(1,264)    GCTGGTACCAGCAGAAACCATGGAAATCTCCTAAGACCCTGATCTATTAT
Z2VK32(1,264)    GCTGGTACCAGCAGAAACCATGGAAATCTCCTAAGACCCTGATCTATTAT
Z2VK36(1,263)'   GCTGGTACCAGCAGAAACCATGGAAATCTCCTAAGACCCTGATCTATTAT
Z2VK25(1,260)'   GCTGGTACCAGCAGAAACCATGGAAATCTCCTAAGACCCTGATCTATTAT
Z2VK18B(1,88)'   GCTGGTACCAGCAGAAACCATGGAAATCTCCTAAGACCCTGATCTATTAT consensus        GCTGGTACCAGCAGAAACCATGGAAATCTCCTAAGACCCTGATCTATTAT
```

FIG. 20D

```
              160v          170v          180v          190v         200v
Z2VK34(1,291)' GCAACAAGCTTGGCAGATGGGGTCCCATCAAGATTCAGTGGCAGTGGATC
Z2VK23(1,152)  GCAACAAGCTT
Z2VK3(1,141)   GCAACAAGCT
Z2VK7(1,140)   GCAACAAGCT
Z2VK8A(1,140)  GCAACAAGCT
Z2VK28(1,265)  GCAACAAGCTTGGCAGATGGGGTCCCATCAAGATTCAGTGGCAGTGGATC
Z2VK29(1,265)  GCAACAAGCTTGGCAGATGGGGTCCCATCAAGATTCAGTGGCAGTGGATC
Z2VK30(1,265)  GCAACAAGCTTGGCAGATGGGGTCCCATCAAGATTCAGTGGCAGTGGATC
Z2VK31(1,264)  GCAACAAGCTTGGCAGATGGGGTCCCATCAAGATTCAGTGGCAGTGGATC
Z2VK32(1,264)  GCAACAAGCTTGGCAGATGGGGTCCCATCAAGATTCAGTGGCAGTGGATC
Z2VK36(1,263)' GCAACAAGCTTGGCAGATGGGGTCCCATCAAGATTCAGTGGCAGTGGATC
Z2VK25(1,260)' GCAACAAGCTTGGCAGATGGGGTCCCATCAAGATTCAGTGGCAGTGGATC
Z2VK18B(1,88)' GCAACAA
Z2VK19(1,203)          AGCTTGGCAGATGGGGTCCCATCAAGATTCAGTGGCAGTGGATC
Z2VK20(1,204)          AGCTTGGCAGATGGGGTCCCATCAAGATTCAGTGGCAGTGGATC
Z2VK16(1,175)         AGCTTGGCAGATGGGGTCCCATCAAGATTCAGTGGCAGTGGATC
Z2VK18A(1,167)'         CTTGGCAGATGGGGTCCCATCAAGATTCAGTGGCAGTGGATC consensus      GCAACAAGCTTGGCAGATGGGGTCCCATCAAGATTCAGTGGCAGTGGATC
```

FIG. 20E

```
                          210v         220v         230v         240v         250v
Z2VK34(1,291)'   TGGGCAAGATTATTCTCTAACCATCAGCAGCAGCCTGGAGTCTGACGATACAG
Z2VK28(1,265)    TGGGCAAGATTATTCTCTAACCATCAGCAGCAGCCTGGAGTCTGACGATACAG
Z2VK29(1,265)    TGGGCAAGATTATTCTCTAACCATCAGCAGCAGCCTGGAGTCTGACGATACAG
Z2VK30(1,265)    TGGGCAAGATTATTCTCTAACCATCAGCAGCAGCCTGGAGTCTGACGATACAG
Z2VK31(1,264)    TGGGCAAGATTATTCTCTAACCATCAGCAGCAGCCTGGAGTCTGACGATACAG
Z2VK32(1,264)    TGGGCAAGATTATTCTCTAACCATCAGCAGCAGCCTGGAGTCTGACGATACAG
Z2VK36(1,263)'   TGGGCAAGATTATTCTCTAACCATCAGCAGCAGCCTGGAGTCTGACGATACAG
Z2VK25(1,260)'   TGGGCAAGATTATTCTCTAACCATCAGCAGCAGCCTGGAGTCTGACGATACAG
Z2VK19(1,203)    TGGGCAAGATTATTCTCTAACCATCAGCAGCAGCCTGGAGTCTGACGATACAG
Z2VK20(1,204)    TGGGCAAGATTATTCTCTAACCATCAGCAGCAGCCTGGAGTCTGACGATACAG
Z2VK16(1,175)'   TGGGCAAGATTATTCTCTAACCATCAGCAGCAGCCTGGAGTCTGACGATACAG
Z2VK18A(1,167)'  TGGGCAAGATTATTCTCTAACCATCAGCAGCAGCCTGGAGTCTGACGATACAG
Z2VK8B(1,154)       AAGATTATTCTCTAACCATCAGCAGCAGCCTGGAGTCTGACGATACAG consensus        TGGGCAAGATTATTCTCTAACCATCAGCAGCAGCCTGGAGTCTGACGATACAG
```

FIG. 20F

| | 260v | 270v | 280v | 290v | 300v |
|---|---|---|---|---|---|
| Z2VK34(1,291)' | CAACTTATTACTGTCTACAGCATGGTGAGAGCCCGCTCACGTTCGGTGCT |
| Z2VK28(1,265) | CAACTTATTACTGTCTACAGCATGGTGAGAGCCCGCTCACGTTCGGTGCT |
| Z2VK29(1,265) | CAACTTATTACTGTCTACAGCATGGTGAGAGCCCGCTCACGTTCGGTGCT |
| Z2VK30(1,265) | CAACTTATTACTGTCTACAGCATGGTGAGAGCCCGCTCACGTTCGGTGCT |
| Z2VK31(1,264) | CAACTTATTACTGTCTACAGCATGGTGAGAGCCCGCTCACGTTCGGTGCT |
| Z2VK32(1,264) | CAACTTATTACTGTCTACAGCATGGTGAGAGCCCGCTCACGTTCGGTGCT |
| Z2VK36(1,263)' | CAACTTATTACTGTCTACAGCATGGTGAGAGCCCGCTCACGTTCGGTGCT |
| Z2VK25(1,260)' | CAACTTATTACTGTCTACAGCATGGTGAGAGCCCGCTCACGTTCGGTGCT |
| Z2VK19(1,203) | CAACTTATTACTGTCTACAGCATGGTGAGAGCCCGCTCACGTTCGGTGCT |
| Z2VK20(1,204) | CAACTTATTACTGTCTACAGCATGGTGAGAGCCCGCTCACGTTCGGTGCT |
| Z2VK16(1,175)' | CAACTTATTACTGTCTACAGCATGGTGAGAGCCCGCTCACGTTCGGTGCT |
| Z2VK18A(1,167)' | CAACTTATTACTGTCTACAGCATGGTGAGAGCCCGCTCACGTTCGGTGCT |
| Z2VK8B(1,154) | CAACTTATTACTGTCTACAGCATGGTGAGAGCCCGCTCACGTTCGGTGCT |
| consensus | CAACTTATTACTGTCTACAGCATGGTGAGAGCCCGCTCACGTTCGGTGCT |

FIG. 20G

```
                        310v       320v       330v       340v       350v
Z2VK19(1,203)   GGGACCAAGCTGGAGCTGAAACGGGCTGATGCTGCACCAACTGTATCCA-
Z2VK20(1,204)   GGGACCAAGCTGGAGCTGAAACGGGCTGATGCTGCACCAACTGTATCCAT
Z2VK16(1,175)'  GGGACCAAGCTGGAGCTGAAACGGGCTGATGCTGCACCAACTGTATCCAT
Z2VK18A(1,167)' GGGACCAAGCTGGAGCTGAAACGGGCTGATG
Z2VK8B(1,154)'  GGGACCAAGCTGGAGCTGAAACGGG
CK2F0R(1,32)'                          GGGCTGATGCTGCACCAACTGTATCCAT
                                                GCTGCACCAACTGTATCCAT consensus       GGGACCAAGCTGGAGCTGAAACGGGCTGATGCTGCACCAACTGTATCCAT
```

FIG. 20H

```
              360v        370v        380v        390v        400v
Z2VK19(1,203) CTTCAAGCTT
Z2VK20(1,204) CTTCAAGCTT
Z2VK8B(1,154)' CTTCAAGCT
CK2FOR(1,32)'  CTTCAAGCTTCC consensus      CTTCAAGCTTCC
```

```
                                                                           120
              M                   F    T    B    A    N
 E  AS        A                   O    T    S    L    L
 C  PC        E                   K    H    M    W    A
 R  YR        3                   1    1    2    2    3
 2  11        /
    /
TTGCTCTGGTTTCCAGGTATCAGAGATGTGACATCAAGATGACCCAGTCTCCATCCTCCATG
----+----:----+----:----+----:----+----:----+----:----+----:
AACGAGACCAAAGGTCCATAGTCTCTACACTGTAGTTCTACTGGGTCAGAGGTAGGAGGTAC l  l  w  f  p  g  i  r  c  d  i  k  m  t  q  s  p  s  s  m

TATGCATCGCTGGGAGAGAGAGTCACTATCACTTGCAAGGCGAGTCAGGACATTAAAAGC
----+----.----+----.----+----.----+----.----+----.----+----      180
ATACGTAGCGACCCTCTCTCAGTGATAGTGAACGTTCCGCTCAGTCCTGTAATTTTCG y  a  s  l  g  e  r  v  t  i  t  c  k  a  s  q  d  i  k  s
```

FIG. 21D

```
      M  A  BANRKE         DSNDSBBBTN         D    E MDD
      S  L  ASLSPC         STCSESSTL          D    C BPP
      E  U  NPAAN1         AYOACAAHA          E    P ONN
      1  1  114115         11111JJ23          1    1 121
            / /  /         /////  /                /
                                                                                240
      TATTTAAGC TGGTACCAGCAGAGAAAACCATGGAAATCTCCTAAGACCCTGATCTAT TATGCA
      ---------+---------+---------+---------+---------+---------+
      ATAAATTCG ACCATGGTCGTCTCTTTTGGTACCTTTAGAGGATTCTGGGACTAGATA ATACGT y  l  s   w  y  q  q  k  p  w  k  s  p  k  t  l  i  y   a

```
       DNPPAANF    TH       BXMDD
  H A  RLPSVSLI    FN       IHBPP                              300
  I L  AAUSAUAN    IF       NOONN
  N U  24112141    11       12121
  3 1   / ////      /        ///
      ┌─────────────┐
      │ACAAGCTTGGGCAGAT│GGGGTCCCCATCAAGAGATTCAGTGGCAGTGGATCTGGGCAAGATTAT
       ----+----.----+----.----+----.----+----.----+----.----+
       TGTTCGAACCCGTCTA CCCCAGGGTAGTTCTAAGTCACCGTCACCCTAGACCCGTTCTAATA t  s  l  a  d    g  v  p  s  r  f  s  g  s  g  s  g  q  d  y
      └─────────────┘

```
        E   F E AS H   B   P              A
        C   N C PC N   B   L              C
        1   U R YR F   V   E              C
        5   H 2 11 1   1   1              1
            /
TCTCTAACCATCAGCAGCCTGGAGTCTGACGATACAGCAACTTATTACTGT CTACAGCAT
----+----+----+----+----+----+----+----+----+----+----+----+    360
AGAGATTGGTAGTCGTCGGACCCTCAGACTGCTATGTCGTTGAATAATGACA GATGTCGTA s l t i s s l e s d d t a t y y c    l q h
```

FIG. 21G

```
       N    BNAHT M       ANAF    A     A  SB             F
       L    ASCPT A       VLSI    L     L  FB             N
       A    NPIHH E       AAUN    U     U  AV             U
       3    22112 2       2411    1     1  N1             H
              //            /                    ⟶CK     420
GGTGAGAGCCCGCTCACGTTCGGTGCTGGGACCAAGCTGGAGCTGAAACGGGCTGATGCT
----+----.----+----.----+----.----+----.----+----.----+----
CCACTCTCGGGCGAGTGCAAGCCACGACCCTGGTTCGACCTCGACTTTGCCCGACTACGA g  e  s  p  l  t   f  g  a  g  t  k  l  e  l  k  r  a  d  a

```
                    M   H
                    B   I   A
                    O   N   L
                    2   3   U
                        1
GCACCAACTGTATCCATCTTCAAGCTTCC
----:----+----:----+----:----  449
CGTGGTTGACATAGGTAGAAGTTCGAAGG
 a   p   t   v   s   i   f
```

FIG. 22

```
                10v              20v              30v              40v              50v
Z2D3MUVK   DIQLTQSPSSMYASLGERVTIITC KASQDIKSYLS WYQQKPWKSPKTLIY YA
           DIQ TQSPSS  ASLG RVTITC  ASQDI   YL  WYQQKP   PK LIY YA
MUVKV      DIQMTQSPSSLSASLGDRVTITC RASQDISNYLN WYQQKPGGTPKLLIY YA
               10^              20^              30^              40^              50^

60v              70v              80v              90v              100v
Z2D3MUVK   TSLAD GVPSRFSGSGSGGQDYSLTISSLESDDTATYYC LQHGESPLT FGAGT
           L     GVPSRFSGSGSG DYSLTISSLE D ATY C  Q     P   TFG GT
MUVKV      SRLHS GVPSRFSGSGSGTDYSLTISSLEQEDIATYFC QQGNSLPRT FGGGT
               60^              70^              80^              90^              100^

Z2D3MUVK   KLELK
           KLE K
MUVKV      KLEIK
```

CHIMERIC Z2D3 F(ab')$_2$

NON-SPECIFIC HUMAN F(ab')$^2$

CHIMERIC Z2D3 F(ab')$_2$

NON-SPECIFIC HUMAN F(ab')$_2$

CHIMERIC Z2D3 F(ab')$_2$

NON-SPECIFIC HUMAN F(ab')$_2$

ATHEROSCLEROTIC PLAQUE SPECIFIC ANTIGENS, ANTIBODIES THERETO, AND USES THEREOF

This is a continuation of application Ser. No. 07/828,860, filed Jan. 31, 1992, abandoned which is a continuation-in-part of U.S. Ser. No. 07/388,129, filed Jul. 31, 1989, now abandoned the text of which is incorporated by reference into the subject application which in turn is a continuation-in-part of U.S. Ser. No. 07/067,995, filed Jun. 29, 1987, now abandoned; which in turn is a continuation-in-part of U.S. Ser. No. 07/067,993, filed Jun. 29, 1987, now abandoned; which in turn is a continuation-in-part of U.S. Ser. No. 07/067,986, filed Jun. 29, 1987, now abandoned; which in turn is a continuation-in-part of U.S. Ser. No. 06/876,741, filed Jun. 20, 1986, now abandoned; which in turn is a continuation-in-part of U.S. Ser. No. 06/871,811, filed Jun. 6, 1986, now abandoned; which in turn is a continuation-in-part of U.S. Ser. No. 06/846,401, filed Mar. 31, 1986, now abandoned.

BACKGROUND OF THE INVENTION

Atherosclerosis is the progressive narrowing of the lumen (inner passageway) of arterial blood vessels by layers of plaque (fatty and fibrous tissues). Atherosclerosis can occur in any artery. In coronary arteries it may result in heart attacks; in cerebral arteries it may result in strokes; and in peripheral arteries it may result in gangrene of the legs and feet.

Atherosclerosis is the single largest medical problem currently facing the United States and other developed countries. Approximately 40 million people in the United States are at risk for atherosclerosis. However, only 6 million people in the United States show overt signs of the disease. The rest remain undiagnosed until the disease manifests itself symptomatically, in the worst case as heart attack or stroke. Heart attack and stroke, respectively, represent the first and third leading causes of death in United States. Over 500,000 people die of heart attacks every year and a significant sub-group of these patients expire without warning.

The endothelium is located between the blood and arterial tissue and serves as a barrier against the accumulation of blood components in the vascular wall. Formation of atherosclerotic lesions in the sub-endothelium is associated with major coronary artery disease and stroke. The causes and detection of such lesions have been intensely investigated.

Endothelial injury is believed to be an initial step in the formation of the atherosclerotic lesions and may be caused by hemodynamic strain, hypercholesterolemia, hypertension and immune complex disease. Endothelial injury leads to cholesterol accumulation and intimal thickening, cellular proliferation, and formation of connective tissue fibers. IgG and complement factor C3 accumulation in injured endothelial cells and nonendothelialized intima has been observed. Mononuclear phagocytes derived from blood are also part of the cell population in atherosclerotic lesions. The mechanism of plaque formation is not fully known. However, a probable mechanism is that fatty deposits lead to an influx of macrophages, which in turn are followed by T cells, B cells, and antibody production.

A variety of soluble proteins have been extracted from human atherosclerotic plaque, including IgA, IgG, IgM, B1C(C3), alpha$_1$-antitrypsin, alpha$_2$-macroglobulin, fibrinogen, albumin, LDL, HDL, alpha$_1$-acid glycoprotein, $\beta_2$-glycoprotein, transferrin and ceruloplasmin. The diseased intima was also found to contain a small amount of tissue-bound IgG, IgA and B1C [Hollander, W. et al., Atherosclerosis, 34:391–405 (1979)]. IgG has been determined in lesions and adjacent endothelial tissue [Parums, D. et al., Atherosclerosis, 38:211–216 (1981), Hansson, G. et al., Experimental and Molecular Pathology, 34:264–280 (1981), Hannson, G. et al., Acta Path. Microbiol. Immunol. Scand. Sect. A., 92:429–435 (1984)]. However, the origin, function and binding properties of the immunoglobulins in the atherosclerotic and associated tissue are not well characterized. Anti-low density lipoprotein (LDL) autoantibodies are reported to be higher in patients of vascular disease, suggesting that they are associated in some way with atherosclerotic manifestations. However, no causal relationship between these autoantibodies and atherosclerotic plaque has been established. [Szondy, E. et al., Mechanisms of Aging and Development, 29:117–123 (1985)].

A wide variety of immunoassays have been developed for determining the presence and amount of antigenic and non-antigenic materials in diverse body fluids and tissues. Total immunoglobulin and IgE immunoassays are described in U.S. Pat. Nos. 3,720,760 and 4,444,879. IgG allotype immunoassays are described in Russian Patent 649,433. ELISA immunoassays are described by Maggio, et al. [Enzyme-Immunoassay, Boca Raton: CRC Press pp 172–176 (1980)]. However, prior to this invention, no immunoassay suitable for determining the presence of atherosclerotic plaque has been known.

Although atherosclerosis is generally a diffuse disease, human coronary atherosclerosis lends itself to bypass procedures because the major site of plaque formation is usually proximally distributed. As a result, direct coronary artery bypass has become the most frequently selected form of myocardial revascularization. The aorta-coronary artery vein graft or the internal mammary artery graft have become technically standardized and have high long-term potency rates. These long-term results, however, can be compromised by progressive atherosclerosis distal to the graft anastomosis. Other cases are inoperable because of distal disease. Previously, distal lesions have been ignored or, in selected cases, treated by endarterectomy although neither approach has proved entirely satisfactory.

Most existing procedures for the diagnosis and treatment of atherosclerosis are invasive, costly, and of limited effectiveness in a significant percentage of patient cases.

Prior to the subject invention, radioimaging of atherosclerotic plaque using an antibody which specifically binds to an atherosclerotic plaque specific antigen was unknown, although radioimaging of aged venous thrombi with fibrin-specific monoclonal antibodies labeled with a radioactive moiety has been reported [Rosebrough, S. et al., Radiology 162:575–577 (February, 1987)].

Radioimaging thrombi with radiolabeled monoclonal antibodies to platelets was first described by Peters, A., et al. [British Medical Journal, 293:1525–1527 (December, 1986)]. DTPA-coupled antibodies radiolabeled with metallic radionuclides has been described by Hnatowich, D., et al. [Journal of Immunological Methods, 65:147–157 (1983)].

NMRI, ultrasound and X-ray imaging with metal chelates are described in U.S. Pat. No. 4,647,447. In addition, antibody coupling of metal chelates is mentioned at column 7, line 42. Monoclonal antibodies labeled with polymeric paramagnetic chelates and their use in NMRI methods have also been described [Shreve, P. et al., Magnetic Resonance in Medicine, 3:336–340 (1986) and Brady, T. et al. in Proceedings of the Society of Magnetic Resonance in Medicine, Second Annual Meeting, Soc. of Magnetic Resonance in Medicine, Inc., San Francisco, p. 10, (1983), referenced by Koutcher, J. et al., J. Nucl. Med., 25:506–513 (1984)].

U.S. Pat. No. 4,343,734 (Lian et al.) describes gamma-carboxyglutamic acid (GLA) specific antibodies which can be labeled with fluorescein for immunofluorescence staining of tissue to determine the presence therein of GLA. GLA specific antibodies bind with GLA present in advanced atherosclerotic plaque having calcium deposits. Lian et al. report that GLA is not found in uncalcified plaques and that GLA is found in cardiac valves and aortas, and in circulating proteins such as prothombin, clotting factors VII, IX and X, Protein C and Protein S. However, the GLA binding antibodies of Lian et al. do not selectively bind to atherosclerotic plaque.

The atherosclerotic plaque antibodies of the subject invention bind to all stages of atherosclerotic plaque including non-calcified stages, and do not selectively bind with GLA.

The concept of plaque enhancement by application of a stain has been reported [Spears, J. et al., J. Clin. Invest, 71:395–399 (1983)]. These stains mark the plaque surfaces with a fluorescent compound. Plaque destruction by photoactivation of hematoporphyrin derivatives using an intraluminal. laser-transmitting optical fiber has been suggested [Abela, G. et al., Am. J. Cardio., 50:1199–1205 (1982)]. Moreover, tetracycline stains have also been suggested. [Murphy-Chutorian, D. et al., Am. J. Cardiol., 55:1293–1297 (1985)].

The above-identified stains were selected for their ability to bind to components of the atherosclerotic plaque. In principal, the stain absorbs laser light concentrating the light at the stained surface. Some staining of healthy tissue occurs causing stain associated damage to the surrounding tissue. Because laser wavelength is limited to the absorption wavelength of the stain, chromophores offering optimum absorption of laser must be used to provide most controlled ablation.

In recent years, lasers have been used increasingly in microsurgery, both as scalpels and as coagulating instruments. Because of their ability to produce relatively bloodless incisions of great precision, as well as focal coagulation, they have been particularly useful in microsurgical procedures in the eye, central nervous system, nasal passages, cervix, gastrointestinal tract, skin, muscle, and even in small vessels.

In vivo experiments with heart and arterial tissue from human cadavers have demonstrated the feasibility of vaporizing or etching away plaque on diseased surfaces. UV-wavelengths were found to offer more precision. Laser treatment of plaque in live animals was less precise, causing damage and perforation of surrounding healthy tissue. [Gerrity, R. et al. J. Thorac. Cardiovasc. Surg., 85:409–421 (1983); Lee, G. et al., Am Heart J., 105:885–889 (1983); Lee, G. et al., Am. Heart J., pp 777–778. (August 1984); Lee, G. et al., Am. Heart J., 108:1577–1579 (1984); Lee, G. et al., Am. J. Cardiology, 53:290–293 (1984); Linsker, R. et al., Lasers in Surgery and Medicine, 4:201–206 (1984); Abela, G. et al., Circulation, 71(2):403–411 (1985); Prince, N. et al., J. Clin. Invest., 78:295–302 (1986); and Srinivasan, R., Science, 234:559–565 (1986)].

Recent reference has been made to monoclonal antibodies targeting differential antigens in atherosclerotic plaque. These antigens have included oxidized or otherwise modified lipoproteins (Haberland, M. E., et al., Science 241: 215 (1988)) and glycosylated connective tissue proteins (Curtiss, L. K. and Witztum, J. L., J. Clin. Invest, 87: 1436 (1983)). While concentrated within the plaque substance, these antigens have also been found in normal artery and/or other normal tissues. Some antigens and their corresponding monoclonal antibodies have shown early promise in the Watanabe rabbit model but have not held up when applied to human lesions (Shih, I. L., et al., Proc. Natl. Acad, Sci., 87: 1436 (1990)), especially when diffuse markers of extracellular plaque tissue are being sought (Kimura, J., et al., Virchows Arch., 410(2): 159 (1986)).

The subject invention provides an inexpensive, accurate method for determining the presence of atherosclerotic plaque both in vitro and in vivo. In addition, the subject invention provides methods of treating persons having atherosclerotic plaque which include enzyme treatment, and laser treatment. Lastly, the subject invention provides a method of drug delivery to areas of atherosclerotic plaque.

SUMMARY OF THE INVENTION

The subject invention provides a purified antigen indicative of the presence of atherosclerotic plaque characterized as having a complex carbohydrate structure having a molecular weight greater than 200,000 daltons and being present as an extracellular component of atherosclerotic plaque. The subject invention also provides a purified antigen wherein the antigen is characterized by its selective binding to the monoclonal antibody produced by hybridoma Q10E7. These antigens are characterized by existing in amounts which vary with the progression of atherosclerosis. The subject invention further provides antibodies to these antigens and methods of detecting the presence of both the antigens and the antibodies thereto. Methods for treating atherosclerosis are also provided.

The subject invention also provides a method for reducing the amount of atherosclerotic plaque in a blood vessel which comprises: a) contacting the atherosclerotic plaque with a reagent which is capable of specifically binding to both the plaque and to a proenzyme, the substrate of which enzyme is a connective tissue present in atherosclerotic plaque which, when cleaved, is capable of dissolving a component of the plaque under conditions such that the reagent binds to the plaque so as to form a reagent-plaque complex; b) contacting the reagent-plaque complex with the proenzyme to which the reagent specifically binds under conditions such that the proenzyme is bound to the reagent forming a proenzyme-reagent-plaque complex; and c) contacting the proenzyme-reagent-plaque complex with an agent which is capable of specifically cleaving the proenzyme so that the proenzyme is converted into the enzyme under conditions such that the enzyme digests the plaque.

The subject invention further provides a method for diagnostic analysis comprising the steps of: a) obtaining a value for the body mass index (BMI) of a patient; b) obtaining a value for the concentration of an antigen or other serum or plasma analytes associated with a pathological condition or an antibody which binds with the antigen; c) plotting the body mass index of the patient against the antigen or antibody concentration of the same patient; and d) comparing the resulting value against a set of reference values to determine whether the resulting value exceeds the reference value and thereby indicates the presence of a pathological condition.

BRIEF DESCRIPTION OF THE FIGURES

FIG. 17—Positive prevalence of antibody which specifically binds to atherosclerotic plaque antigen, for various age groups. Solid bars represent IgG. Cross-hatched bars represent IgA.

FIG. 18—Positive prevalence of either, or both, IgG or IgA which specifically binds to atherosclerotic plaque antigen for various age groups.

FIG. 19—Positive prevalence of either antibody (IgG or IgA) or antigen for various age groups.

FIG. 20—A chromatographic blank run with just distilled water using a Dionex instrument for monosaccharides analysis with a CPPA-1 column.

FIG. 21—Chromatographic run of seven standard monosaccharides using a Dionex instrument for monosaccharides analysis with a CPPA-1 column, 15 mM NaOH in purified water.

FIG. 22—Chromatographic blank run with the auto-antigen affinity purification with the 15H5 monoclonal antibody using a Dionex instrument for monosaccharides analysis with a CPPA-1 column, 15 mM NaOH in purified water.

Figure 1A:
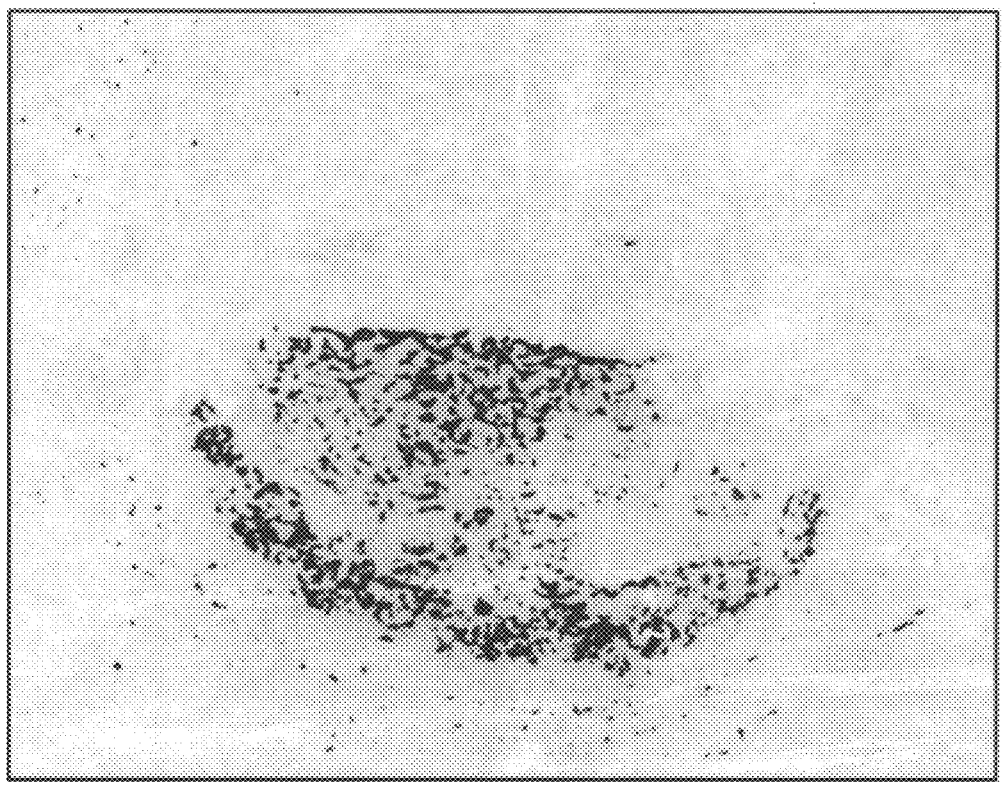
FIG. 1—Pathways used for developing antibodies to the various stages of the atherosclerotic plaque specific antigen and for testing the antigen and antibodies made thereto.
Figure 1B:
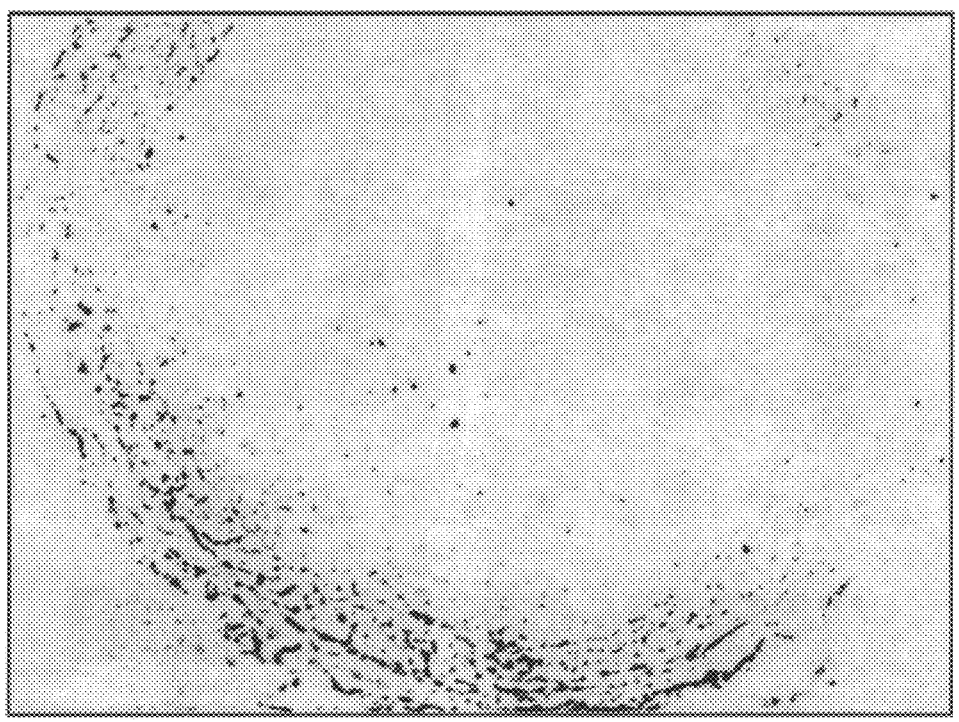

30A. Representation of the bifunctional antibody.

30B. Representation of the bifunctional antigen binding to Z2D3 antigen.

30C. Representation of the enzyme including the propeptide portion which inhibits enzyme activity.

30D. Representation of the antigen-bifunctional antibody proenzyme complex.

30E. Representation of the complex after cleavage of the propeptide following treatment with tissue plasminogen activator, and the enzyme initiating plaque lysis.

DETAILED DESCRIPTION OF THE INVENTION

The subject invention a purified antigen indicative of the presence of atherosclerotic plaque characterized as having a complex carbohydrate structure and a molecular weight greater than 200,000 daltons and as being present as an extracellular component of atherosclerotic plaque.

This antigen is characterized by being synthesized by, or present in, smooth muscle cells. It has been purified and is characterized by its selective binding to the monoclonal antibody produced by hybridoma 15H5 (ATCC Accession No. HB9839). This antigen is further characterized by being neutral in charge. This antigen is also characterized by having a carbohydrate profile depicted in FIG. 22. It has been determined that the 15H5 antigen selectively binds to lectins. Accordingly, this can be further characterized by binding to the lectins *Conavalia ensiformis, Triticum vulgaris, Lens culinaris, Ricinus commonis,* and *Triticum vulgaris,* and by not binding to the lectins *Arachis hypgaea, Bandeiraea simplicitolia, Diolichos biflorus, Glycine Max, Limulus polyphenus, Phaseolus vulgaris-E, Phaseolus vulgaris-L, Pisum sativum, Sophova japonica, Ulex europaes, Ulex europaeus,* and *Vicia villosa.*

Another way of determining the characteristics of a molecule is examine the actions of various enzymes upon the molecule. The 15H5 antigen is further characterized as being resistant to degradation by proteinases, deoxyribonucleases, lipases, and ribonucleases, while being partially susceptible to degradation by α-amylase, β-amylase, and glucoamylase.

To determine whether the 15H5-antigen was a molecule known to be associated with atherosclerotic plaque, the antigen was evaluated for binding to antibodies which specifically bind to known components of atherosclerotic plaque. The antigen may be further characterized as being non-reactive with antibodies which bind to apolipoproteins, human collagen, fibronectin, keratin, laminin, tenascin, and vitronectin.

Other characteristics of the antigen include being reactive with the monoclonal antibody produced by hybridoma 15H5 (ATCC Accession No. HB 9839) after the antigen has been boiled for one hour, and being reactive with the monoclonal antibody produced by hybridoma 15H5 (ATCC Accession No. HB 9839) after the antigen has been treated with 8M urea in phosphate buffered saline for 24 hours at room temperature, 6M guanidine HCl in phosphate buffered saline for 24 hours at room temperature, 2M trifluroacetic acid for 30 minutes at room temperature, 3.5M sodium thiocyanate in phosphate buffered saline for 8 hours at room temperature, or 0.19M sodium dodecyl sulfate in phosphate buffered saline for one hour at room temperature.

The subject invention also provides an antigen or epitope associated with atherosclerosis and some normal tissue, characterized by its selective binding to the monoclonal antibody produced by hybridoma 17H3 (ATCC Accession No. HB 10189).

Another antigen is provided by the subject invention, which antigen is characterized by being synthesized by, or present in, atherosclerotic plaque connective tissue and plaque smooth muscle cells is the antigen characterized as being a lipid-containing molecule which selectively binds to the monoclonal antibody produced by hybridoma Z2D3 (ATCC Accession No. HB 9840) or by hybridoma Z2D3/3E5 (ATCC Accession No. HB 10485). This antigen may be further characterized by having its ability to be used for histological staining destroyed upon treatment with acetone.

Also provided are antigens indicative of the presence of normal smooth muscle cells. One such antigen is characterized by its selective binding to the monoclonal antibody produced by hybridoma Q10E7 (ATCC Accession No. HB 10188). The molecular weight of this antigen is greater than 150,000 daltons. This antigen is further characterized by being synthesized by, or present in, normal smooth muscle cells and normal connective tissue surrounding arteries.

In one embodiment of the subject invention, an above-described antigen is labeled with a detectable marker. This marker may be any marker known to one skilled in the art. However, in the preferred embodiment the marker is an enzyme, a paramagnetic ion, biotin, a fluorophore, a chromophore, a heavy metal, or a radioisotope. In most cases involving immunoassays, the preferred marker is an enzyme, preferably horseradish peroxidase or alkaline phophatase.

The subject invention also provides purified antibodies which specifically bind to an atheroclerotic plaque antigen or to an antigen associated with normal smooth muscle cells and connective tissue. In one embodiment, the antibody is labeled with a detectable marker. The choice of marker used will vary depending upon the application. However, the choice of marker is readily determinable to one skilled in the art. In a preferred embodiment of this invention the marker is an enzyme, a paramagnetic ion, biotin, a fluorophore, a chromophore, a heavy metal, or a radioisotope. These labeled antibodies may be used in immunoassays as well as in histological applications to detect the presence of atherosclerotic plaque. In such applications it is preferred that the marker is an enzyme, and it is most preferred that the enzyme is horseradish peroxidase or alkaline phosphatase.

The above-identified antibodies may be either polyclonal or monoclonal, with the monoclonal antibody being a preferred embodiment.

This invention provides monoclonal antibodies directed to atherosclerotic plaque antigens which include the monoclonal antibody produced by hybridoma 15H5 (ATCC Accession No. HB9839); the monoclonal antibody produced by hybridoma Z2D3 (ATCC Accession No. HB9840) and Z2D3/3E5 (ATCC Accession No. HB 10485), an IgG, which is a class switch variant of Z2D3, which is an IgM, as well as other daughter cell lines of Z2D3 such as Z2D3/5C5 (an IgG); and the monoclonal antibody produced by hybridoma 17H3 (ATCC Accession No. HB 10189). The monoclonal antibody produced by hybridoma Q10E7 (ATCC Accession No. HB 10188) is directed toward normal artery. Hybridomas 15H5, Z2D3, Z2D3/3E5, 17H3 and Q10E7 were deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. HB 9839, HB 9480, HB 10485, HB 10189, and HB 10188, respectively.

The invention provides a recombinant polypeptide which comprises an amino acid sequence which is substantially the same as the amino acid sequence of the hypervariable region of monoclonal antibody Z2D3, Z2D3/3E5 and other daughter cells lines of Z2D3 or Q10E7. One may also obtain such a polypeptide by nonrecombinant methods, such as for example, proteolytic digestion.

A chimeric antibody or a fragment thereof comprising such a recombinant polypeptide is also provided, particularly a chimeric antibody comprising the amino acid sequences of a human framework region and of a constant region from a human antibody so as to "humanize" or render nonimmunogenic the hypervariable region of the mouse Z2D3, Z2D3/3E5 or Q10E7. Also provided is the polypeptide or chimeric antibody or fragment derived by site-directed mutagenesis, especially site-directed mutagenesis which confers equivalent or better binding properties. The fragments of the chimeric antibody include Fab, F(ab)$_2$, F$_V$ and V$_N$ fragments.

The subject invention also provides for an atherosclerotic plaque antigen bound to a solid support and an antibody which specifically binds to an atherosclerotic plaque antigen bound to a solid support. In a preferred embodiment, the monoclonal antibody produced by hybridoma 15H5 is bound to a solid support.

Anti-plaque antibody or the atherosclerotic plaque antigen may be bound to an insoluble support by conventional processes. Procedures for binding of antibodies to insoluble supports are described in U.S. Pat. Nos. 3,551,555, 3,553,310, 4,048,298 and RE-29,474, for example. Binding of antibodies to polystyrene by adsorption has been described in U.S. Pat. Nos. 3,646,346 and 4,092,408, for example. Binding of protein containing antigens to a variety of insoluble supports has been described in U.S. Pat. No. 3,720,760.

A variety of materials may be used as the insoluble support, the primary consideration being the binding characteristics of the anti-plaque antibody or the plaque antigen to the surface, the absence of interference with the anti-plaque antibody and plaque antigen conjugating reaction or with other reactions which may be employed to determine the presence and extent of the conjugating reaction. Organic and inorganic polymers, both natural and synthetic, can be used as the insoluble support. Examples of suitable polymers include polyethylene, polypropylene, polybutylene, poly(4-methylbutlyene), butyl rubber, silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which can be used as the insoluble suport can the latexes of the above polymers, silica gel, silicon wafers, glass, paper, insoluble protein, metals, metalloids, metal oxides, magnetic materials, semi-conductive materials, cermets and the like. In addition are included substances which form gels, such as proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphophilic compounds such as pohospholipids, long chain (12–24 carbon atoms) alkyl ammonium salts and the like.

One diagnostic support comprises polystyrene, styrene copolymers, or polyolefins such as polyethylene or polypropylene, and acrylate and methacrylate polymers and copolymers. The anti-plaque reagent antibody or the plaque antigen can be bound to the insoluble support by adsorption, ionic bonding, van der Waals adsorption, electrostatic bonding, or other non-covalent bonding, or it can be bound to the insoluble support by covalent bonding. A particularly advantageous support for this procedure comprises a microtiter plate having a plurality of wells. The well surface or plastic cup inserts therein can constitute the antigen or antibody support. If the determination will require the use of fluorometric measurements, the microtiter plate or the well inserts are advantageously opaque to light so that excitation light applied to a well does not reach or influence contents of the surrounding wells.

Procedures for non-covalent bonding are described in U.S. Pat. No. 4,528,267. Procedures for covalently bonding antibodies and antigens to insoluble supports are described by Ichiro Chibata [Immobilized Enzymes, Halsted Press: New York (1978)] and A. Cuatrecasa, [J. Bio. Chem., 245:3059 (1970)], the entire contents of which are hereby incorporated by reference. The surface can be coated with a protein and coupled with the antibody or antigen using procedures described in U.S. Pat. No. 4,210,418 using glutaraldehyde as a coupling agent, for example. In a still further procedure, the well can be coated with a layer having free isocyanate groups such as a polyether isocyanate, and application of the antibody or antigen in aqueous solution thereto effects the requisite bonding. In a still further procedure, the antibody or antigen can be coupled to a hydroxylated material by means of cyanogen bromide as described in U.S. Pat. No. 3,720,760.

The subject invention also provides a method for detecting in a biological sample an antigen present in, and indicative of the presence of, atherosclerotic plaque which comprises contacting the biological fluid with the antibody which specifically binds to the atherosclerotic plaque antigen under conditions such that the antibody binds to the antigen to form a detectable complex, detecting the complex so formed and thereby detecting any antigen in the biological sample.

In a preferred method the biological sample is a tissue sample. Tissue samples may be used in a variety of histological techniques including but not limited to those illustrated throughout the application.

In another embodiment the biological sample is a biological fluid. It is preferred that the biological fluid comprises blood, plasma, or serum. However, in the more preferred embodiment the biological fluid is serum. To further aid in detecting the complex it is preferred that the antibody which binds specifically to the atherosclerotic plaque antigen is labeled with a detectable marker. The choice of marker is readily determinable to one skilled in the art. In one embodiment of the subject method, the antibody is a monoclonal antibody and more preferably the monoclonal antibody is produced by hybridoma 15H5 (ATCC Accession No. HB9839). To further aid in detecting the complex, it is preferred that the antibody be bound to a solid support. One preferred solid support is a bead formed of an inert polymer and another is a microwell.

The subject invention also provides a method for quantitatively determining in a sample of a biological fluid the concentration of an antigen which is present in, and indicative of the presence of, atherosclerotic plaque which comprises: a) contacting a solid support with an excess of an antibody which binds specifically to an atherosclerotic plaque antigen under conditions permitting the antibody to attach to the surface of the solid support; b) removing unbound antibody; c) contacting the resulting solid support to which the antibody is bound with the sample of the biological fluid under conditions such that any antigen present in the sample binds to the bound antibody and forms a complex therewith; d) removing any antigen which is not bound to the complex; e) contacting any complex so formed with an excess of a detectable reagent which specifically binds to any antigen present in the complex so as to form a second complex which includes the antibody, the antigen, and the detectable reagent; f) removing any detectable reagent which is not bound in the second complex; g) quantitatively determining the concentration of detectable reagent present in the second complex; and h) thereby quantitatively determining the concentration of antigen in the biological fluid.

One embodiment of this method is wherein the biological fluid comprises blood, plasma, or serum. More preferably, the biological fluid is serum.

In one embodiment the solid support is a bead formed of an inert polymer and in another the solid support is a microwell.

In one embodiment the reagent is labeled with a detectable marker, the choice of marker being determinable by one skilled in the art.

In a preferred embodiment, the marker is an enzyme, a paramagnetic ion, biotin, a fluorophore, a chromophore, a heavy metal, or a radioisotope. Although any reagent capable of detecting the atherosclerotic plaque antigen may be employed, it is preferred that the reagent is an antibody labeled with a detectable marker. Again, it is preferred that the marker is an enzyme, a paramagnetic ion, biotin, a fluorophore, a chromophore, a heavy metal, or a radioisotope. More preferably, the marker is an enzyme, particularly effective enzymes being horseradish perosidase alkaline phosphatase.

The subject invention also provides for the above method wherein the detectable reagent is labeled with an enzyme and step (g) comprises contacting the second complex with a specific substrate for the enzyme under conditions such that the enzyme reacts with the substrate to form a detectable product.

Another provision of the subject invention is a method for detecting in a biological sample an antibody which specifically forms a complex with an antigen present in, and indicative of the presence of, atherosclerotic plaque which comprises contacting the biological sample with an atherosclerotic plaque antigen under conditions such that the antigen binds to the antibody in the biological sample and detecting the antigen bound to the antibody and thereby detecting the antibody in the biological sample.

In a preferred embodiment the biological sample is a tissue sample. Tissue samples may be used in any histological technique known to one skilled in the art to detect and quantify the amount of antibody in the sample. The methods include, but are not limited to, the illustrations provided throughout the application.

A preferred embodiment of the above-described method is wherein the biological sample is a biological fluid. In one preferred embodiment the biological fluid comprises blood, plasma, or serum. More preferably the biological fluid is serum. To aid in detecting the complex formed, it is preferred that the antigen is labeled with a detectable marker. Another embodiment of the invention is wherein the antigen is bound to a solid support. This allows the complex to be readily separated from the biological fluid and be detected. One preferred embodiment is wherein solid support is a bead formed of an inert polymer, and another is wherein the solid support is a microwell.

The subject invention also provides a method for quantitatively determining in a sample of a biological fluid the concentration of an antibody which specifically forms a complex with an antigen present in, and indicative of the presence of, atherosclerotic plaque which comprises: a) contacting a solid support with an excess of an atherosclerotic plaque antigen under conditions permitting the antigen to attach to the surface of the solid support; b) removing unbound antigen; c) contacting the resulting solid support to which the antigen is bound with the sample of the biological fluid under conditions such that any antibody present in the sample binds to the bound antigen and forms a complex therewith; d) removing any antibody which is not bound to the complex; e) contacting any complex so formed with an excess of a detectable reagent which specifically binds to any antibody present in the complex so as to form a second complex which includes the antigen, the antibody, and the detectable reagent; f) removing any detectable reagent which is not bound in the second complex; g) quantitatively determining the concentration of detectable reagent present in the second complex; and h) thereby quantitatively determining the concentration of antibody in the biological fluid.

In one preferred embodiment the biological fluid comprises blood, plasma, or serum. More preferably, the biological fluid is serum.

To better detect the complex formed it is preferred that the reagent is labeled with a detectable marker. Preferably, the marker is an enzyme, a paramagnetic ion, biotin, a fluorophore, a chromophore, a heavy metal, or a radioisotope. More preferably, the marker is an enzyme. The most preferred embodiment is when the enzyme is horseradish peroxidase or alkaline phosphatase.

A further embodiment of the above-described method is wherein the detectable reagent is labeled with an enzyme and step (g) comprises contacting the second complex with specific substrate to the enzyme under conditions such that the enzyme reacts with the substrate to form a detectable product.

The subject invention discloses a method for quantitatively determining in a sample of a biological fluid the concentration of an antigen which is present in, and indicative of the presence of, atherosclerotic plaque which comprises: a) contacting a solid support with a predetermined amount of an antibody which binds specifically to atherosclerotic plaque under conditions permitting the antibody to attach to the surface of the support; b) removing unbound antibody; c) contacting the resulting solid support to which the antibody is bound with a predetermined amount of antigen labeled with a detectable marker and with a sample of the biological fluid under conditions such that the antigen binds to the antibody bound to the solid support and forms a complex therewith; d) removing labeled antigen which is not bound to the complex; e) quantitatively determining the concentration of labeled antigen bound to the solid support; and f) thereby quantitatively determining the concentration of antigen in the biological fluid.

In one embodiment the biological fluid comprises blood, plasma, or serum. However, the presently preferred biological fluid is serum.

One preferred solid support is a bead formed of an inert polymer, and another is wherein the solid support is a microwell.

In one embodiment of the subject method the detectable marker is an enzyme, a paramagnetic ion, biotin, a fluorophore, a chromophore, a heavy metal, or a radioisotope. Preferably, the marker is an enzyme, and more preferably the enzyme is horseradish peroxidase or alkaline phosphatase.

In a further embodiment of the above-described method, the antigen is labeled with an enzyme and step (e) comprises contacting the labeled antigen bound to the solid support with specific substrate to the enzyme under conditions such that the enzyme reacts with the substrate to form a detectable product.

The subject invention further provides a method for quantitatively determining in a sample of a biological fluid the concentration of an antigen which is present in, and indicative of the presence of, atherosclerotic plaque which comprises: a) contacting a solid support with a predetermined amount of an antibody which specifically binds to an atherosclerotic plaque antigen under conditions permitting the antibody to attach to the surface of the support; b) removing any antibody not bound to the support; c) contacting the solid support to which the antibody is bound with the sample of the biological fluid under conditions such that any antigen present in the sample binds to the bound antibody and forms a complex therewith; d) removing any antigen which is not bound to the complex; e) contacting the complex so formed with a predetermined amount of plaque antigen labeled with a detectable marker under conditions such that the labeled antigen competes with the antigen from the biological fluid for binding to the antibody; f) quantitatively determining the concentration of labeled antigen not bound to the solid support; and g) thereby quantitatively determining the concentration of antigen in the biological fluid.

One embodiment of this method is wherein the biological fluid comprises blood, plasma, or serum. Preferably, the biological fluid is serum.

In one embodiment, the solid support is a bead formed of an inert polymer, and in another, the solid support is a microwell.

As discussed hereinabove, the choice of marker is readily determined by one skilled in the art. However, in a preferred embodiment the marker is an enzyme, a paramagnetic ion, biotin, a fluorophore, a chromophore, a heavy metal, or a radioisotope. More preferably, the marker is an enzyme. Although many enzymes produce a detectable product, preferred enzymes are horseradish peroxidase and alkaline phosphatase.

In a further embodiment of this method, the antigen is labeled with an enzyme and step (f) comprises removing the labeled antigen which was not bound to the solid support and contacting it with a specific substrate to the enzyme under conditions such that the enzyme reacts with the substrate to form a detectable product.

Another method provided for the subject invention is a method for quantitatively determining in a sample of a biological fluid the concentration of an antibody which specifically forms a complex with an antigen which is present in, and indicative of the presence of, atherosclerotic plaque which comprises: a) contacting a solid support with a predetermined amount of an atherosclerotic plaque antigen under conditions permitting the antigen to attach to the surface of the support; b) removing unbound antigen; c) contacting the resulting solid support to which the antigen is bound with a predetermined amount of an antibody labeled with a detectable marker and with the sample of biological fluid under conditions such that the antibody binds to the antigen bound to the solid support and forms a complex therewith; d) removing any antibody which is not bound to the complex; e) quantitatively determining the concentration of labeled antibody bound to the solid support; and f) thereby quantitatively determining the concentration of antibody in the biological fluid.

One embodiment of this invention is wherein the biological fluid comprises blood, plasma, or serum. More preferably, the biological fluid is serum.

In one preferred embodiment, the solid support is a bead formed of an inert polymer, and in another, the solid support is a microwell.

The choice of detectable marker may be readily determined by one skilled in the art. It is preferred, however, that the detectable marker is an enzyme, a paramagnetic ion, biotin, a fluorophore, a chromophore, a heavy metal, or a radioisotope. More preferably, the marker is an enzyme, and most preferably the enzyme is horseradish peroxidase or alkaline phosphatase.

In a further embodiment of this method, the antibody is labeled with an enzyme and step(e) comprises contacting the labeled antibody which was displaced from the solid support with a specific substrate to the enzyme under conditions such that the enzyme reacts with the substrate to form a detectable product.

The subject invention further discloses a method for quantitatively determining in a sample of a biological fluid the concentration of antibody which specifically forms a complex with an atherosclerotic antigen which is present in, and indicative of the presence of, atherosclerotic plaque which comprises: a) contacting a solid support with a predetermined amount of an atherosclerotic plaque antigen under conditions permitting the antigen to attach to the surface of the support; b) removing any antigen which is not bound to the support; c) contacting the solid support to which the antigen is bound with the sample of the biological fluid under conditions such that any antibody present in the sample binds to the bound antigen and forms a complex therewith; d) removing any antibody which is not bound to the complex; e) contacting the complex so formed with a predetermined amount of a plaque antibody labeled with a detectable marker under conditions such that the labeled antibody competes with the antibody in the biological fluid for binding to the antigen; f) quantitatively determining the concentration of labeled antibody not bound to the solid support; and g) thereby quantitatively determining the concentration of antibody in the biological fluid.

In one embodiment the biological fluid comprises blood, plasma, or serum. However, the preferred biological fluid is serum.

The choice of solid support may be readily determined by one skilled in the art. In one preferred method, the solid support is a bead formed of an inert polymer, in another the solid support is a microwell. The markers used in the above-described method are a matter of choice to one skilled in the art. It is preferred that the detectable marker is an enzyme, a paramagnetic ion, biotin, a fluorophore, a chromophore, a heavy metal, or a radioisotope. More preferably, the marker is an enzyme, and most preferably, the enzyme is horseradish peroxidase or alkaline phosphatase.

A further embodiment of this method is wherein the antibody is labeled with an enzyme and step (f) comprises removing the labeled antigen which was not bound to the solid support and contacting it with specific substrate to the enzyme under conditions such that the enzyme reacts with the substrate to form a detectable product.

The subject invention also provides a method for monitoring the progression of atherosclerosis which comprises determining the amount of atherosclerotic plaque antigen present in a sample of biological fluid of patient, and comparing the amount determined with the amount determined at earlier points of time, any change in the amount of antigen indicating a change in the extent of atherosclerotic plaque.

Another provision of this invention is for a method for monitoring the efficacy of treatment of atherosclerosis which comprises determining the amount of the atherosclerotic plaque antigen present in a sample of a biological fluid of a patient and comparing the amount determined at earlier points in time with a change in the amount of antigen indicating a change in the extent of atherosclerotic plaque.

Further disclosed by the invention is a reagent for use in imaging atherosclerotic plaque which comprises an antibody which binds specifically to atherosclerotic plaque antigen labeled with a detectable marker. This invention also provides a composition comprising an amount of this reagent and a physiologically acceptable carrier.

The detectable marker used is a matter of choice to one skilled in the art. It is preferred that the marker be a radioactive isotope, an element which is opaque to X-rays, a paramagnetic ion, or a chelate of a paramagnetic ion.

Radioactive isotopes are commonly used in medicine and are well known to those skilled in the art. It is presently preferred that the marker be I-123, I-125, I-128, I-131, or a chelated metal ion of chromium-51, cobalt-57, gallium-67, indium-111, indium-113m, mercury-197, selenium-75, thalium-201, technetium-99m, lead-203, strontium-85, strontium-87, gallium-68, samarium-153, europium-171, ytterbium-169, zinc-62, rhenium-188, or mixtures thereof. Preferably, the marker is technetium, iodine, indium or a metal ion chelate thereto.

In another embodiment of the above-identified method, the marker is a paramagnetic ion. Paramagnetic ions are also commonly used in medicine. Examples of such markers included chelated metal ion of chromium (III), manganese (II), iron (III), iron (II), cobalt (II), nickel (II), copper (II), praseodymium (III), neodyminum (III), samarium (III), gadolinium (III), terbium (III), dysprosium (III), holmium (III), erbium (III), ytterbium (III), or mixtures thereof.

The subject invention also provides a method for imaging atherosclerotic plaque which comprises contacting the atherosclerotic plaque to be imaged with a reagent which binds specifically to the atherosclerotic plaque antigen described above, under conditions such that the reagent binds to the atherosclerotic plaque and detecting the reagent bound thereto, thereby imaging the atherosclerotic plaque.

Also provided is a method for imaging atherosclerotic plaque and adjacent normal tissue which comprises contacting the normal lumen to be imaged with an antibody which specifically binds to normal intima and/or media and which is labeled with a detectable marker; contacting the atherosclerotic plaque with a reagent described above under conditions such that the reagent binds to the atherosclerotic plaque; and detecting the reagents bound to the atherosclerotic plaque and adjacent normal tissue, thereby imaging the atherosclerotic plaque and adjacent normal tissue. The antibody which specifically binds to normal intima and/or media is a purified antibody which specifically binds to an antigen characterized by being synthesized by, or present in, normal smooth muscle cells and normal connective tissue surrounding arteries. In a preferred embodiment, the antibody is a monoclonal antibody produced by hybridoma Q10E7 (ATCC Accession No. HB 10188).

The subject invention provides reagents for use in the method described above for imaging normal intima and/or media comprising an antibody labeled with a detectable marker as well as a composition comprising an effective imaging amount of such reagents and a physiologically acceptable carrier.

As described for the reagent for use in imaging atherosclerotic plaque, the detectable marker used is a matter of choice to one skilled in the art. It is preferred that the marker be a radioactive isotope, an element which is opaque to X-rays, a paramagnetic ion, or a chelate of a paramagnetic ion. Markers that may be used in imaging normal tissue correspond to those described above for imaging atherosclerotic plaque.

Another provision of the subject invention is a method for monitoring the progression of atherosclerosis which comprises determining the amount of an atherosclerotic plaque specific antigen present in a patient's blood vessels and comparing the amount determined with the amount determined at earlier points in time, a change in the amount of antigen indicating a change in the extent of atherosclerotic plaque.

Further provided is a method for monitoring the efficacy of treatment of atherosclerosis which comprises determining the amount of an atherosclerotic plaque specific antigen present in a patient's blood vessels and comparing the amount determined with the amount determined at earlier points in time, a change in the amount of antigen indicating a change in the extent of atherosclerotic plaque.

Also provided for is a method for imaging atherosclerotic plaque in a subject which comprises: a) contacting the blood vessel walls containing atherosclerotic plaque with the above-described reagent for imaging plaque; b) detecting the reagent bound to the atherosclerotic plaque; and c) imaging the atherosclerotic plaque.

A method for imaging atherosclerotic plaque and adjacent normal tissue in a subject which comprises contacting the normal lumen to be imaged with an antibody which specifically binds to normal intima and/or media and which is labeled with a detectable marker; contacting the blood vessel walls containing atherosclerotic plaque and surrounding area to be imaged with the reagent of claim 118 under conditions such that the reagent binds to the atherosclerotic plaque; and detecting the reagents bound to the atherosclerotic plaque and adjacent normal tissue, thereby imaging the atherosclerotic plaque and adjacent normal tissue. In a preferred embodiment, the antibody which specifically binds to normal intima and/or media is a monoclonal antibody produced by hybridoma Q10E7 (ATCC Accession No. HB 10188).

Imaging may be done through any of the methods known to one skilled in the art. These methods include but are not limited to X-ray, CAT scan, PET scan, NMRI, and fluoroscopy.

An alternative approach to removing plaque is by enzyme digestion. The subject invention provides a reagent for use in digesting atherosclerotic plaque which comprises an antibody which binds specifically to atherosclerotic plaque bound to an enzyme capable of digesting a component of atherosclerotic plaque. One such reagent comprises the monoclonal antibody produced by hybridoma Z2D3 or Z2D3/3E5 or other daughter cell lines and another comprises the 15H5 or 17H3 monoclonal antibody.

Another such reagent comprises the chimeric antibody described above or a fragment thereof comprising the recombinant polypeptide which comprises an amino acid sequence which is substantially the same as the amino acid sequence of the hypervariable region of the monoclonal antibody produced by hybridoma Z2D3 or by Z2D3/3E5. Further, the antibody may comprise the amino acid sequences of a human framework region and of a constant region from a human antibody. Such chimeric antibody may be a genetically engineered hybrid neomolecule conjugated to the enzyme or to the proenzyme, such that the neomolecule is partially an antibody and partially an enzyme. The chimeric antibody may also be a bifunctional antibody. The bifunctional antibody is usually produced by a quadroma. In a preferred embodiment, the quadroma is derived from the fusion of a hybridoma cell line Z2D3 or Z2D3/3E5 and a hybridoma secreting a monoclonal antibody binding an enzyme.

The enzyme may be any enzyme capable of digesting a component of the plaque. In a preferred embodiment, the enzyme is a proteinase, an elastase, a collagenase, or a saccharidase. In a particularly preferred embodiment, the enzyme is fibroblastic collagenase, gelatinase, polymorphonuclear collagenese, granolocytic collagenase, stromelysin I, stromelysin II, or elastase.

The subject invention also provides a composition comprising an amount of the above-described reagent effective to digest a component of atherosclerotic plaque and a physiologically acceptable carrier.

The subject invention provides a method for reducing the amount of atherosclerotic plaque in a blood vessel which comprises contacting the atherosclerotic plaque with the reagent for digesting atherosclerotic plaque described above, under conditions and in an amount such that the reagent binds to and digests, a component of plaque.

The subject invention also provides a method for reducing the amount of atherosclerotic plaque in a blood vessel which comprises: a) contacting normal lumen with an antibody which specifically binds to normal intima and/or media and has bound thereto an inhibitor of an enzyme under conditions such that the antibody binds to normal intima and/or media; and b) contacting the atherosclerotic plaque with the reagent for digesting atherosclerotic plaque under conditions such that the reagent binds to the atherosclerotic plaque. The antibody which specifically binds to normal intima and/or media is provided in a reagent for use in protecting normal arterial tissue from an enzyme capable of digestion of atherosclerotic plaque. Such reagent, which is bound to an inhibitor of an enzyme capable of digesting atherosclerotic plaque, comprises an antibody which binds an antigen synthesized or present in such normal tissue, such as the monoclonal antibody produced by hybridoma Q10E7, as well as a recombinant polypeptide which comprises an amino acid sequence which is substantially the same as the amino acid sequence of the hypervariable region of the monoclonal antibody produced by hybridoma Q10E7, or a chimeric or humanized antibody or fragment thereof comprising the recombinant polypeptide.

This invention further provides a method for reducing the amount of atherosclerotic plaque in a blood vessel which comprises: a) contacting the atherosclerotic plaque with a reagent under conditions such that the reagent binds to the plaque so as to form a reagent-plaque complex, which reagent is capable of specifically binding to both the plaque and to a proenzyme which, when cleaved, is converted into an enzyme whose substrate is a connective tissue present in atherosclerotic plaque, and which enzyme is capable of dissolving a component of the plaque; b) contacting the reagent-plaque complex with the proenzyme to which the reagent specifically binds under conditions such that the proenzyme is bound to the reagent so as to form a proenzyme-reagent-plaque complex; and c) contacting the proenzyme-reagent-plaque complex with an agent which is capable of specifically cleaving the proenzyme so that the proenzyme is converted into the enzyme under conditions such that the enzyme digests the plaque.

The subject invention further provides a method for reducing the amount of atherosclerotic plaque in a blood vessel which comprises a) contacting the atherosclerotic plaque with a reagent such as the reagent described above for digesting atherosclerotic plaque under conditions such that the reagent binds to the plaque so as to form a reagent-plaque complex, which reagent is bound to both the plaque and to a proenzyme which, when cleaved, is converted into an enzyme whose substrate is a connective tissue present in atherosclerotic plaque, and which enzyme is capable of dissolving a component of the plaque; and b) contacting the proenzyme-reagent-plaque complex with an agent which is capable of specifically cleaving the proenzyme so that the proenzyme is converted into the enzyme under conditions such that the enzyme digests the plaque.

In a preferred embodiment the reagent is a bifunctional antibody. The bifunctional antibody may be produced by any method known in the art including chemical linkage of fragments, and recombinant genetic engineering. In a presently preferred embodiment, the bifunctional antibody is produced by a quadroma, wherein the quadroma is derived from the fusion of a hybridoma cell line comprising the monoclonal antibody produced by hybridoma Z2D3 or Z2D3/3E5 or related cell line and a hybridoma secreting a monoclonal antibody binding an enzyme. To digest the plaque efficiently, it is preferred that the proenzyme be a proenzyme of granulocytic collagenase, fibroblastic collagenase, or stromelysin. It is preferred that the agent of step (c) is plasmin. The plasmin may be obtained by treating the subject with tissue plasminogen activator under such conditions so as to cleave plasminogen into plasmin.

Turning now to radiant energy treatment of atherosclerotic plaque, the subject invention provides a reagent for use in ablating atherosclerotic plaque which comprises an antibody which specifically binds to atherosclerotic plaque bound to a chromophore capable of absorbing radiation having a plaque ablating wavelength.

In one embodiment of this method the antibody is a monoclonal antibody such as that produced by hybridoma 15H5 or 17H3 and more preferably, the monoclonal antibody is produced by hybridoma Z2D3 or hybridoma Z2D3/3E5 or related daughter cell line. In another embodiment the chromophore absorbs light having a wavelength of from about 190 nm to about 1100 nm. Such chromophores are well known in the art. Accordingly, the choice of chromophore is readily determinable to one skilled in the art although a preferred embodiment is wherein the chromophore is fluorescein, rhodamine, tetracycline, or hematoporphyrin.

The subject invention further provides a composition comprising an amount of the above-described reagent effective for use in ablating atherosclerotic plaque and a physiologically acceptable carrier.

This invention provides a method for ablating atherosclerotic plaque which comprises: a) contacting atherosclerotic plaque with an effective amount of the reagent for use in ablating atherosclerotic plaque described hereinabove so that the reagent binds to the atherosclerotic plaque forming an atherosclerotic plaque-reagent complex; b) exposing the resulting complex to radiation having a plaque ablating wavelength under conditions such that the light is absorbed by the chromophore at a sufficient energy to ablate the atherosclerotic plaque.

The subject invention further provides a method for ablating atherosclerotic plaque present in a blood vessel which comprises: a) contacting the normal lumen with an antibody which specifically binds to normal intima and/or media and has bound thereto a moiety capable of reflecting radiation of the plaque ablating wavelength; b) contacting the atherosclerotic plaque with the reagent for use in ablating atherosclerotic plaque described hereinabove under conditions such that the reagent binds to the atherosclerotic plaque; and c) exposing the atherosclerotic plaque to radiation having plaque ablating wavelength, thereby ablating the plaque.

In a preferred embodiment of this method, the antibody which specifically binds to normal intima and/or media is a monoclonal antibody produced by hybridoma Q10E7 (ATCC Accession No. HB 10188).

The choice of moiety for reflecting light is readily determinable to one skilled in the art.

The subject invention also provides a reagent for use in treating atherosclerosis which comprises an antibody which binds specifically to atherosclerotic plaque bound to drug useful in treating atherosclerosis. In a preferred embodiment the antibody is the monoclonal antibody produced by hybridoma Z2D3 (ATCC Accession No. HB9840). These reagents can be used in a method of treating atherosclerosis in a subject which comprises administering to the subject an amount of such reagent effective to treat atherosclerosis.

Further, the subject invention provides a method of treating atherosclerosis in a subject which comprises a) administering to the subject an antibody which specifically binds to normal intima and/or media and which has bound thereto an inhibitor of a drug useful in treating atherosclerosis; and b) administering to the subject an amount of the reagent described above effective to treat atherosclerosis. In a preferred embodiment of this method, the antibody for use in protecting normal arterial tissue from a drug useful in treating atherosclerosis is a monoclonal antibody produced by hybridoma Q10E7 (ATCC Accession No. HB 10188) which has bound thereto an inhibitor of a drug useful in treating atherosclerosis.

The subject invention provides a method of treating atherosclerosis which comprises blocking the synthesis of an atherosclerotic plaque specific antigen. The blocking of the atherosclerotic plaque antigen may be accomplished in several ways. One embodiment of this method is wherein the synthesis of the antigen is blocked by using an antisense nucleic acid which specifically binds to a nucleic acid encoding the antigen, the expression of which is associated with synthesis of the antigen.. In another embodiment of this method the synthesis of the antigen is blocked by inhibiting an enzyme involved in the synthesis of the antigen.

The subject invention also provides a method of treating atherosclerosis which comprises blocking the binding of an antibody, such as an auto-antibody to the atherosclerotic antibody plaque antigen.

This method may encompass any of the methods known to one skilled in the art. One embodiment of this method comprises blocking the binding of the auto-antibody to the antigen by contacting the antigen with an excess of antibody. Another embodiment of this method comprises blocking the binding of the auto-antibody to the antigen by contacting the auto-antibody with an excess of an anti-idiotype antibody made thereto.

Figure 23:
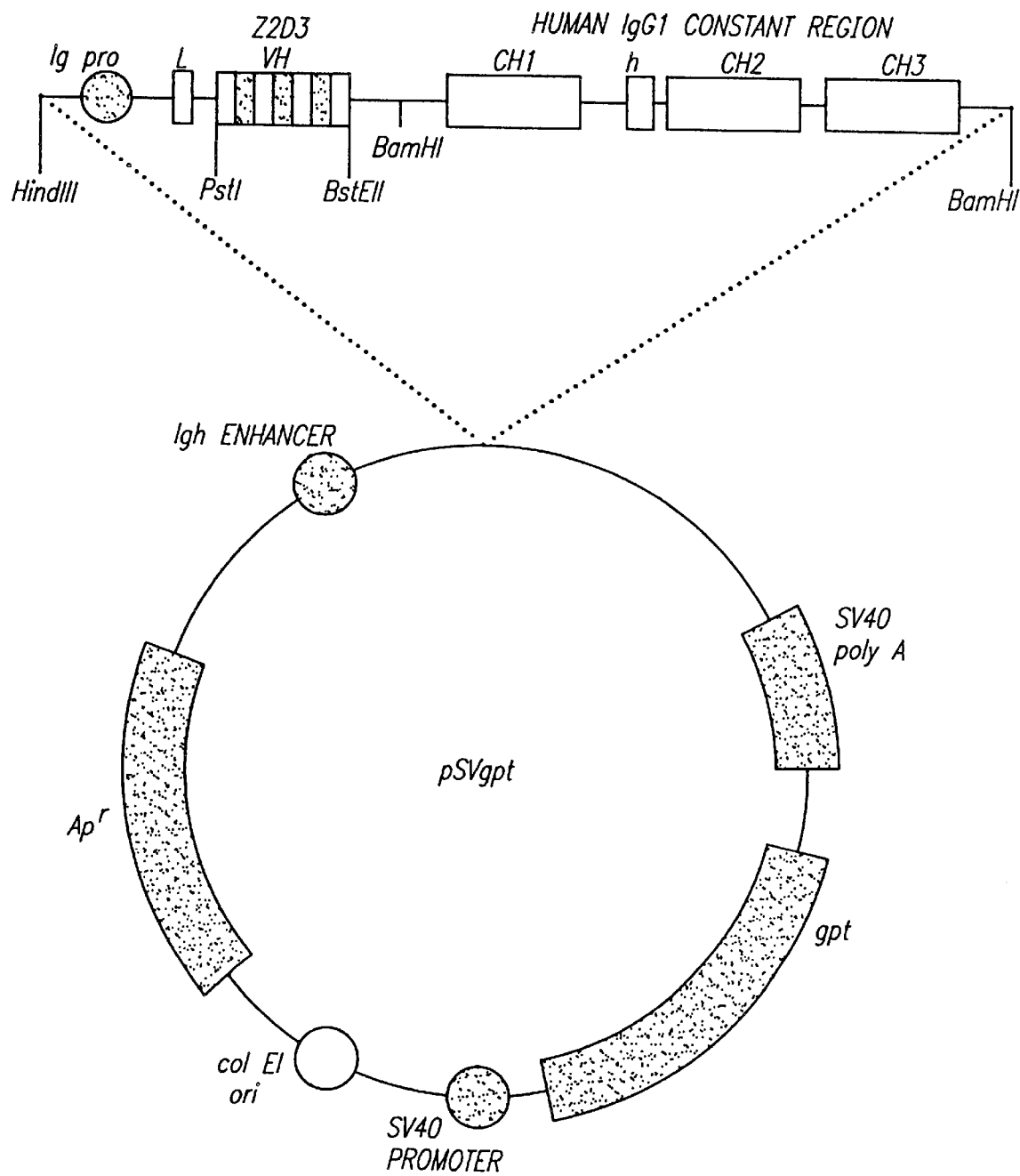
FIG. 23—Graph of body mass index (BMI) against IgG+A. Values in each compartment are marked at the 98th percentile, so that 98 percent of subjects in such compartment are below the marked threshold. If a subject is above the threshold, such subject may be predisposed to atherosclerosis.
Figure 24:
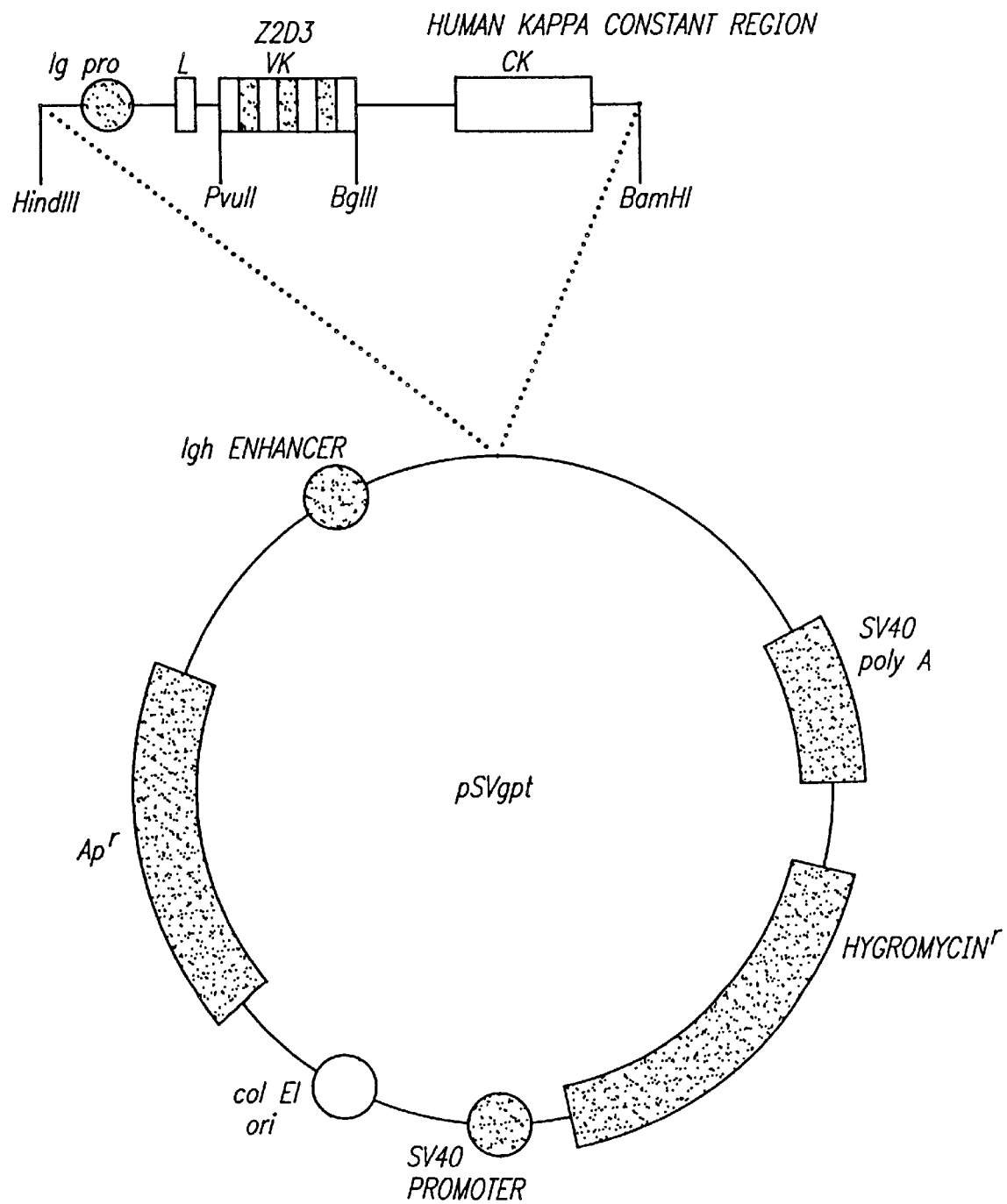
FIG. 24—Graph of body mass index (BMI) against antigen. Values in each compartment are marked at the 100th percentile, so that 100 percent of subjects in such compartment are below the marked threshold. If a subject is above the threshold, such subject may be predisposed to atherosclerosis.

The subject invention further provides a method for diagnostic analysis comprising the steps of: a) obtaining a value for the body mass index (BMI) of a patient; b) obtaining a value for the concentration of an antigen or other serum or plasma analytes associated with a pathological condition or an antibody which binds with the antigen; c) plotting the body mass index of the patient against the antigen or antibody concentration of the same patient; and d) comparing the resulting value against a set of reference values to determine whether the resulting value exceeds the reference value and thereby indicates the presence of a pathological condition. This method is a generic method may be used instead of conventional methods which just reveal positive or negative results in testing whether a patient has a predisposition toward such pathological conditions as cancer and atherosclerosis. In determining whether a patient has a predisposition toward atherosclerosis, the method is preferable used wherein the antigen is an antigen synthesized by, or present in, atherosclerotic plaque (FIG. 24), or wherein the antibody is an antibody which specifically binds to such an antigen (FIG. 23). The body mass index (BMI) is obtained by dividing a subject's weight by their height$^2$.

Experimental Detail

The Experimental Detail section is arranged as follows:
I. PREPARATION OF ATHEROSCLEROTIC PLAQUE ANTIGENS
II. CHARACTERIZATION OF ATHEROSCLEROTIC PLAQUE ANTIGENS
III. PROCEDURES FOR ANTIBODY ISOLATION AND PREPARATION
IV. PROCEDURES FOR IMMUNOASSAYS
V. PROCEDURES FOR ANTIBODY LABELING
VI. PROCEDURES FOR IMAGING ATHEROSCLEROTIC PLAQUE
VII. PROCEDURES FOR HISTOLOGY
VIII. METHODS OF TREATING ATHEROSCLEROTIC PLAQUE

I. PREPARATION OF THE ATHEROSCLEROTIC PLAQUE ANTIGENS

Purification of PBS Extracted Atherosclerotic Plaque Antigen
(Solubilization)

Tissue handling and antigen solubilization were done as described below:
1. Obtain atherosclerotic arteries from human autopsy within 24 hours of death or from surgical procedures.
2. Remove sample and wash in multiple changes of 20 mM phosphate buffer 0.15M NaCl/pH 7.3/0.02% NaN$_3$ (PBS) to remove blood components.
3. Freeze lesions at −80° C. until use.
4. When ready to process lesions, remove them from −80° C. freezer and let thaw at room temperature.
5. Rinse thawed lesions in cold PBS; carefully peel and retain atherosclerotic lesion from normal artery remnant. Discard artery remnant.
6. Weigh atherosclerotic lesions and record.
7. Using sharp, surgical scissors, cut lesions into 5×5 mm pieces. Keep them moist in cold PBS (enough solution to just cover fragments).
8. Homogenize lesion fragments in ice-cold PBS adding 5 ml of the cold PBS to 1 gram of lesion. (POLYTRON®; 2 to 4 minutes.)
9. Centrifuge homogenate at 10–15,000 RPM, 4° C. for 30 minutes. Retain supernate. Discard lipid layer.
10. Resuspend pellet in cold PBS (5 ml/gm) and re-homogenize.
11. Repeat step #9 and pool both supernates.
12. Aliquot and freeze plaque supernate at −80° C. unless remainder of purification is then carried out.

(Affinity Purification)

Crude or partially purified plaque or serum antigen was mixed with 15H5 antibody coupled resin for 2 hrs. at room temperature (R.T.) [batch method] or applied to a column of resin at a flow rate of about 1 ml/min., the run-through was reapplied to the same column [column method]. All samples and resins were equilibrated with 10 mM NaPO$_4$/150 mM NaCl/pH 7.2 (PBS).

After sample loading, the resin was then washed extensively with PBS and the bound antigen was then released by the addition of 0.1M glycine at pH 2.5 or 3.5M NaSCN in PBS. Fractions were collected, dialyzed in PBS at 4° C., tested for antigen reactivity by ELISA, and appropriate tubes pooled and stored for subsequent characterization.

Preparation of Monoclonal Antibody Affinity Chromatography Matrix

Mouse ascites containing monoclonal antibody 15H5 or Z2D3 were passed through a 0.45μ filter and then fractionated by HPLC gel filtration. Ten mls of ascites fluid was applied to a BIO-GEL® TSK-400 Column (600×21.5 mm, Bio-Rad) and eluted in 0.1M potassium phosphate pH 7.0. Fractions, of appropriate size to IgM, were pooled. Coupling of antibody to AFFI-GEL® resin (Bio-Rad) was done in the presence of 0.1M $KPO_4$ buffer at pH 7 with 1 mg antibody/1 ml packed gel. Gel preparation, antibody coupling (4 hrs. at R.T.) washing, and blocking with ethanolamine were done as per manufacturer's specifications.

Affinity Purification of Antigen From Positive Serum/Plasma

The following method is a one-step procedure for antigen affinity purification by means of 15H5 Ab gel:

1. 15H5 Ab Gel, 7.5 ml, is suspended with 10 mM PBS pH 7.0, 32.5 ml. Final volume is 40 ml. Dispense 80 μl of strong positive serum or plasma as determined by Antigen Capture Assay into 40 ml 15H5 antibody gel.
2. Gently mix on shaker at R.T. for 4 hrs. and then continuously mix it at 4° C. overnight.
3. Centrifuge at 3000 R.P.M for 10 minutes. Discard supernatant. The 15H5 Ab gel is washed with 10 mM PBS pH 7.0 (40 ml/time) for three times.
4. Add 20 ml 0.1M Glycine HCl, pH 2.5, into 15H5 antibody gel and mix well on shaker at R.T. for two minutes in order to disassociate antigen from 15H5 Ab gel.
5. Centrifuge at 3000 RPM for 10 minutes. Collect supernatant and immediately neutralize it with 2 ml of 1.0M Tris HCl pH 8.25 buffer.
6. Purified Ag solution is dialyzed against 10 mM PBS, pH 7.0, at 4° C. overnight (change buffer once).

Purification of Z2D3 and Q10E7 Antigens
Homogenization of Atherosclerotic Plaque
Method 1:

We report the isolation and characterization of a specific extracellular antigen found in the atherosclerotic plaques of humans, monkeys, pigs, and rabbits.

The plaque-matrix-specific antigen (Z2D3 Ag) was discovered when its identifying monoclonal antibody, Z2D3, was screened positive by immunohistology on atherosclerotic human coronary arteries. The Z2D3 antibody stained the plaque matrix without staining normal artery. The immunogen used in the hybridoma program that produced this antibody was affinity-purified material obtained from homogenized human plaque using the monoclonal antibody 15H5. The 15H5 antibody recognizes the carbohydrate autoantigen produced by normal and plaque-derived smooth muscle cells (Lamaziere, J. M., et al. Atherosclerosis (Ireland) 74 (1–2): 115 (1988)).

The Z2D3 antibody was further screened on a variety of human tissues using 5μ unfixed frozen tissue sections (Calenoff, E., et al., unpublished results). The plaques of all diseased human coronary arteries and aortae stained positive. All normal tissues with the exception of spleen fibromyocytes and focal cell clusters of ovary and sebaceous glands failed to stain with this antibody (Table 7). The normal tissue staining was confined to the cytosol without extracellular manifestations. In contrast, the vast portion of staining within atherosclerotic plaque was extracellular, diffusely manifest throughout the connective tissue matrix in addition to staining the cytosol of the plaque smooth muscle cells. In fibrofatty lesions, areas of macrophage involvement stained less strongly than areas with only connective tissue and/or smooth muscle cell involvement. The macrophages themselves failed to stain with the Z2D3 antibody.

The Z2D3 antibody also stained the atherosclerotic plaques of macaque monkeys, Watanabe rabbits, New Zealand white rabbits, and hypercholesterolemic pigs (Freshly dissected tissues were washed in cold normal saline solution and snap frozen. Five μ sections were cryostat cut and applied onto gelatin-coated slides. No fixation was done. The ABC immunoperoxidase method was employed as per the manufacturer's instructions (Vector, Burlingame, Calif.)). In the case of the monkey tissues, several phases of lesion growth were studied. The plaques of the monkeys that had been maintained on a 2% cholesterol diet for a period exceeding one year stained with the Z2D3 antibody. More interesting, however, was the observation that beneath the early fatty streaks of monkeys that had been maintained on the cholesterol diet for only months, the Z2D3 antibody stained the cytoplasm and immediate pericellular regions of the medial smooth muscle cells located immediately beneath the elastic lamina of those areas of the artery wall that were thus involved. This appeared within the time sequence corresponding to the migration of both macrophages and lymphocytes to this early lesion (Rapacz, J., et al. Science 234: 1573 (1986)). Slightly later in time, the smooth muscle cells were seen to penetrate the elastic lamina and migrate into the fatty streak area.

All attempts at isolating and purifying the Z2D3 plaque antigen under aqueous conditions were generally unsuccessful. The observation that organic solvent fixation of the frozen tissue sections employed in immunohistochemistry resulted in a total loss of staining led the applicant toward organic solvent extractions of the antigen from plaque tissue (Masuda, J. and Ross, R., Arteriosclerosis 10(2): 164 and 178 (1990)).

The extracted antigen was further purified by a sequence of chromatographic steps that included gel sieve sizing, ion-exchange chromatography, and thin-layer chromatography. Fresh plaque was peeled away from normal artery remnant and washed in cold normal saline. The plaque was then cut into 2×4 mm fragments and freeze-dried into small flakes (to remove as much free water as possible). The flakes were embedded in O.C.T. medium (Miles Labs, Elkhart, Ind.), blocked, and snap frozen. The frozen tissue block was mounted in a tissue section cryostat and 5μ tissue sections were cut. The tissue sections were mixed with 10 parts acetonitrile in a glass beaker. The glass beaker was tightly covered and the contents stirred vigorously for 18–24 hours at room temperature. The stirred contents were then centrifuged at 20,000 g, 4° C. for 1 hour and the precipitate discarded. The acetonitrile solution was filtered through a 0.22μ nylon filter (Millipore, Bedford, Mass.) yielding pale, yellow colored supernatant.

An ELISA immunoassay was utilized to determine the various chromatographic fractions for antigen content.

Gel Sieve Chromatography

The acetonitrile in the antigen solution was evaporated and the remaining residue redissolved in 100% ethanol. The pale, yellow solution was then mixed with 1 gram activated charcoal per 100 ml supernatant and the resulting slurry stirred for 1 hour at room temperature. The slurry was then filtered through the 0.22μ filter yielding a clear solution. This solution was then sized through a C26/100 column (Pharmacia, Piscataway, N.J.) packed with ethanol-equilibrated lipophilic SEPHADEX® LH-60 (Sigma, St. Louis, Mo.). The antigen positive fractions were pooled.

Ion Exchange Chromatography

Ion-exchange chromatography was performed on a MONO Q® HPLC column (Pharmacia) as per the method of Mansson (J. E. Mansson, B. Rosengren, L. Svennerholm, J. Chromatography 322, 465 (1985)), substituting ethanol for methanol as the solvent of choice. The Z2D3 antigen passed through the HPLC column in the void volume, unbound.

Thin Layer Chromatography (TLC)

TLC was performed utilizing WHATMAN® LK2 Linear-K cellulose plates (Cat. #4825-620). The plates were cut in half yielding two 5×10 cm plates. The fraction containing the Z2D3 antigen was applied to the plate, 1–10 uL per lane, using a glass capillary tube. (Sample was applied in multiple 0.5 uL aliquots per lane, and dried each time with a hair dryer.) The loaded plate was then placed in a container containing the mobile phase (chloroform, methanol, glacial acetic acid and water in the volume ratios 25:15:4:2) When the mobile phase was approximately 3 mm from the top of the plate, the plate was removed and allowed to air dry at ambient temperature. The plates from various TLC runs were stained individually with iodine staining or immunoperoxidase staining employing the Z2D3 antibody. The iodine staining was done by placing iodine crystals in a covered glass container and then incubated for 10–30 min. at 37° C. to produce the iodine vapor. The dry TLC plate was placed in the container. When the iodine reactive spots reached the desired degree of darkness, the plate was removed and inspected. A single spot at the upper edge of the mobile phase was observed. It was confirmed to be the Z2D3 antigen by running duplicate plates through an immunoperoxidase staining procedure employing the Z2D3 antibody and a negative control antibody.

Immunoperoxidase Detection of Z2D3 Antigen on TLC

Two dried TLC plates from above were blocked in a 0.2% casein/50 mM Tris-HCl/150 mM NaCl buffer (TBS), pH 7.6 for 45 min. One plate was then transferred to a 5 ug/mL solution of Z2D3 IgM MAb in the casein buffer and incubated for 18 hours at room temperature with gentle agitation. The other plate was incubated in the negative control antibody solution. Unbound antibody was removed by washing the plates for 15 minutes per wash ×3. The washed plates were then incubated in a 1:500 dilution of goat anti-mouse IgM/horse radish peroxidase conjugate (Tago, Burlingame, Calif.), for 3 hours with gentle agitation. The plates were then washed in casein buffer followed by 3 washes in TBS. The washed plates were then immersed in the substrate solution which consisted of 8 ml of 3 mg/mL 4-chloro-naphthol in methanol, 32 mL of TBS and 20 uL 30% $H_2O_2$. The plates were developed for 10–20 minutes and the reaction stopped by rinsing the plates with deionized water. A developed spot was seen at the mobile phase line on the Z2D3 plate but none on the non-specific antibody plate.

The Z2D3 antigen appears to be a small, lipid containing molecule. It is probably not a sphingolipid because of its resistance to the usual acid hydrolysis conditions but is perhaps a neutral lipid or a proteolipid. Various antigen fractions in either ethanol or other organic solvents were applied in 100 uL samples into the wells of IMMULON® 4 microtiter plates (Dynatech, Chantilly, Va.) and the organic solvents evaporated by blowing gently with bottled nitrogen gas or air. The dried plates were then blocked by applying 200 uL of the casein/TBS solution (wash buffer) for 1 hour. The plates were then washed 4× and 100 uL aliquots of 5 ug/mL Z2D3 antibody diluted in wash buffer applied to each test well. The plates were covered and incubated at 37° for 1 hour. They were washed 4× and 100 uL of goat anti-mouse IgM/peroxidase conjugate, diluted 1:100 applied. The plates were incubated for 1 hour at 37° and then washed. 100 ul of TMB substrate (Kirkegaard and Perry, Gaithersburg, Md.) was applied to each well and incubated for 1 hour at room temperature. 50 uL of 1M HCl was applied to each well to stop the substrate catalysis and the plates read at 450 nm on a Molecular Devices ELISA reader (Molecular Devices, Menlo Park, Calif.).

One benefit of having uncovered this antigen is its scientific utility in marking the altered smooth muscle cells which are directly responsible for the synthesis of these arterial lesions. From applicant's animal studies, it is obvious that the transition of the smooth muscle cells from normal to pathologic can be seen by immunohistologic means from the earliest phases of atherosclerosis to its end-stage.

The other benefit of having identified this molecular marker of atherosclerotic plaque is that it makes possible the development of novel diagnostic and therapeutic reagents for improving the clinical care of patients afflicted with coronary and/or cerebrovascular atherosclerosis. These take the form of imaging agents comprising Fab fragments labeled with radionuclides such as technetium to be used in nuclear imaging or those labeled with paramagnetic molecules to be used in MRI imaging. Targetable therapeutic reagents such as neomolecules could be constructed which possess antibody-like targeting and enzymatic activity which would yield a controlled catalysis and reduction of the connective tissue content in atherosclerotic plaque, thereby relieving focal arterial obstruction and preventing myocardial infarction and/or stroke (Kates, M., Techniques of Lipidology (Elsevier, N.Y., ed. 2, 1986)).

Method 2:

Tissue handling and antigen solubilization were done as described below:

1. Obtain atherosclerotic arteries from human autopsy with 24 hours of death.
2. Remove sample and wash in multiple changes of 20 mM PBS/0.15M NaCl/pH 7.3/0.2% $NaN_3$ (PBS) to remove blood components.

3. Freeze lesions at −80° C. until use.
4. When ready to process lesions, remove them from −80° C. freezer, and let thaw at room temperature.
5. Rinse thawed lesions in cold PBS; carefully peel and retain atherosclerotic lesion from normal artery remnant. Discard artery remnant.
6. Weigh atherosclerotic lesions and record.
7. Using sharp surgical scissors, cut lesions into 5×5 mm pieces. Keep them moist in room temperature (RT) 8M urea, adding 2 ml of the 8M urea to 1 gram of lesion. POLYTRON® 30 seconds.
8. Homogenize lesion fragments in RT 8M urea, adding 2 ml of the 8M urea to 1 gram of lesion. POLYTRON® 30 seconds.
9. Centrifuge homogenate at 15,000 RPM, 10–15° C. for 30 minutes. Retain supernate. Discard lipid layer.
10. Resuspend pellet in 8M urea (2 ml/gm) and re-homogenize for 30 seconds.

11. Repeat steps 9 and 10 as needed, and pool supernates.
12. Aliquot and freeze plaque supernate at −80° C. unless remainder of purification is then carried out.

Preparation of CsCl Gradient Fractionated Plaque Extract

1. Sample is made 3M CsCl by adding 0.5 gm CsCl per ml of 8M urea extract. Stir until CsCl is dissolved. This requires approximately 30 minutes. (Mixing is an endothermic reaction, and the 3M CsCl/sample may at first appear as a slush. Continue stirring until CsCl goes into solution).
2. Dispense 3M CsCl/sample solution into ultracentrifuge tubes, and cap. Be sure tubes are filled completely and sealed tight. Place tubes in TY70 rotor (Beckman).
3. Spin 50,000 rpm at 8° C. for 65 hours in Beckman ultracentrifuge.
4. At end of run, remove tubes from rotor and carefully pump out gradient solution from bottom of tubes using peristaltic pump. Collect equal fractions from each tube. Pool corresponding fractions. Fraction one is the bottom most fraction and fraction is the topmost fraction.
5. Store fractions at −80° C. until needed.

DEAE Ion Exchange Chromatography

1. Either CsCl fraction number one (Z2D3) or fraction number two (Q10E7) is/are dialyzed in 3500 MW tubing against 20 mM Tris-Hcl/7M Urea, pH 7.5, to achieve a 50,000× dialysis effect.
2. Determine O.D.$_{280}$ of sample.
3. Load sample on appropriate BIO-GEL® DEAE-5-PW HPLC columns (Bio-Rad):
   Analytical column=1 mg protein load range
   Semi-prep column=10–150 mg protein load range
4. The eluting buffers are 20 mM Tris-HCl/7M Urea, pH 7.5 (A), and 20 mM Tris-HCl/7M Urea/1M NaCl, pH 7.5 (B).
5. The elution profiles programmed into HPLC are:

| Time | Flow (ml/min) | % A | % B | Gradient profile |
|---|---|---|---|---|
| ANALYTICAL COLUMN: | | | | |
| 0 | 1.0 | 100 | 0 | Linear |
| 5 | 1.0 | 100 | 0 | Linear |
| 35 | 1.0 | 50 | 50 | Linear |
| SEMI-PREP DEAE COLUMN: | | | | |
| 0 | 4.0 | 100 | 0 | Linear |
| 10 | 4.0 | 100 | 0 | Linear |
| 55 | 4.0 | 50 | 50 | Linear |

6. One ml fractions are collected the in analytical run and 4 ml fractions are collected in the semi-prep run.
7. 50 µL of each sample from each tube are diluted in 20 mM Tris-HCl/3.5M Urea, pH 7.5, and used to coat wells on microtiter plate corresponding to each tube collected. Plates are incubated overnight at RT.
8. Plates are tested by employing the ELISA procedure described herein for determining Z2D3 activity (CsCl fraction one) or Q10E7 activity (CsCl fraction four). See illustrations b and c.
9. Those tubes whose contents gave a positive ELISA signal for the antigen in question are pooled together.
10. This Z2D3 or Q10E7 antigen-containing mixture is dialyzed against 20 mM Tris-HCl/0.15M NaCl, pH 7.4, to remove the urea, using dialysis tubing with 3500 MW pores.

Affinity Chromatography

1. The antigen-containing mixture is added to agarose gel, coupled to Z2D3 or Q10E7 monoclonal antibody (depending on which antigen requires purification).
2. This agarose gel/antigen mixture is gently mixed in a shaker at 4° C. overnight.
3. The gel is then loaded onto an appropriately-sized glass column.
4. The gel is washed with 20 gel volumes of 20 mM Tris-HCl/0.15M NaCl, pH 7.4(Tris).
5. The antigen is eluted with 0.1M glycine HCl buffer, pH 2.5.
6. The eluted antigen is dialyzed against Tris buffer.

Gel Sizing

1. The affinity purified antigen is concentrated using an AMICON® concentrator with 10,000 MW filter.
2. The concentrated antigen is filtered using 0.45µ filter and loaded onto a BIO-SIL® TSK-400 column (Z2D3 antigen) or BIO-SIL® TSK-250 column (Q10E7 antigen) equilibrated with 0.1M potassium phosphate buffer, pH 7.0 (BIO-SIL® columns are sold by Bio-Rad).
3. The major macromolecules of Z2D3 antigen are eluted at greater than 200,000 MW from the BIO-SIL® TSK-400 column. The Q10E7 antigen is eluted from the BIO-SIL® TSK-250 column at greater than 150,000 MW.

II. CHARACTERIZATION OF ATHEROSCLEROTIC PLAQUE ANTIGENS

Binding Studies Using Lectins and commercial Antibodies

Affinity purified atherosclerotic plaque antigen was coated onto polystyrene microtiter plates (IMMUNLON® II). Sample was diluted in 100 mM NaPO$_4$/400 mM NaCl/pH 6.9 and 100 µl was applied to each well and then incubated overnight at 4° C.

Plates were blocked and then washed with PBS containing 0.1% TRITON® X-100 and 0.05% TWEEN®-20 (for lectin study) or casein buffer (for commercial antibody study). Biotinylated lectins (from Vector or Sigma) were diluted to a final concentration of 1–10 µg/ml and 100 µl applied to wells coated with athero-antigen for 2 hrs at 37° C. Bound lectins were detected using an Avidin-Peroxidase conjugate [ABC from Vector Labs]. Commercial polyclonal and monoclonal antibodies were diluted with casein buffer (1/100 to 1/2000) and incubated with coated antigen (prepared as above) for 2 hrs. at 37° C. Appropriate peroxidase conjugated second antibodies (Tago) were then applied to detect binding of commercial antibodies to the coated athero-antigen.

Solvent Extraction/Precipitations

[TCA]
Partially purified atherosclerotic plaque antigen in PBS buffer was brought to a final concentration of 5% (wt./vol.) of trichoroacetic acid (TCA), incubated on ice for 30 minutes and then centrifuged to separate acid soluble and insoluble fractions. The insoluble material was dispersed into PBS and tested for remaining antigen by ELISA. The TCA supernatant fraction was neutralized by addition of 1M Tris pH 9, dialyzed against PBS and then assayed by ELISA.

[Acetone]

One volume of partially purified atherosclerotic plaque antigen was mixed with nine volumes of ice cold acetone, mixed, left on ice for 30 minutes, and then centrifuged. The pellet was air dried, resuspended in its original volume of PBS and assayed by ELISA. The acetone supernatant was discarded.

[Chloroform]

One volume of partially purified atherosclerotic plaque antigen was mixed vigorously with one volume of chloroform, and centrifuged 5 minutes at 2000 RPM. The upper aqueous layer was removed and extracted again with chloroform. After a second centrifugation, the aqueous layer was assayed by ELISA.

Enzyme Digests of Atherosclerotic Plaque Antigen

Affinity purified atherosclerotic plaque antigen from plaque or serum was mixed with a wide array of hydrolytic enzymes, the specific reaction buffers were those suggested by the manufacturer. All reactions were done in a total volume of 1.0–1.5 ml, incubated overnight at 37°, then boiled for 5 minutes to stop the reaction. Samples were filtered (0.45μ) and injected onto an HPLC column (TSK-400 600 mm×7.5 mm BIO-RAD®) for molecular sieve fractionation in 0.1M $KPO_4$, pH 7.0. Individual fractions (25 drops each) were tested by ELISA in both antibody capture and coated antigen formats for changes in the elution profile of atherosclerotic plaque antigen relative to control (undigested) samples. Molecular weight standards [Bio-Rad: thyroglobulin, immunoglobulin, ovalbumin, myoglobin, and vitamin B-12] were used to calibrate the TSK-400 column elution.

Colorimetric Assays a) Total hexosamine was measured by the method of Blumenkrantz and Asboe-Hansen [lin. Biochem., 9:264 (1976)]. Briefly, antigen sample (0.4 ml) was mixed with 0.3 ml of 3.5% acetylacetone in phosphate/tetraboronate buffer and heated to 100° C. for 30 minutes. The mixture was cooled, 1 ml of Ehrlich's reagent was added, and the resulting absorbance (at 535 nm wave length) was measured. D (+) glucosamine was used as a standard.

b) Uronic acid was measured using the method of Blumenkrantz and Asboe-Hansen (Anal. Biochem., 54:484 (1973)]. Briefly, to 0.1 ml of antigen sample was added 0.6 ml of sulfuric acid/tetraboronate reagent followed by mixing and incubation at 100° C. for five minutes. After cooling, 0.01 ml of m-hydroxydiphenyl reagent was added, the tubes mixed, and after five minutes, absorbance at 520 nm was recorded. Chondroitin sulfate was used as a reference standard.

Molecular Charge Determination

Initial efforts to determine the isoelectric pH (pI) of the atherosclerotic plaque antigen ulilized mixed bed ion-exchange resin reagents chromatofocusing system from Pharmacia. Conditions used were as per manufacturer's instructions; antigen sample was dialyzed into high pH buffer (11.0) and 1 ml was applied to POLYBUFFER® Exchange 118 resin (10 ml bed). The elution gradient was then developed with a pH 8.0 buffer. The pH of individual fractions was measured, then they were dialyzed into PBS pH 7.2 and assayed by ELISA.

Additional ion exchange binding studies were done using QAE-Sepharose (anion exchanger) and S-SEPHAROSE® (cation exchanger) over a pH range of 7–12 according to the method of Lang and Langer [Anal. Biochem., 147:148 (1985)]. Briefly, partially purified antigen was dialyzed into 5 mM $NaPO_4$ buffer at pH 7, 8, 9, 10, 11, and 12. Aliquots of ion-exchange resin 0.5 ml packed gel equilibrated at the same pHs were mixed with 1 ml of antigen for 30 minutes at 25° C. The samples were centrifuged at 2000 RPM for 5 minutes, the supernatants removed and filtered to remove gel fragments, and then assayed by ELISA to quantitate unbound antigen. Cytochrome C and myoglobin were used as a high pI (10.2) standard and mid-range pI (7.4) standard, respectively, to validate the procedure.

Miscellaneous Treatments

[Chaotropes]

Atherosclerotic plaque antigen was exposed to the following list of denaturants and then returned to its original buffer [PBS] by dialysis.

Agents: 8M urea in PBS for 24 hrs. at R.T
6M Guanidine HCl in PBS for 24 hrs. at R.T.
2M Triflouroacetic acid for 30 minutes at R.T.
3.5M NaSCN in PBS for 8 hrs. at R.T.
0.1M Glycine pH 2.5 for 2 hrs. at R.T.
0.19 SDS in PBS for 1 hr. at R.T. (recover antigen by precipitation with acetone)

[Alkylation-Reduction]

Partially purified atherosclerotic plaque antigen (0.5 ml in 0.1M $KPO_4$, pH 7.0) was mixed with 0.44 guanidine-HCl (7M final concentration) and 250 μg of dithiothreitol. The pH was adjusted to 8.6 and the sample left for 1 hr. at R.T. Then 16 mg of iodoacetamide was slowly added and pH maintained at 8.5 with NaOH as needed. After 1 hr. at R.T. this sample was run on a TSK-400 HPLC gel filtration column (as described above) and individual fractions were tested for atherosclerotic plaque antigen by ELISA and compared to fractions collected from unreacted antigen.

Carbohydrate Analysis of Human Plasma Antigen and Controls

The following outline describes the procedures used for carbohydrate analysis of various polysaccharide hydrolates at Vasocor.

Antigen Purification:

Antigen and control samples were prepared by affinity chromatography. Affinity resins were prepared by coupling Vasocor monoclonal antibody 15H5 to BIO-RAD® AFFI-GEL® 10 using published methods.

Plasma samples were incubated with the resin in a batch-wise procedure. After washing, the bound antigen was eluted with 0.1M glycine buffer pH 2.5. The antigen solution was then neutralized and dialyzed against PBS.

Sample Preparation:

Salts were removed by extensive dialysis against purified water at 4° C. Each sample was concentrated by lyophilization and the residue redissolved in a minimal volume of purified water.

Standard Preparation:

Ultra high purity monosaccharide standards were obtained from Pfansteiehl Laboratories Inc., Waukegan, Ill. Standard solutions and dilutions thereof were all prepared in purified water. Aliquots of each standard were stored at −80° C. until use.

Hydrolysis:

Concentrated trifluoroacetic acid (Pierce, Rockford, Ill.) was added to the aqueous sample solution to a final concentration of 2M. The vial was flushed thoroughly with filtered nitrogen and capped with a thermostable, TEFLON®-lined cap. The vial was placed in a sand bath at 104±4° C. for four hours. After hydrolysis, the vial was cooled (10 minutes) and the solvents evaporated under a stream of filtered nitrogen.

Carbohydrate Analysis:

The DIONEX® instrument was expressly configured for monosaccharide analysis, consisting of a reagent delivery module, micro-injection valve, pulsed amperometric detector with gold electrode, and CarboPac PA-1 analytical column. Data were collected on a Dionex 4270 Integrator.

For each run, the column was thoroughly equilibrated in 15 mM NaOH in purified water. Hydrolysate residue were redissolved in purified water just prior to injection. The bound monosaccharides were eluted from the CarboPac column with a linear gradient of NaOH in purified water.

Results:

FIG. 20 illustrates a chromatographic blank run with just distilled water.

Figure 21A:
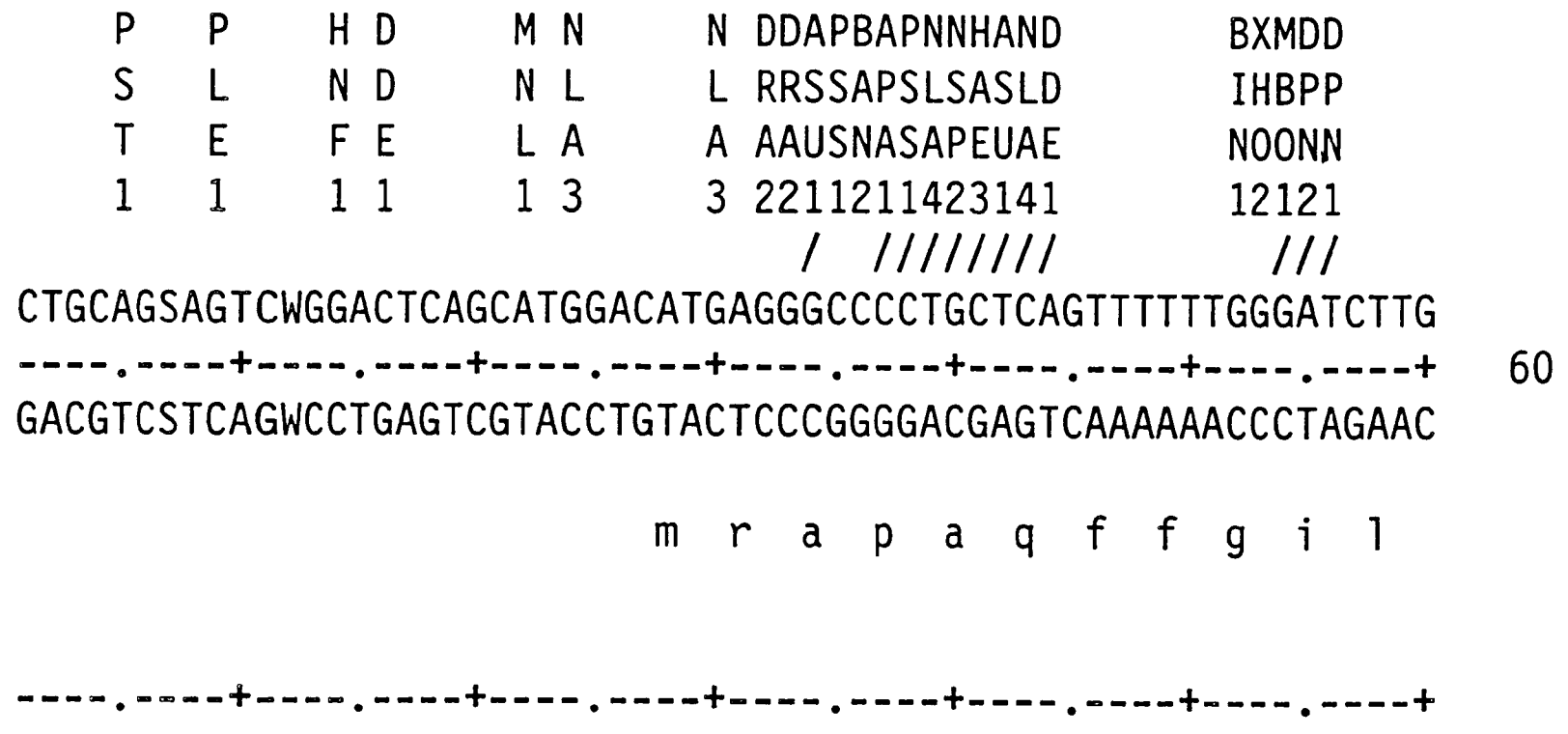

FIG. 21 illustrates a chromatographic run with seven standard monosaccharides.

FIG. 22 illustrates a chromatographic blank run with the auto-antigen affinity purification with the 15H5 monoclonal antibody.

III. PROCEDURES FOR ANTIBODY ISOLATION AND PREPARATION

Antibody Conjugation to Sepharose

Freeze-dried CNBr-SEPHAROSE® 4B powder (Pharmacia) is swelled for 15 min in 1 mM HCl. The gel is washed on a sintered glass filter (porosity G-3) with a total of 200 ml of 1 mM HCl per gram of gel (dry wt.) This is done in several aliquots, the supernatant being suctioned off between successive additions.

5 mg of protein to be coupled per 1 ml of gel is dissolved in Coupling Buffer (0.1M $NaHCO_3$, pH 8.3, containing 0.5M Nacl). The gel is washed with Coupling Buffer, the excess is removed by suction, and the protein solution is mixed with the gel. The mixture is allowed to stand overnight at 4° C. with stirring. The gel is then placed in a Blocking Buffer containing 1M ethanolamine, pH 8.0, for 2 hr at rm temp. The gel is then washed with the Coupling Buffer containing 1M ethanolamine, pH 8.0, for 2 hr at rm temp. The gel is then washed with the Coupling Buffer, 0.1M Acetate Buffer, pH 4.0, containing 0.5M NaCl, and washed twice with Coupling Buffer. The protein-SEPHAROSE® conjugate is now ready for use and can be stored at 4 to 8° C. Cyanogen bromide can be added to the buffer solution as a bacteriostat.

IgG Antibody Adsorption from Plague Supernatant

A column is packed with 25 ml of SEPHAROSE® gel conjugated to anti-IgG antibody prepared in accordance with the above procedure containing a total of about 129 mg of anti-IgG antibody. The column is equilibrated with from 2 to 3 volumes of buffer (0.15M PBS, pH 7.2), and the sample is then applied to the column.

The flow rate of eluting buffer (0.15M PBS, pH 7.2) is 125 ml/hr. The eluted fractions containing antibody are collected until peak activity disappears.

The column is then washed with sodium acetate buffer solution, pH 4.0 (Eluting Buffer) to desorb immunoaffinity bound IgG antibody. The column is eluted a rate of 15–20 ml/hr, collecting the eluted samples and retaining peak fractions. The peak fractions are dialyzed against 0.15M PBS, pH 7.2, for 24–36 hr at 4° C. with multiple buffer changes.

IgE Antibody Adsorption from Plague Supernatant

The above procedure is repeated with a column packed with 7.5 ml of SEPHAROSE® gel conjugated to anti-IgE antibody prepared as stated above. The flow rate of Eluting Buffer is 15–20 ml/hr.

IgA Antibody Adsorption from Plague Supernatant

The above procedure of is repeated with a column packed with 7.5 ml of SEPHAROSE® gel conjugated to anti-IgE antibody prepared in accordance with the procedure as stated above. The flow rate of Eluting Buffer is 15–20 ml/hr.

IgM Antibody Adsorption from Plague Supernatant

The above procedure is repeated with a column packed with 7.5 ml of SEPHAROSE® gel conjugated to anti-IgE antibody prepared in accordance with the procedure shown above. The flow rate of Eluting Buffer is 15–20 ml/hr.

Polyclonal Anti-Plaque Antibodies

Polyclonal antiserum against atheroslerotic plaque antigen is elicited in rabbits using the immunization techniques and schedules described in the literature, e.g. [Stollar, Methods of Enzymology, 70:70 (1980)]. The antiserum is then screened in a solid phase assay similar to that used for monoclonal antibodies, e.g. [Lange et al., Clin. Exp. Immunol., 25:191 (1976) and Pisetsky et al., J. Immun. Methods. 41:187 (1981).] The initial screening criterion would be binding to atherosclerotic plaque antigen.

Polyclonal anti-plaque antibody must be prepared as follows: Rabbits may be injected intramuscularly with a mixture of 0.5 mg of plaque antigen prepared by the procedure described hereinabove in 0.2 ml of 0.15M sodium chloride solution and 0.8 ml of complete Freund's adjuvant. The immunization is repeated for 14 days and then each week for 3 weeks. After a further 10 days have passed, blood is removed from the rabbits, and antiserum is recovered from the blood by allowing it to coagulate and removing the clot.

Repeating the above procedure but replacing the antibody reagent with the plaque antigen yields horseradish peroxidase or alkaline phosphatase-labeled plaque antigen.

The IgG fraction of the antisera is purified further by affinity chromatography on a column containing a resin on which the anti-plaque antigen is immobilized.

Monoclonal Anti-Plaque Antibody

Using the purified atherosclerotic plaque antigen, mouse monoclonal antibodies to the plaque antigen are obtained using standard procedures of Galfre and Milstein, [Methods in Enzym., 73:1 (1981)]. The monoclonal antibodies are screened using a modification of the techniques described in the literature, e.g., [Lange et al., Clin. Exp. Immuno., 25:191 (1976)] and Pisetsky et al. [J. Immun. Methods., 41:187 (1981)].

To be useful for the assay of serum plaque antigen (or immunocomplexes thereof), a monoclonal antibody should bind to the plaque antigen with high affinity (preferably, $K_A$ $10^{10} M^{-1}$).

Mouse monoclonal antibody is purified in a two step procedure. The neat ascites fluid is applied to a column of AFFI-GEL® Blue resin (Bio-Rad Laboratories, Richmond, Calif.) equilibrated with 10 mM Tris-HCl, 0.15M NaCl, pH 8.0, and eluted with the buffer. This step removes albumin, which is retained on the column. The final step in the purification is application to a DEAE-SEPHAROSE® (Pharmacia Fine Chemicals, Piscataway, N.J.) and elution with a linear gradient of 10 mM Tris-HCl, pH 8.0, to 10 mM Tris-HCl, 100 mM NaCl. This gives purified mouse monoclonal antibody free from contaminating serum proteins such as albumin and transferrin.

Successful Isolation of a Class Switch Variant Within the Hybridoma Cell Line Z2D3

The class switch was from an IgM isotype cell line Z2D3 (ATCC Accession No. 9840) with specificity for atherosclerosis plaque antigen, to an IgG isotype cell line (Z2D3/5C5) with the same specificity. Z2D315C5 is an example of several daughter cell lines of Z2D3. Such daughter cell lines also include Z2D3/3E5 (ATCC Accession No. HB 10485).

The IgM isotype Z2D3 hybridoma cell line was prepared by fusing Balb/c splenocytes with the SP2 Myeloma cell line. (See Journal of Immunology, Vol. 131 No. 2 August 1983. Isolation of Immunoglobulin Class with Variants from Hybridoma lines secreting Anti-Idiotype Antibodies by sequential sublining. Christa E. Muller and Klaus Rajewsky; Journal of Immunology Methods, Vol. 74, 1984, pg. 307–315. The Identification of Monoclonal Class Switch Variants by Sib Selection and an ELISA Assay, Gad Spira, Autonio Bargellesi, Jean-Luc Teilland, Matthew D. Scharff.)

Z2D3 was screened initially for IgG producing cells. 100 cells were plated/well in 96 well FALCON® plates for a total of 10 plates. At day 8 supernatants were collected and tested for IgG. 96 wells were coated overnight at 4° C. with 50 ng/well of goat anti-mouse IgG. ($\gamma$ chain specific) reagent Zymed 62-6600). Wells were washed ×4 with PBS with 0.05% Tween (wash buffer), and 50 $\mu$l of supernatant from the plated cells was added. After incubating two-to three hours at room temperature, plates were washed ×4 with the wash buffer and 50 $\mu$l ⅟1000 dilution of the Alkaline Phosphatase conjugated—Goat anti-mouse IgG ($\gamma$ chain specific) reagent added. (Zymed 62 - 6622). After two hours incubation at room temperature, plates were washed ×4 with the wash buffer and 100 $\mu$l of four-methylumbelliferyl phosphate substrate solution (Sigma No. M8883) was added to each well. After 60 minutes at room temperature, the plates were read using a Fluorofast 96 well Fluorometer. (3M Diagnostics, Santa Clara, Calif.).

The sensitivity of the assay enabled one positive cell in 100 to be detected easily. Initially 3 positive wells were detected. The well (8G2) producing the highest signal was further enriched by subcloning as follows:

This positive well was then resuspended in 100 ml of medium containing 9% Fetal Calf Serum, and plated in 5, 96-well plates at 200 $\mu$l/well. Supernatants from these wells were tested as above 8 days later, and 70% of the wells were positive for IgG. The well (1A12) with the highest signal for IgG was chosen for additional subcloning. Cells in the well were suspended by pipetting and 20 $\mu$l of the suspension was diluted into 100 ml of medium with 9% Fetal Calf Serum. The suspension was plated 200 $\mu$l/well in 5 plates, with approximately 3 cells/well.

After 8 days the supernatants were tested for IgM and IgG using the protocol described above but using a Goat anti IgM ($\mu$ chain specific) reagent (Tago. 4142) to coat the wells 50 ng/well overnight and Goat anti-IgM ($\mu$ chain specific) reagent (Tago 4652) as the Alkaline phosphatase conjugate, for the assay to detect IgM. The three with the highest IgG Signal were retested by doing dilution curves to more accurately determine amounts of $\mu$ and $\gamma$ chains. 7D10 had the highest $\gamma$ and the lowest $\mu$. This well (7D10) was then subcloned at 0.5 cells/well in 6 plates for the final derivation of a cloned line.

Single clones were identified visually and tested with IgM and IgG reagents. Several $\gamma$ producing clones were chosen, of which 5C5 was further grown and studied. This clone is designated Z2D3/5C5.

Supernatants from the $\mu$-producing Z2D3 cloned line and the $\gamma$-producing Z2D3/5C5 clonal line show identical specificity as tested by the following:

1. Z2D3 IgM and Z2D3/5C5 IgG, when used in Immunohistological staining of frozen sections of human and rabbit atherosclerotic plaque show identical histological localization, and on normal tissue give identical negative results.
2. When tested (ELISA) for binding to antigen (alcohol extracted from human atherosclerotic plaque) both antibodies bind specifically, whereas other antibodies of the same classes give negative results.

The IgG class was confirmed and the subclass determined using a SubIsotyping Kit (Hyclone E05051-K). Z2D3/5C5 is IgG1.

IV. PROCEDURES FOR IMMTUNOASSAYS

Antibody Assay Procedure

1. Add 10 $\mu$l sample or control (positive and negative) into 2 ml sample diluent in glass tubes.
2. Incubate at 4° C. overnight.
3. The following morning take antigen-coated plate and aspirate antigen coating solution out of each well. Then add 200 $\mu$l 0.2% casein buffer into each well to block wells at R.T. for 30 minutes. After that, aspirate and wash with 0.2% casein buffer once.
4. Apply 100 $\mu$l sample or control into each well according to prepared plate map (sample or control run duplicate).
5. Cover plate with PARAFILM® and incubate at R.T. for two hrs.
6. Aspirate and wash plate with 0.2% casein buffer three times.
7. Add 100 $\mu$l working dilution of anti-human IgG conjugate or anti-human IgA conjugate anti-human IgA conjugate into each well. Incubate at R.T. for 2 hrs.
8. Wash plate with 0.2% casein buffer four times.
9. Prepare TMB substrate (using equal volumes mix TMB substrate with peroidase solution B).
10. Add 100 $\mu$l substrate into each well and react at R.T. for 60 minutes.
11. Read plate at 650 nm on ELISA reader first, and then add 50 $\mu$l 1M HCl into each well to stop reaction. After that, read plate at 450 nm again.
12. The optical density (O.D.) number is directly proportional to the concentration of antibody in tested sample.

Antigen Capture Assay Procedure

1. Add 250 $\mu$l sample or control (positive or negative) into 250 $\mu$l sample diluent in glass tube.

2. Incubate above mixture at 37° C. for four hrs.
3. Aspirate buffer from 15H5 Ab-coated plate (200 μl/well) and wash plate with 100 mM PBS/Tween/Triton buffer once.
4. Apply 200 μl sample or control into each well according to prepared plate map (sample or control run duplicate).
5. Cover plate with PARAFILM® and incubate at R.T. overnight.
6. The following morning, aspirate samples out of wells. Wash plate with 0.2% casein buffer three times.
7. Add 200 μl working dilution of 17H3 Ab-peroxidase conjugate into each well.
8. Cover plate with PARAFILM® and incubate at 37° C. for four hrs.
9. Wash plate with 0.2% casein buffer four times.
10. Prepare TMB substrate (using equal volumes mix TMB substrate with peroxidase solution B).
11. Add 200 μl substrate into each well and react at R.T. for 60 minutes.
12. Read plate at 650 nm on ELISA Reader first, and then add 50 μl 1M HCl into each well to stop reaction. After that, read plate at 450 nm again.
13. The optical density (O.D.) number is directly proportional to the concentration of antigen in the tested sample.

Inhibition Assay Protocol

1. Apply 100 μl different concentration of HCAD or in-house monoclonal antibody (17H3 Ab., Z2D3 Ab., 15H5 Ab., and normal mouse IgM as a mono Ab. control into antigen-coated wells in order to pre-block wells. At the same time, add 100 μl 10 mM PBS buffer into antigen-coated wells as a noninhibition control). The plate is covered with PARAFILM®.
2. Incubate plate at R.T. for two hrs., and then at 4° C. overnight.
3. The following morning, aspirate each well and wash with 0.2% casein buffer three times.
4. Add 100 μl of optimal concentration of each monoclonal antibody into each HCAD pre-blocked wells, or 100 μl of optimal dilution of HCAD into each monocloanl pre-blocked wells. The plate is covered with PARAFILM®.
5. Incubate at R.T. for two hrs.
6. Aspirate and was with 0.2% casein buffer four times.
7. Add 100 μl conjugate (1:2 K goat anti-mouse Igm peroxidase conjugate for HCAD pre-blocked wells and 1:400 mouse anti-HuIgG-peroxidase conjugate for monoclonal preblocked wells) into each well including PBS control wells. Cover the plate with PARAFILM®.
8. Incubate at R.T.1 for two hrs.
9. Aspirate and wash with 0.2% casein buffer four times.
10. Add 100 μl TMB substrate into each well. React at R.T. for one hr.
11. Read plate at 650 nm and then add 50 μl 1.0M HCLO stop solution into each well, read plate at 450 nm again.

12. Calculation:

$$\text{Inhibition\%} = 100\% - \frac{\text{Assay well mean O.D.}}{\text{control well Mean O.D.}} \times 100\% \text{ PBS}$$

Immunoassay Procedure for Atherosclerotic Plaque Antigens

To each microtiter plate coated with anti-plaque antibody, 90 microliters/well of the serum sample of the patient being tested, mixed with 10 microliters/well of noraml mouse serum, is applied. The plates are covered to prevent drying and incubated overnight. The sera mixture is removed, and the plate is washed 3 times with casein wash buffer.

100 microliters/well of horseradish peroxidase conjugated antibody or alkaline phosphatase conjugated anti-plaque antibody prepared in accordance with the procedure described hereinabove is applied to each well, and the plates are covered to prevent drying and incubated for 2 hours. The enzyme labeled antibody solution is removed, and the plates are washed 4 times with casein wash buffer.

100 Microliters/well of either tetramethylbenzidine, in the case of horseradish peroxidase, or 4-methylumbelliferyl phosphate solution (3M Diagnostics Systems), in the case of alkaline phosphatase, is then applied to the well. The microtiter plates are then read in either a calorimetric reader (Molecular Devices) or a fluorometer (3M Diagnostics) every 10 minutes until the the maximum reading or 1 hour is reached.

Immunoassay Procedure for Antibodies which Bind Specifically to Atherosclerotic Plaque To each microtiter plate coated with atherosclerotic plaque antigen, 100 microliters/well of human serum is applied (Sample may be diluted). The plates are covered to prevent drying and incubated for 2 hours, and the residual solution is removed, and the plates washed three times with casein wash buffer.

100 Microliters/well of a solution of affinity purified goat anti-IgG, IgM, IgA, or IgE conjugated to either horseradish peroxidase or alkaline phosphatase (appropriately diluted) is applied to each well. The plates are covered to prevent drying and incubated for 2 hrs. The anti-IgG, IgM, IgA, or IgE solution is removed and the plates washed three times with casein wash buffer.

100 Microliters/well of either a tetramethyl benzidine solution, in the case of a horseradish peroxidase conjugated antibody, or a 4-methylumbelliferyl phosphate solution (3M Diagnostic Systems), in the case of an alkaline phosphatase conjugated antibody, is then applied to the well. The microtiter plates are then read in a calorimetric reader (Molecular Devices) or a fluorometer (3M Diagnostics) every 10 minutes until the first maximum reading or 1 hr is reached.

Plaque Antigen Coated Microtiter Plate Preparation

100 Microliters of prepared dilutions of plaque antigen are applied to the surface of IMMULON® II microtiter plates (Dynatech). The coating solution dilutions are 1:10, 1:100, 1:1000 and 1:10,000. The plates are tapped gently and to insure the coating solution covers the bottom of each well completely. The well are incubated at 4° C. overnight in a covered, humidified box.

The coating solution is discarded and 200 microliters PBS is added per well. The wells are then incubated at room temperature for 1 hr in a humidity box, then washed with 200 microliters of Wash Buffer (PBS, 0.5% TWEEN® and 0.02% sodium azide), and stored in a humidity box at 4° C. until use.

Antibody Coated Microtiter Plate

100 Microliters of prepared dilutions of anti-plaque antibody are applied to the surface of IMMULON® II microtiter plates (Dynatech). The coating solution concentrations are selected to be from 1–5 micrograms/well but can be varied up or down depending upon the selection of other reagents and immunoassay procedures to be followed. The plates are tapped gently and to insure the coating solution covers the bottom of each well completely. The wells are incubated at 4° C. overnight in a covered, humidified box.

The coating solution is discarded, and 200 microliters of 1% BSA in PBS is added per well. The wells are then incubated at rm temp for 1 hr in a humidity box, and the BSA solution is removed. The wells are the washed with 4 times with 200 microliters of Wash Buffer (PBS, 9.5% TWEEN®, and 0.02% sodium azide), and stored in a humidity box at 4° C. until use.

V. PROCEDURES FOR ANTIBODY LABELING

15H5 Antibodies and 17H3 Antibodies Peroxidase Conjugate

The following method is an one-step procedure for coupling peroxidase to a monoclonal antibody (e.g. the monoclonal antibody produced by hybridoma 15H5 or 17H3):

1. xmg purified 15H5 Ab or 17H3 Ab is dialyzed against 10 mM PBS pH 6.8 at 4° C. overnight.
2. 2xmg peroxidase enzyme is dissolved into the above Ab solution.
3. Add dropwise glutaraldehyde (1% solution) into above mixture. The ratio of glutaraldehyde solution to (antibody peroxidase mixture) is 1:20, then gently mix it on shaker at room temperature for two hours.
4. Dialyze conjugate against 10 mM PBS pH 7.2 (change buffer three times) at 4° C. overnight.
5. Conjugate is filtered by 0.2µ filter.

1-131 Labeled Antibody Agent

The antibody can be labeled with I-131 by the Pierce Iodobead method described by Rosebrough, S. (supra, p 575). 100 µl (microliters) of 0.2M PBS, pH 7.0, is added to 150 µg of antibody, followed by the addition is incubated for 10 min. The solution is removed with a pipette and reserved, and the beads are washed with 100 ul of 0.2M PBS, pH 7.0. The solution and wash buffer from the beads are combined. To separate the free iodine, the solution is washed exhaustively with a CENTRICON® C-30 filter. Approximately 60% of the original I-131 is bound to the antibody.

DTPA Labeled Antibody

DTPA is coupled to antibody by the method of Hnatowich, D. et al. [Journal of Immunolical Methods, 65:147 (1983)]. The bicyclic anhydride of DTPA is prepared as described by Hnatowich D. et al., [Int. J. Appl. Radiat. Isot. 33:327 (1982)] and is stored as the solid in a desiccator at R.T. A suspension of the anhydride in dry chloroform or ether (0.01 mg/ml) is prepared and an aliquot evaporated under nitrogen in a clean, dry teat tube. from 10–20 µl of the antibody solution in 0.05M bicarbonate buffer in saline, pH 7.0–7.5, is immediately added and the contents agitated for 30 to 60 sec. If the coupled antibody is to be purified before labeling, the preparation is diluted to about 0.2 ml with the above buffer and purified on a 5 cm gel filtration column (G-50; Roche Diagnostics, Nutley, N.J.) using saline eluant. The purification takes about 5 min and provides a product which is approximately 95% pure.

In-111 Labeled Antibody

Chelation grade I-111 (Medi Physics, Emeryville Calif.) in 0.5M acetate buffer, pH 6.0, is added to the DTPA-antibody conjugate solution described above, in stoichometric quantity. This yields the In-111 chelate-antibody conjugate. The product can be purified by conventional chromatography.

Fluorescein Antibody Agent

Antibody is dialyzed overnight against pH 9.5 carbonate/bicarbonate buffer solution. The concentration is determined (for example by otical density at 280nm. A solution of fluorescein isocyanate (1.0/mg/ml) in DMSO is prepared, and the desired volume (1–10% of total protein solution volume) is added to the antibody solution dropwise, with stirring. The reaction proceeds for two hours, shielded from light. The product is purified by gel filtration on SEPHADEX® G-25 gel in PBS containing 0.1% NaN3 to separate the unreacted or hydrolyzed fluorochrome. The absorbance of the conjugate is measured at 280 nm and at 495 nm to yield a solution of fluorescein labeled antibody.

Rhodamine Labeled Antibody

Antibody is dialyzed overnight against pH 9.5 carbonate/bicarbonate buffer solution as described in Example 7. A solution of rhodamine isocyanate (10.0 mg/ml) in DMSO is prepared, and the desired volume (1–10% of total protein solution volume) is added to the protein solution dropwise, with stirring. The reaction proceeds for two hours, shielded from light. The product is purified by gel filtration on SEPHADEX® G-25 gel in PBS containing 0.1% NaN3 to separate the unreacted or hydrolyzed fluorochrome. The absorbance of the conjugate is measured at 280 nm and 550 nm to yield rhodamine labeled antibody.

Coumarin Labeled Antibody

Antibody which binds specifically to atherosclerotic plaque (1 m mole) is dialyzed st 4° C. against a buffer solution of 0.01M PBS, pH 6.8 overnight. To this solution is added 50 nmole of 3-carboxy-7-hydroxycoumarin. The solution is added 50 mnole of 3-carboxy-7-hydroxycoumarin. The solution is cooled in an ice bath and added with 50 nmole of 1-ethyl-3-(3-dimethylaminopropyl) carbodiimide hydrochloride. After addition the mixture was stirred at 4° C. for one hour and chromatographed on a 2.5 c 50 cm column of SEPHAEX® G-50. The absorbance of the conjugate is monitored at 345 nm to yield a solution of coumarin labeled antibody.

Nile Blue A Labeled Antibody

Nile Blue A (350) mg) is diazotized according to the procedure described above. The solution containing the diazonium salt of Nile blue A is added dropwise to anti-plaque antibody (0.05 m mole) in on 0.1M PBS, pH 8.0. After addition the mixture is purified on a 2.5×50 cm SEPHADEX® column. The absorbance of the eluate is monitored at 628 nm to yield the Nile blue A labeled antibody.

Hematoporphyrin Conjugated

Antibody 1-Ethyl-3-(3-dimethylaminopropyl) carbodiimide (50 m mole) is added to a mixture of hematoporphyrin (50 m mole) and anti-plaque antibody (1 m mole) in 0.01M PBS, pH 6.8. After addition, the mixture is stirred at 4° C. for 2 hours. The mixture is then purified with a SEPHADEX G-50 column to yield the hematoporphyrin conjugated antibody.

Tetracycline Conjugated Antibody

The NHS ester of carboxymethyltetracycline is prepared as described above. To the anti-plaque antibody solution in 0.1M PBS, pH 8.0, is added portion wise the NHS ester of tetracycline. After addition, the mixture is allowed to sit at 4° C. for 2 hours. Purification of the mixture on a SEPHADEX® G-50 column yields the tetracycline conjugated antibody.

Enzyme Labeled Anti-Plaque Antibody

Anti-plaque antibody may be conjugated with alkaline phosphatase following the modified procedure of O'Sullivan, M. et al. [Analytical Biochem., 100:100 (1979)].

Horseradish peroxidase is conjugated to anti-plaque antibody in accordance withe procedure of Nygtren, H. et al. [Medical Biology, 57:187–191 (1979)] as follows: Horseradish peroxidase (HRP, Type II or TYPE VI, Sigma) is dissolved in 0.05M carbonate: bicarbonate buffer, pH 9.5, containing 0.25% glutaraldehyde (GA, Polaron). After 2 hr at room temperature, the excess GA is separated from the GA-HRP on a SEPHADEX® G-25 column (0.7 12 cm, Pharmacia) equilibrated with 0.15M NaCl. The GA-HRP complex is, in a second step, mixed with the antibody in 0.05M carbonate: bicarbonate buffer, pH 9.5, containing 0.15M NaCl, at different IgG:HRP ratios for 16–64 hr at 4° C. The reaction is stopped by the addition of lysine to a final concentration of 0.02M.

Trypsin-labeled Antibody m-Maleimidobenzoyl N-hydroxysuccinimide in dry dimethylformamide (100 μl, m mole/l) is added to the purified antiplaque antibody. The resulting mixture is stirred at room temperature for 30 min. The antibody solution is fractionated on a SEPHADEX® G-50 column with PBS as eluant. To the pooled antibody solution is added trypsin (13 mg) at room temperature. After addition, the mixture is stirred for another 2 hr. 2-Mercaptoethanol is a added to a final concentration of 2 mM/1, and the solution stirred for a further 30 min. The conjugate is dialyzed overnight against PBS (3×2 liters) to yield the trypsin-labeled antibody.

Papain Labeled Antibody

Equimolar amount of purified the anti-plaque antibody in papain are mixed in a solution of 0.1M sodium-potassium. To this solution is added 1 vol.% glutaraldehyde solution in phosphate buffer. After addition, the mixture is stirred at room temperature for 3 hours and finally dialyzed overnight against 0.1M. PBS, pH 8.0, at 4° C. The mixture is further purified on a SEPHADEX® G-50 column to yield the papain-labeled antibody.

Hyaluronidase Labeled Antibody

To a solution of hyaluronidase (5 mg) in 1.0 ml of 0.3M bicarbonate buffer, pH 8.0, is added phenyl isothicocyanate to protect the free amino groups on the hyaluronidase molecule. After addition, the solution is stirred gently at room temperature for 1 hour. A solution of sodium periodate (0.06M in distilled water) is added and the mixture stirred gently for 30 minutes. One ml of 0.16M of ethylene glycol in distilled water is added, and the solution stirred for another 1 hour at room temperature. After dialyzing against 0.01M of sodium carbonate buffer, pH 9.5, at 4° C. (3×1 liter), the mixture is mixed with purified anti-plaque antibody. The reaction mixture is stirred for 2–3 1 hours and treated with 5 mg of sodium borohydride. The mixture is allowed to stand at 4° C. overnight. Following dialysis against PBS buffer, the dialyaia against PBS buffer, the mixture is chromatographically purified with a 1.5×85 cm (BN) SEPHADEX® G-100 column to yield the hyaluronidase antibody.

Kallikrein Labeled Antibody

Equimolar amount of purified anti-(normal vascular epithelium) antibody and urinary kallikrein are mixed in 0.1M sodium-potassium phosphate buffer, pH 6.8. The antibody and kallikrein are coupled following the procedure of Example 12. The final reaction mixture is purified with a 2.5×50 cm SEPHADEX® G-200 column to yield kallikrein conjugated anti-(normal vascular epithelium) antibody.

Collagenase Labeled Antibody

Collagenase I (65 lysines) collagenase II (50 lysines) is dissolved in 0.05M phosphate buffer, pH 8.0. To this solution is added m-maleimidobenzoly N-hydroxysuccinimide in anhydrous dimethylformamide (100 ul, 8 m mole/liter). After addition, the mixture is stirred for 30 minutes. The enzyme solution is first fractionated SEPHADEX® G-50 column with PBS as eluant and teated with purified anti-plaque antibody. The mixture is stirred for 2 hours at room temperature and added with 2-mercaptoethanol to a final concentration of 2 m mole/l. The mixture is stirred for a further 30 minutes and chromatographically purified on a SEPHADEX® G-50 column to yield collagenase conjugated anti-plaque antigen antibody.

Beta-1 Anticollagenase Labeled Antibody $Beta_1$ anti-collagenase and anti-(normal vascular epithelium) antibody are coupled with glutaraldehyde by the procedure described hereinabove. The final reaction mixture is purified with a 2.5×50 cm SEPHADEX® G-200 column to yield the $beta_1$ anticollagenase labeled anti-(normal vascular epithelium) antibody.

VI. PROCEDURES FOR IMAGING ATHEROSCLEROTIC PLAQUE

DPTA coupling of Z2D3

1. Preparation of mixed Anhydride of DTPA [Krejcarek and Tucker, BBRC, 77:581 (1977)]
   a) 100 mg of triethylammonium-DTPA+2 ml acetonitrile
   b) Cool to 4° C.
   c) Add isobutylchloroformate
   d) Mixed anhydride of DTPA formed at 4° C.
2) Modification of Z2D3
   a) 1.69 Z2D3 in 0.45 ml 0.1M $NaHCO_3$ ($2\times10^{-9}$ moles)
   b) Add 15 μl of carboxycarbonic anhydride of DTPA ($2\times10^{-7}$ moles
   c) React at RT for 1 hr.
   d) Dialyze in 6 L 0.15M NaCl at 4° C., overnight 3) In-111 labeling of DTPA-Z2D3
  a) 0.25 mg DTPA-Z2D3 in 151 μl and 1 mCi $^{111}$In-Cl$_3$ in equi-volume of 1M citrate pH 5.5
  b) Incubate 30 min at RT
  c) Separate free from antibody bound $^{111}$In by sephadex G-25 column chromatography. The $^{111}$In-DTPA-Z2D3 was eluted with 0.15M NaCl. The activity in the void volume was pooled and used for in vivo studies.

4) In Vivo Studies

Rabbits with approximately 6 week old denuded descending aortic endothelium were injected with 0.5–1.0 mCi $^{111}$In-DTPA-Z2D3 intravenously via ear vein administration.

The rabbits were anesthetized with Ketamine and Rompum, and imaged with a gamma camera (Ohio Nuclear, Sigma 410 or 100) equipped with a medium energy collimator. Anterior images were obtained soon after IV administration and at 24 H. The animals were then infused intravenously with 5 ml of 5% Evans Blue, followed by euthanization with IV pentobarbitol.

The descending aorta segment from the thorax region was used as normal control relative to the de-endothelialized abdominal segment of descending aorta. The aortic segments were cleaned of blood and dissected enfaced.

These segments were weighed and then counted in a gamma counter. The segments were then used to obtained macro-autoradiographs. The segments were laid enfaced on mammography film and allowed to develop for 1 to 2 weeks. Subsequently the films were developed and color photographs of the segments made for comparison to the autoradiographs.

Localization of Experimental Atherosclerotic Lesions with a Monoclonal Antibody

Monoclonal antibody Z2D3-5C5 F(ab')$_2$ fragments specific for an atheroma connective tissue antigen were used for non-invasive imaging of atheromatous lesions in an experimental rabbit model produced by balloon catheter de-endothelialization of the descending aorta followed by a high cholesterol and fat diet. Seven weeks later, 3 animals were injected intravenously with In-111 Z2D3. I-125 Z2D3 and I-125 nonspecific monoclonal F(ab')$_2$ were also injected in each one of these animals. Images were recorded at 15 min, 24 H, and 48 H. The normal (N) and lesioned (L) segments were weighed, counted by gamma scintigraphy and expressed as mean percent injected dose per gram. Lesions could be visualized in 1 rabbit with In-111 Z2D3 and in another with I-125 Z2D3. Macroautoradiography of the exvivo aorta demonstrates that the uptake of Z2D3 was superior to that of nonspecific antibody. The In-111 Z2D3 uptake was 0.035±0.0001 in L as compared to 0.0008±0.0003 in N. The I-125 Z2D3 uptake was 0.026 and 0.005 and the I-125 nonspecific F(ab')$_2$ uptake was 0.008 and 0.003, respectively. This study indicates the potential feasibility of non-invasive visualization of atheromatous lesions of aorta with monoclonal antibodies.

VII. PROCEDURES FOR HISTOLOGY

Histological Counter-Staining With Hemotaxylin Lerner-1

Reagents and Supplies
Absolute ethanol (Gold Shield Chemical-Proof 200).
Hematoxylin Lerner-1 (SP #S7737-1 or equivalent). Xylene (SP #8668-4, Mallinckrodt or equivalent). COVERBOND® Mounting Media (SP #M763904 or equivalent).
Deionized water.
Coplin jars (SP #S7655-1 or equivalent).
Staining dishes (SP #S7675-1 or equivalent).
Coverslip (SP #M6020 or equivalent).
Staining Procedure

| Reagent | Procedure |
| --- | --- |
| 1. Hematoxylin Lerner-1 | 2 dips (8 counts each) |
| 2. D.I. water (3 times) | 1 dip each |
| 3. 70% ethanol | 15 dips |
| 4. 95% ethanol | 15 dips |
| 5. Absolute ethanol (2 times) | 20 dips each |
| 6. Xylene (2 times) | 1 minute each |
| 7. Place 3 drops of Coverbond mounting media on coverslip. | |

Histological Staining with VECTOR® (Avidin-Biotin Complex)

Reagent and Supplies
Reagent and Supplies
Unfixed frozen tissue section (5–6 μm thick) preferably freshly cut and stored overnight at −80° C.
Bovine Serum Albumin BSA (Sigma #A-7030).
Normal Horse Serum (Vector—Peroxidase Mouse IgG PK 4002).
Primary antibody.
Biotinylated horse antimouse IgG (Vector—Peroxidase Mouse IgG PK 4002).
Hydrogen peroxide 30% (Sigma #H-1009 or equivalent).
Methyl alcohol absolute low acetone (Mallinckrodt #3016-4 or equivalent).
3,3'-Diaminobenzidine—DAB (Sigma #D-9015).
TRIZMA® base (Sigma #T-1503 or equivalent).
Sodium chloride (Mallinckrodt #7581 or equivalent).
1N HCl (Prepared from Ricca Chemical Company #3740 or equivalent).
Sodium phosphate, dibasic anhydrous (Mallinckrodt #7917 or equivalent).
Potassium phosphate, monobasic, anhydrous (Mallinckrodt #7100 or equivalent).
Equipment
Lab-line orbit shaker
Fume hood
Covered, dark humidified container
Reagent Preparation
Phosphate-buffered saline (PBS) pH 7.2, 1 liter
Sodium chloride NaCl 7.2 g
Sodium phosphate Na$_2$HPO$_4$ 1.48 g dibasic, anhydrous
Potassium phosphate KH$_2$PO$_4$ 0.43 g monobasic, anhydrous
D.I. water 0.5 to 1000 ml.
PBS+0.1% BSA, pH 7.2, 1 liter
BSA 1 g
PBS, pH 7.2, dissolve in 1000 ml.
Make fresh every time
Tris-HCl/saline buffer (0.05M Tris-HCl+0.15M NaCl), pH 7.6
  0.5 Tris HCl pH 7.6 (stock solution) Trizima base.
  D.I. water, dissolve in HCl; adjust to pH 7.6
  D.I. water 0.5 to 1000 ml.
  0.9% NaCl (normal saline).
  NaCl.
  D.I. water, dissolve in 1000 ml.
Tris HCl/saline buffer (working solution). Mix 1 part of 4.3.1 with nine parts 4.3.2
Prepare fresh every time.
3,3'-Diaminobenzidine tetrahydrochloride (DAB).

0.5% DAB (stock solution).
(1 vial contains 0.1 g lyophilized DAB).
Tris/saline buffer, pH 7.6. Dissolve and aliquot 1 ml into vials and store at −20° C.
0.05% DAB and 0.01% $H_2O_2$ working solution.
Stock DAB 1 ml
Tris/HCl saline buffer 9 ml
30% $H_2O_2$ 4 μl
VECTASTAIN® ABC Reagent (1 drop=50 μl
Reagent A 2 drops
Reagent B 2 drops
QS with PBS/BSA to 10 ml
Mix immediately and allow to stand for 30 minutes before use.

Procedure

Immunoperoxidase staining

1. Remove slides from freezer and dry for 10 minutes.
2. Wash in PBS/BSA on shaker (very gently) for 20minutes.
   Note: After this step, sections should not be allowed to dry out during any of the remaining procedures. Drying out can lead to misleading results.
3. Incubate with 3% normal horse serum for 20 minutes.
4. Blot excess serum from section.
5. Incubate section with appropriate dilution of primary antibody for 30 minutes, or longer if required, in humidified container.
6. Wash slides for 10 minutes in PBS/BSA on shaker.
7. Incubate section with antimouse IgG biotinylated antibody (1:50 dilution in PBS/BSA) for 30 minutes.
8. Wash slides for 10 minutes in PBS/BSA on shaker.
9. Block endogenous peroxidases with 0.3% $H_2O_2$ in methanol for 10 minutes on shaker.
10. Wash slides for 10 minutes in PBS/BSA on shaker.
11. Incubate with VECTASTAIN® ABC for 20 minutes.
12. Wash slides for 10 minutes in PBS/BSA on shaker.
13. Incubate with DAB for 7 minutes.
14. Wash section for 5 minutes in D.I. water.
15. Perform counter staining with hematoxylin.

VIII. METHODS OP TREATING ATHEROSCLEROTIC PLAQUE

Figure 30A:
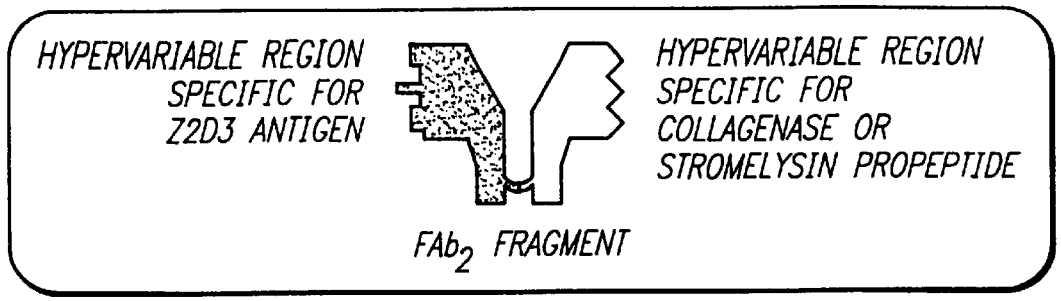
FIG. 30—Schematic of enzymatic reduction of atherosclerotic plaque by proenzyme targeting with plaque specific antibody fragments.
Figure 30B:
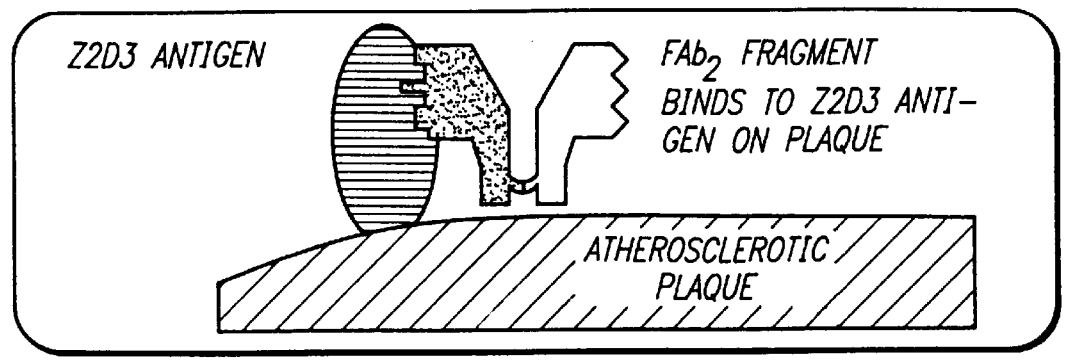
Figure 30C:
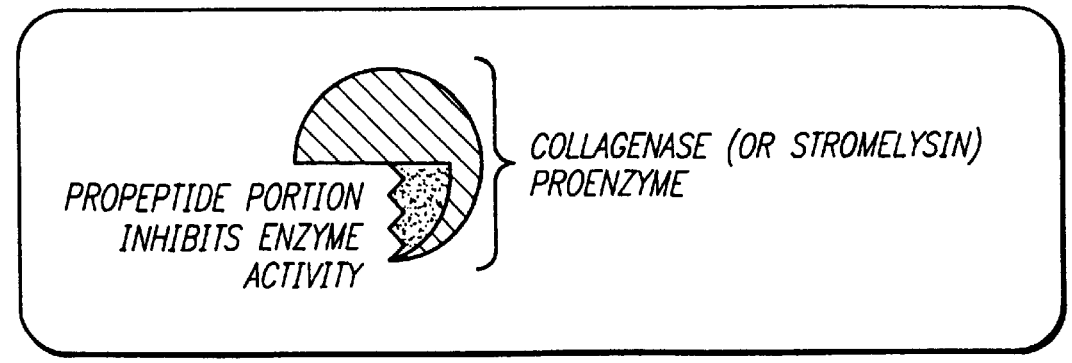
Figure 30D:
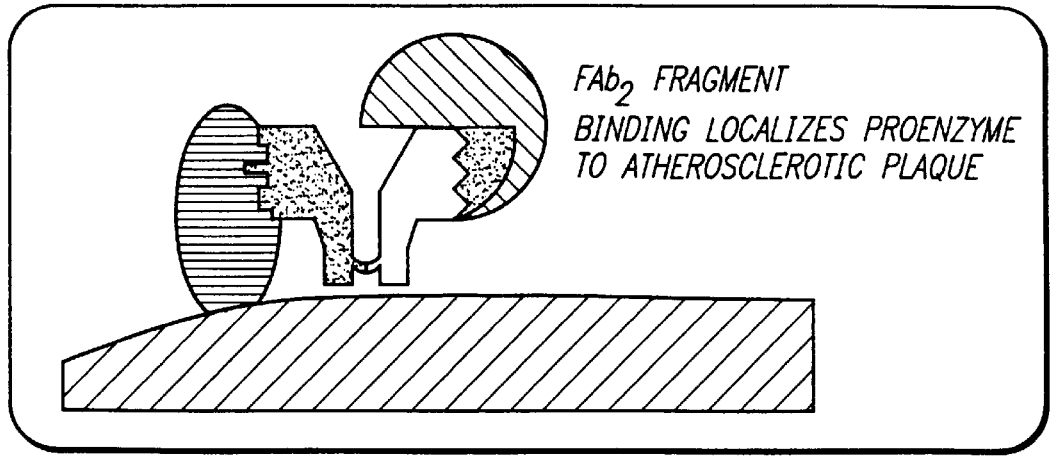
Figure 30E:
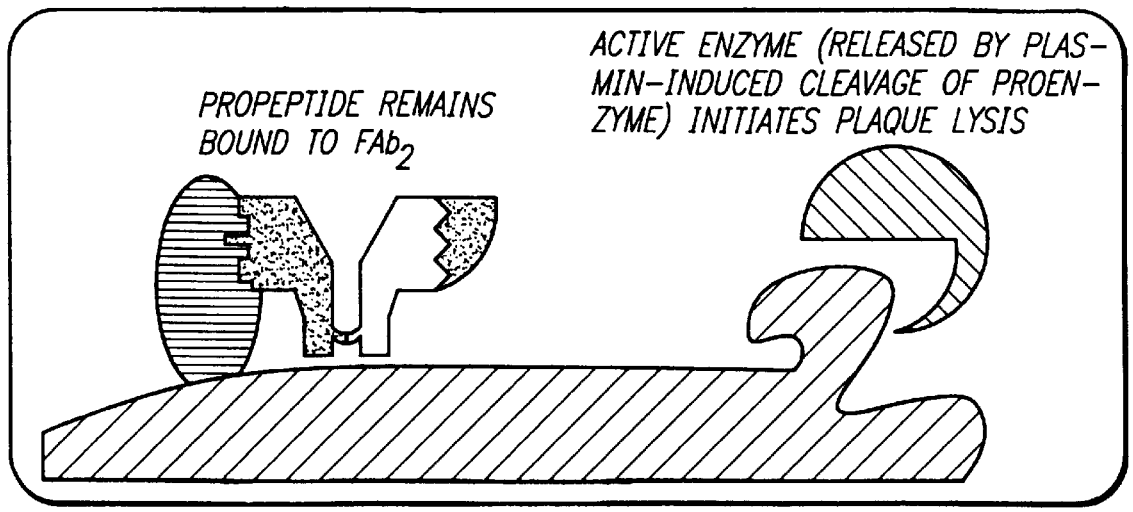

Enzymatic Reduction of Atherosclerotic Plaque by Proenzyme Targeting with Plaque-specific Antibody Fragments 1. $FAB_2$ fragments having the following properties are intravenously administered (see FIG. 30A):
   a. Bifunctional antibody with one hypervariable region binding Z2D3 antigen, and the other binding the propeptide of the fibroblast collagenase proenzyme.
   b. Bifunctional antibody with one hypervariable region binding Z2D3 antigen, and the other binding the propeptide of the neutrophil collagenase proenzyme.
   c. Bifunctional antibody with one hypervariable region binding Z2D3 antigen, and the other binding the propeptide of the type IV/V collagenase proenzyme.
   d. Bifunctional antibody with one hypervariable region binding Z2D3 antigen, and the other binding the propeptide of the stromelysin proenzyme.
   e. A mixture of the four $FAB_2$ fragments above (a–d) labelled with radionuclide x, and representing a minor component of the overall pool of $FAB_2$ fragments.
2. The patient is scanned with a gamma camera, attuned to radionuclide x, 24 to 48 hours after administration of the $FAb_2$ fragments, and an estimate is made of the quantity of $FAb_2$ fragments localized in the target lesions, based on the amount of radiolabelled $FAb_2$ fragments detected. (see FIG. 30B)
3. An appropriate mixture of fibroblast collagenase, neutrophil collagenase, type IV/V collagenase, and stromelysin proenzymes is intravenously administered, in proportion to the number of receptive $FAb_2$ fragments calculated to be localized in the target lesions. A small portion of each proenzyme is labelled with radionuclide. (see FIG. 30C)
4. Using a gamma camera attuned to radionuclide y, the proenzyme mixture is administered in incremental doses, until the desired amount is localized in the lesions. The desired amount is that which will dissolve enough plaque to relieve the arterial obstruction, without causing aneurysm formation or perforation in severely diseased vessels. (see FIG. 30D)
5. Tissue plasminogen activator (TPA) in intravenously administered in an amount sufficient to generate enough circulating plamsin to cleave the functional enzymes from their bound propeptides, yet insufficient to create a hemorrhagic diathesis. (see FIG. 30E)
6. Once released from the $FAb_2$ fragments localized in the plaque, the collagenase and stromelysin enzymes immediately bind and begin degrading their adjacent substrates:
   a. collagen type I (neutrophil collagenase)
   b. collagen type III (fibroblast collagenase)
   c. collagen type IV/V (type IV/V collagenase)
   d. proteoglycans/fibronectin (stromelysin).

This invention is further illustrated by the following specific, but non-limiting examples. Temperatures are given in degrees Centigrade and percents as weight percents unless otherwise specified. Examples which are constructively reduced to practice herein are presented in the present tense, and examples representing laboratory experiments previously reduced to practice are presented in the past tense.

Plaque Treatment

A representative treatment protocol can be as follows:

1. Catheterized artery (coronary ostia, carotid, aorta or peripheral vessels).
2. Visually examine vessel lumen with contrast agent.
3. Inject antibody-enzyme inhibitor conjugate in a physiologically acceptable solution.
4. Allow excess clearance time.
5. Inject a plaque antibody-enzyme conjugate in a physiologically acceptable solution in which the enzyme remains active.
6. Let circulate for sufficient time to permit perfusion (e.g. 60 min.)
7. Visually examine vessel intima and/or media with contrast agent under fluoroscopy.
8. Repeat Steps 5–7 until lumen restoration is satisfactory.
9. Inject enzyme inhibitor in physiologically acceptable solution to stop all enzyme reaction of any given therapeutic episode.
10. Repeat Step 7 after a few minutes or after clearance of reagents. If no further enzymatic reduction of vessel is seen, terminate procedure. Otherwise repeat Step 9 and 10, or introduce inhibitor by IV.

Discussion

Figure 5A:
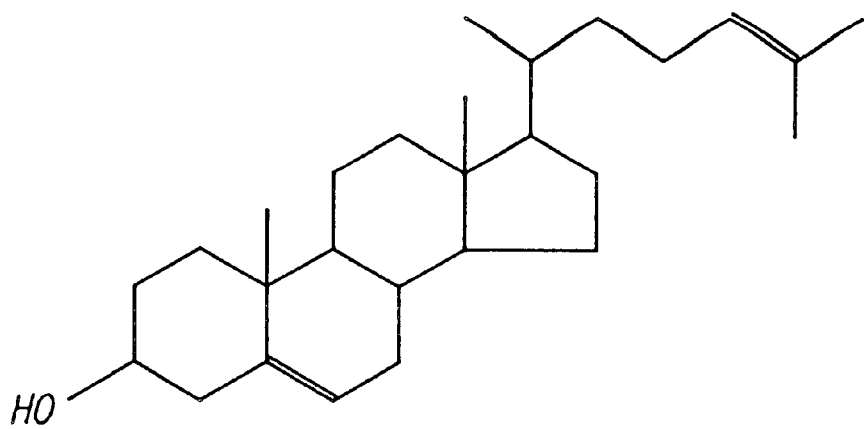
FIG. 5—Level of IgA which specifically binds to atherosclerotic plaque antigen for persons with CAD, normal persons less than 35 years of age, and normal persons greater than 35 years of age.
Figure 5B:
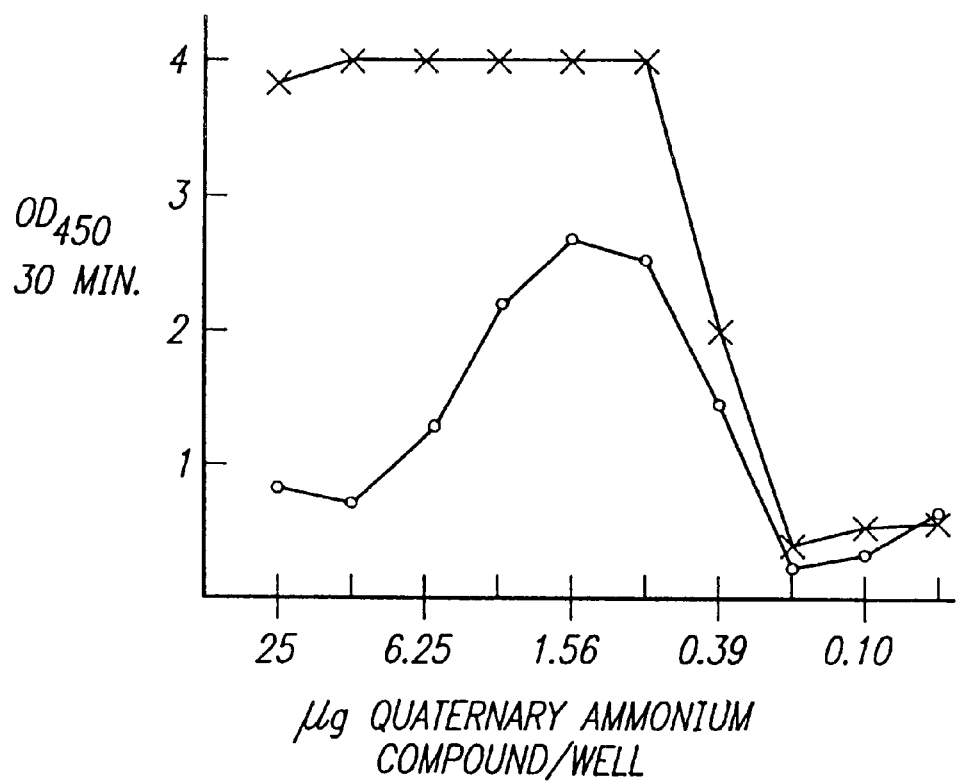
Figure 6A:
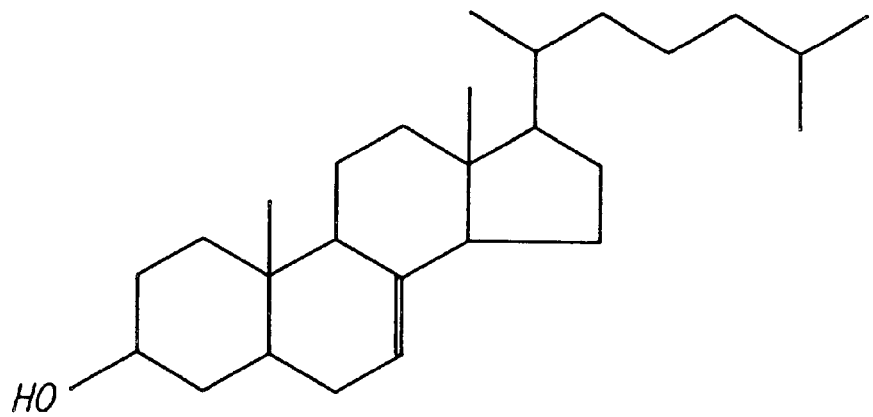
FIG. 6—Levels of atherosclerotic plaque antigen as determined by radioimmunoassay for persons with CAD, normal persons less than 35 years of age, and normal persons greater than 35 years of age.
Figure 6B:
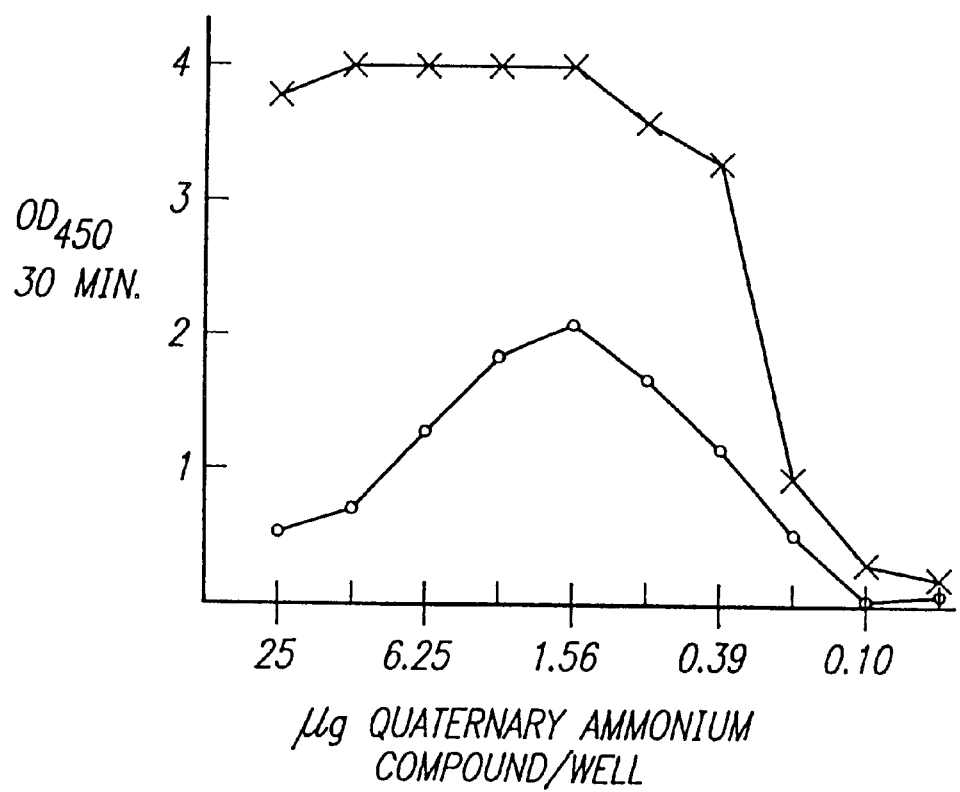

Atherosclerosis is characterized by the presence of one or more of the atherosclerotic plaque specific antigens disclosed in the subject invention. Because of the cyclical nature of the immune response, either the plaque antigen or antibody which specifically binds to the antigen may be detected at any one point in time. Accordingly, the presence of either the antigen or antibody thereto is indicative of atherosclerotic plaque. FIG. 5 shows a comparison of levels of IgA specific to atherosclerotic plaque antigen present in the sera of normal persons less than 35 years of age, and persons diagnosed as having coronary artery disease (CAD). As indicated in the figure, 70 of 207 persons under 35 years of age, and 21 of 121 normal persons over 35 years of age, had elevated levels of IgA in their serum. Normal persons are defined as apparently healthy individuals not known to have CAD. FIG. 6 shows a comparison of levels of atherosclerotic plaque specific antigen present in the sera of normal persons greater than 35 years of age, and persons diagnosed as having CAD. As with levels of IgA, levels of IgG which specifically binds to the atherosclerotic plaque specific antigen are higher in persons with CAD. Of the persons afflicted with CAD, 45 of 125 tested showed elevated levels of antigen, whereas only 4 of 25 normal persons under 35 years of age, and 8 of 49 normal persons over 35 years of age showed elevated levels of antigen.

Figure 7A:
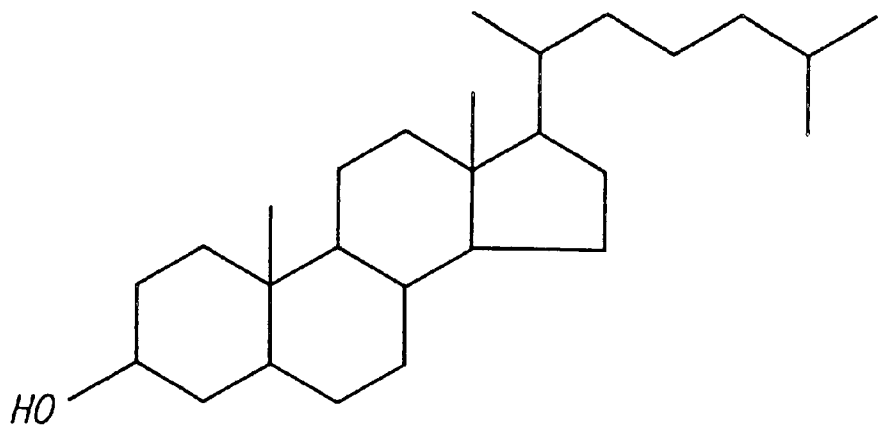
FIG. 7—Atherosclerotic plaque antigen level for normal persons vs. age.
Figure 7B:
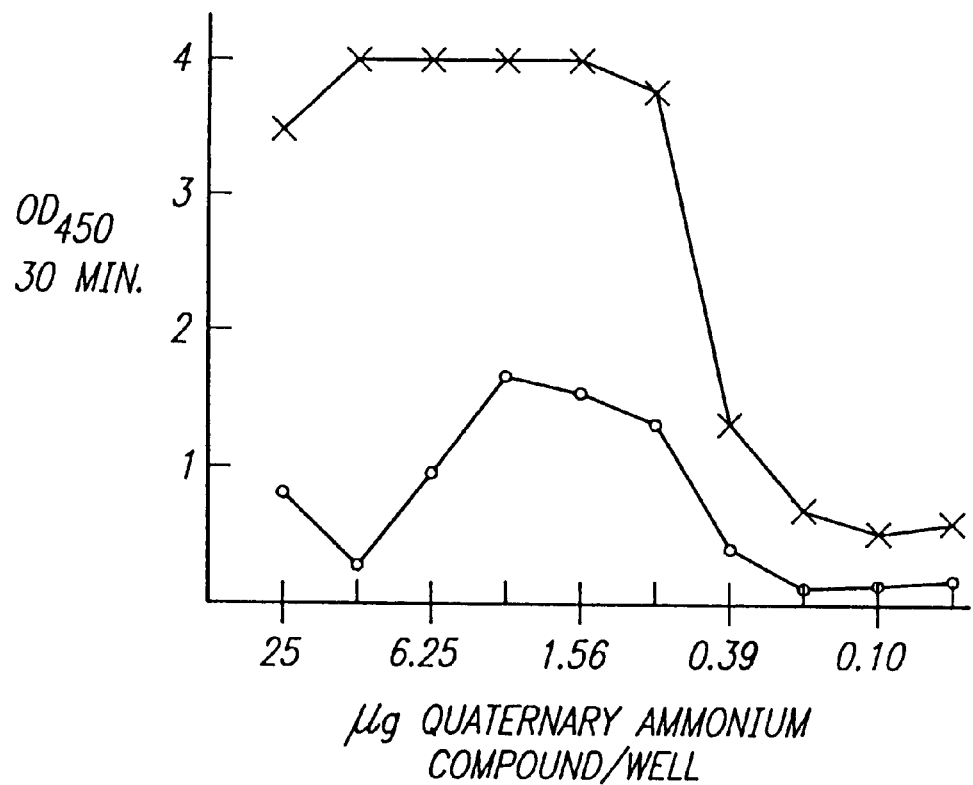
Figure 8A:
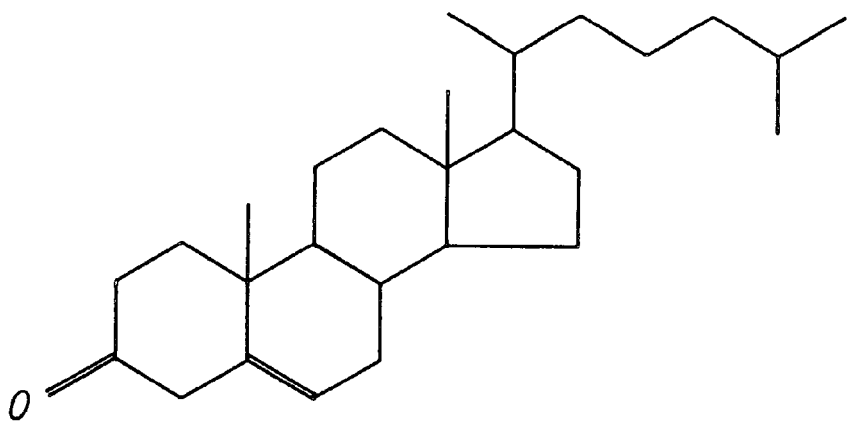
FIG. 8—Atherosclerotic plaque antigen level for persons with severe CAD, i.e. greater than 50% occlusion, vs. age.
Figure 8B:
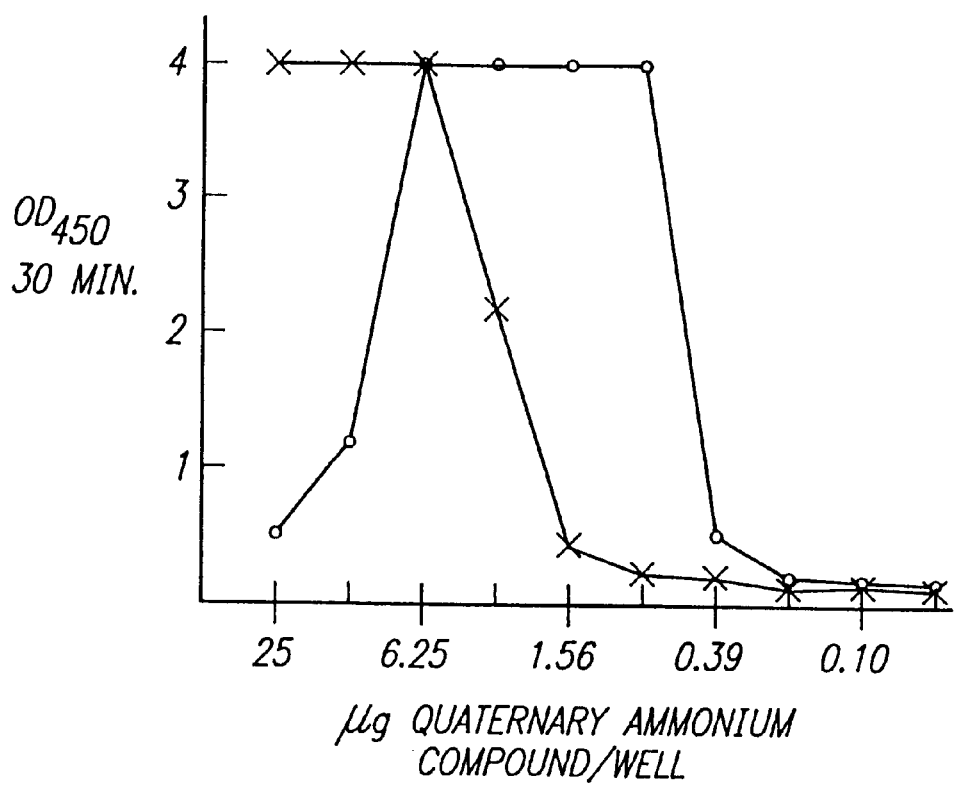
Figure 9A:
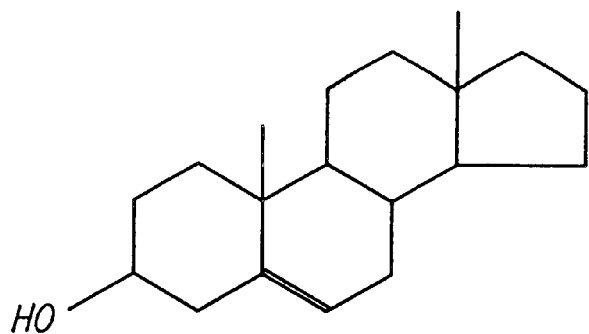
FIG. 9—Atherosclerotic plaque antigen levels for persons with mild CAD vs. age.
Figure 9B:
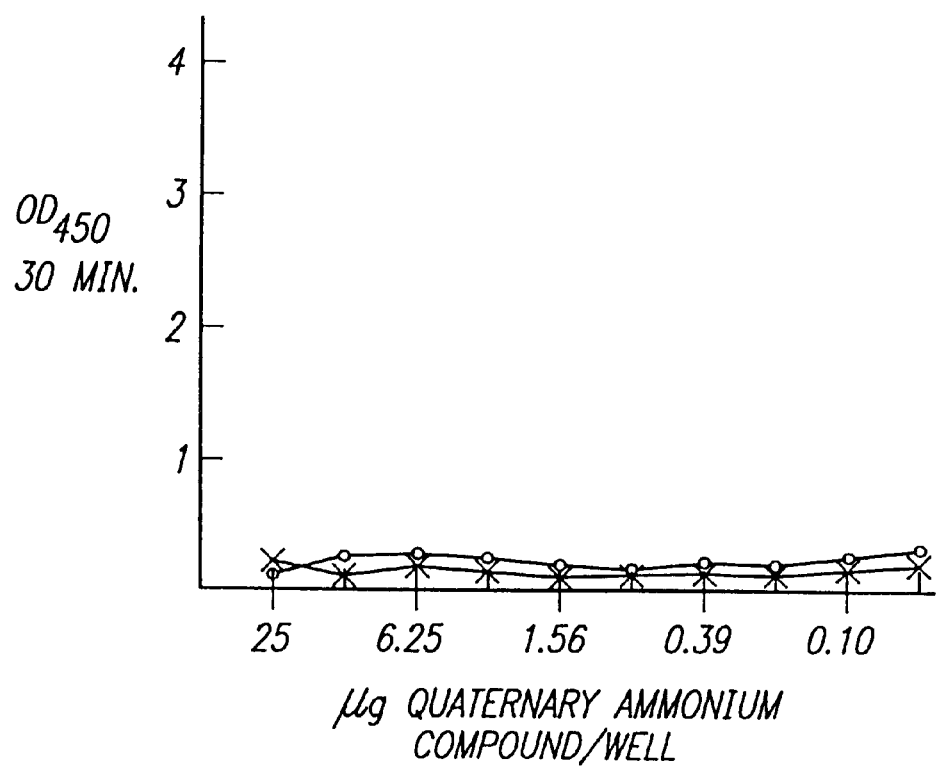
Figure 10A:
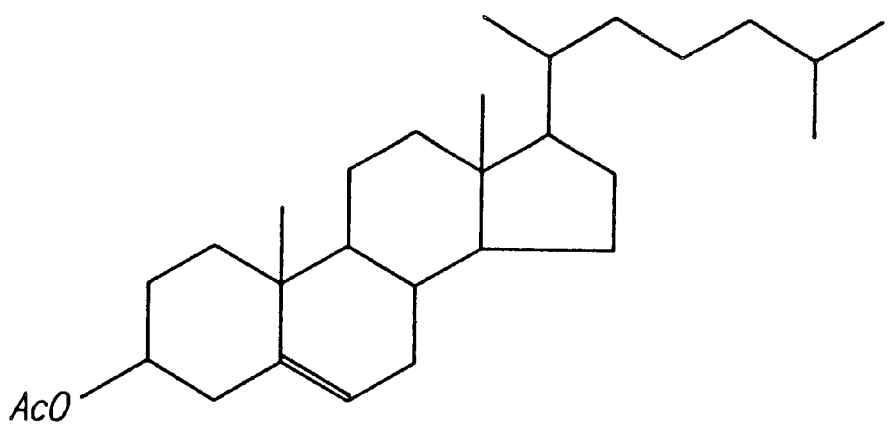
FIG. 10—Level of IgG which specifically binds to atherosclerotic plaque antigen for normal persons vs. age.
Figure 10B:
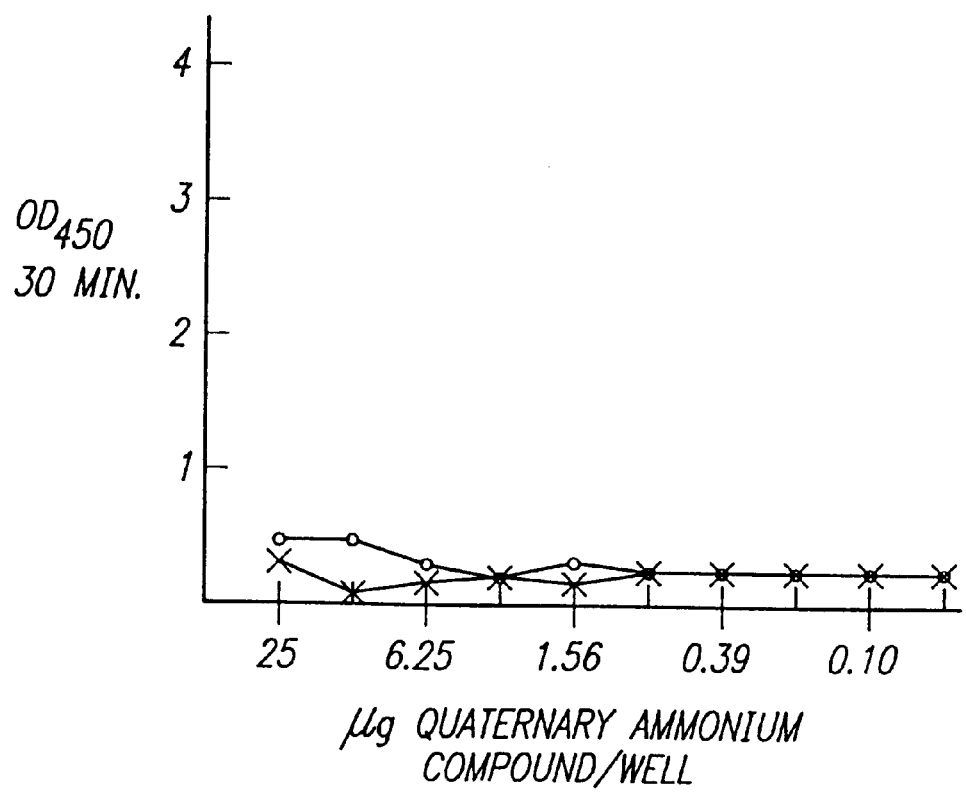
Figure 11A:
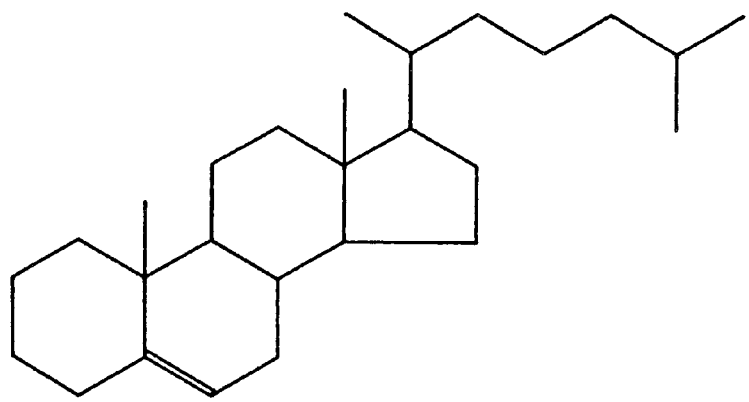
FIG. 11—Level of IgG which specifically binds to atherosclerotic plaque antigen for persons with severe CAD, i.e. greater than 50% occlusion, vs. age.
Figure 11B:
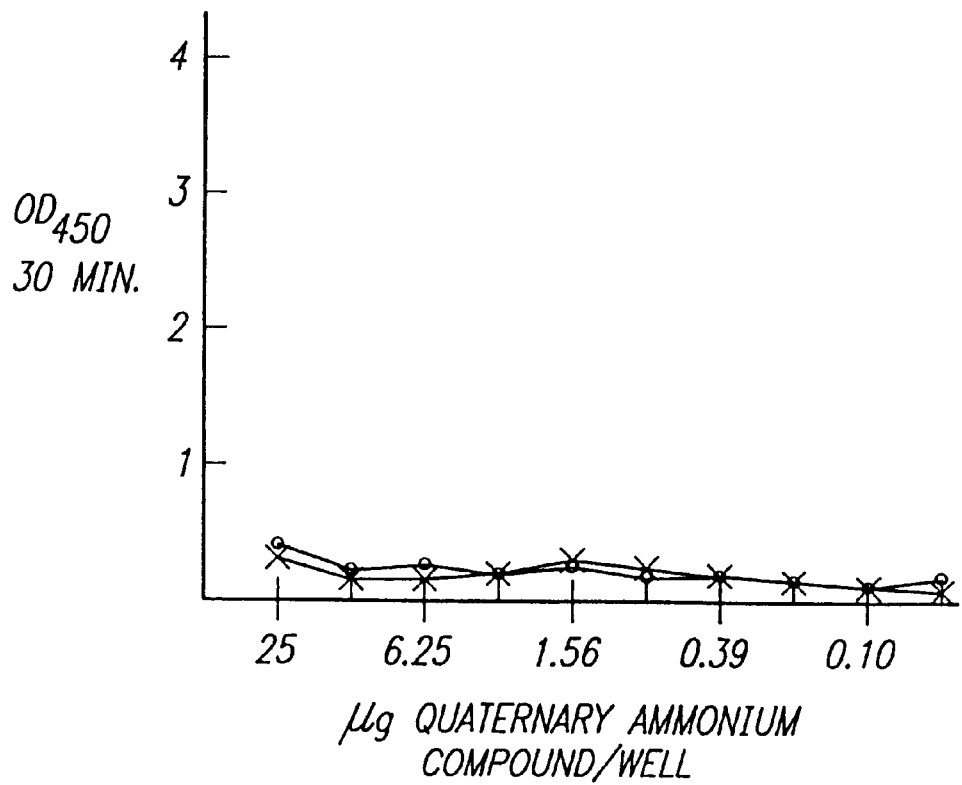
Figure 12A:
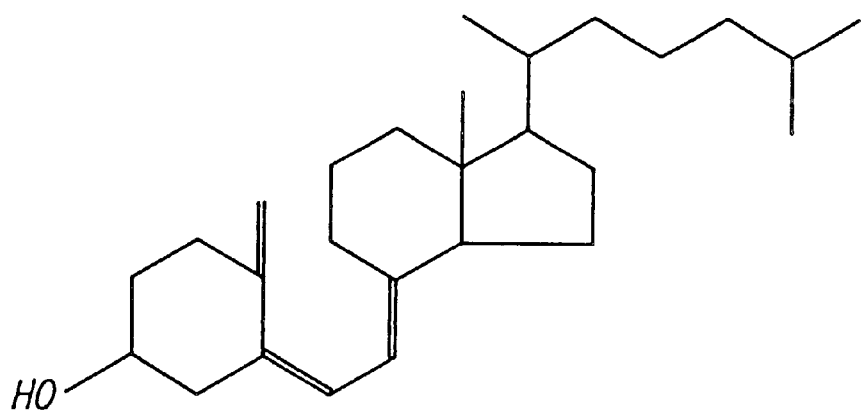
FIG. 12—Level of IgG which specifically binds to atherosclerotic plaque antigen for persons with mild CAD vs. age.
Figure 12B:
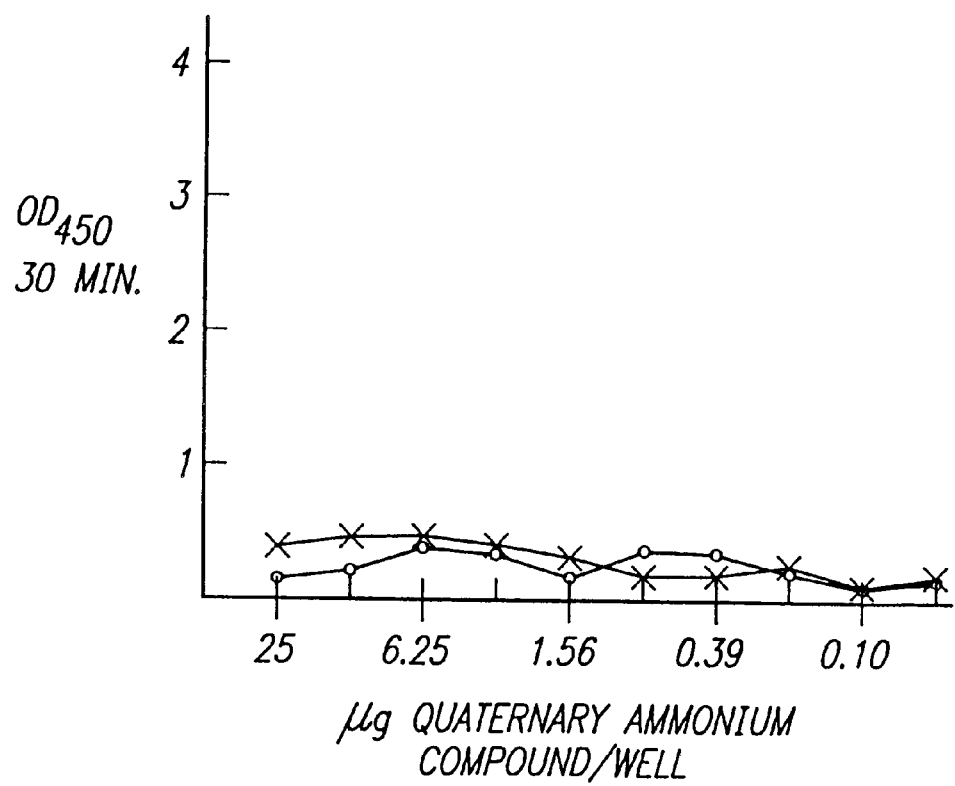
Figure 13:
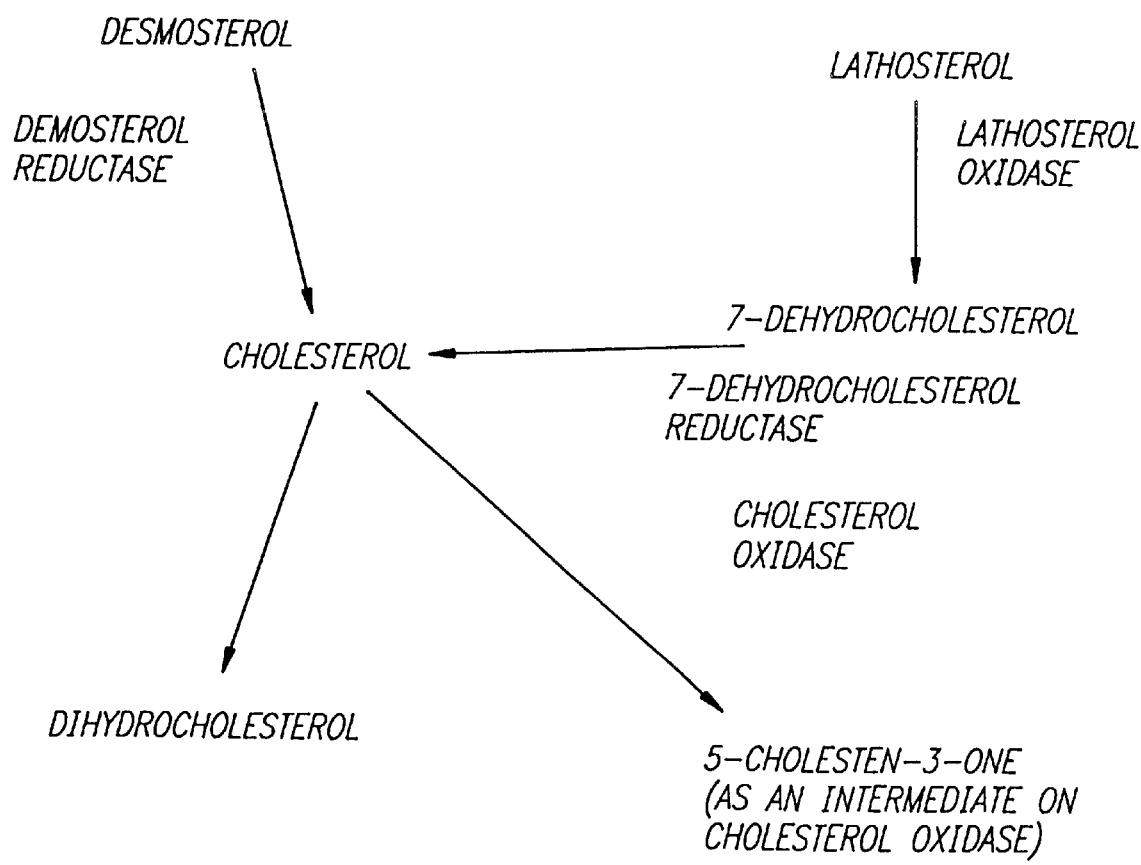
FIG. 13—Level of IgA which specifically binds to atherosclerotic plaque antigen for normal persons vs. age.
Figure 14:
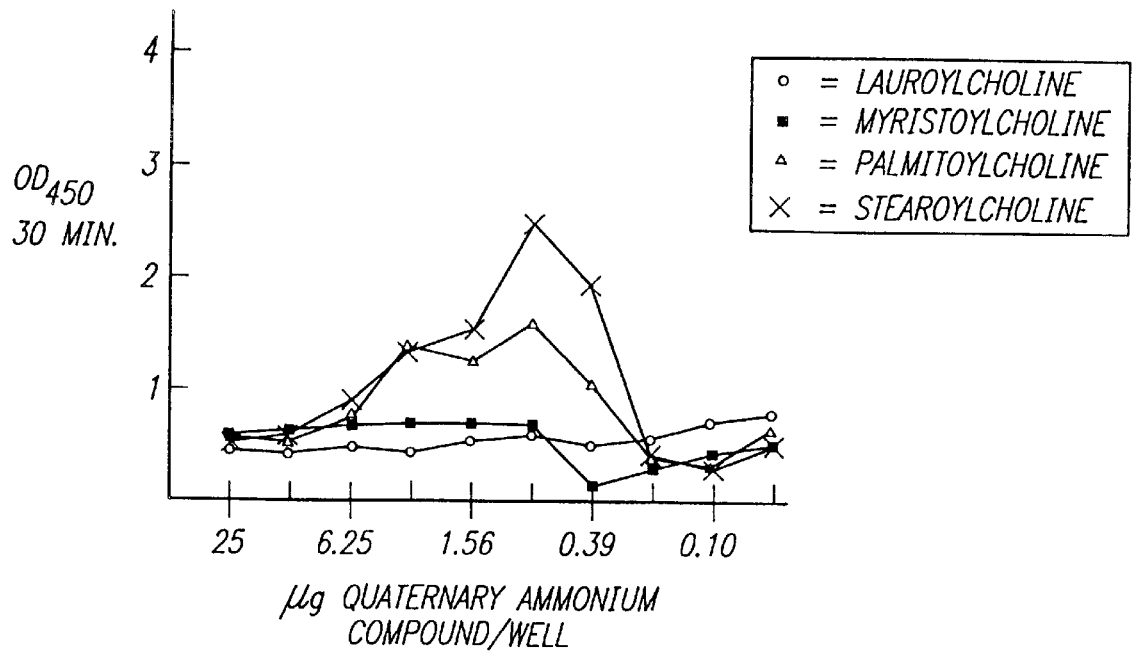
FIG. 14—Level of IgA which specifically binds to atherosclerotic plaque antigen for persons with severe CAD, i.e. greater than 50% occlusion, vs. age.

The amount of antigen expressed was studied as a function of age and severity of disease. FIG. 7 shows a plot of antigen level vs. patient age for apparently healthy individuals. In contrast, FIG. 8 shows the same plot for individuals having 50% or greater occlusion of their coronary artery, and FIG. 9 shows the same plot for individuals having mild CAD. As is graphically illustrated, the amount of antigen present in sera is less dependent upon age than upon severity of CAD. Atherosclerosis is therefore indicated by the presence of the atherosclerotic plaque specific antigen.

The prevalence of antibodies which bind specifically to the atherosclerotic plaque antigen appear to increase with age in normal persons. However, this increase is small relative to the levels of antibodies detected in patients with CAD. (FIGS. 10–14 ).

Figure 15:
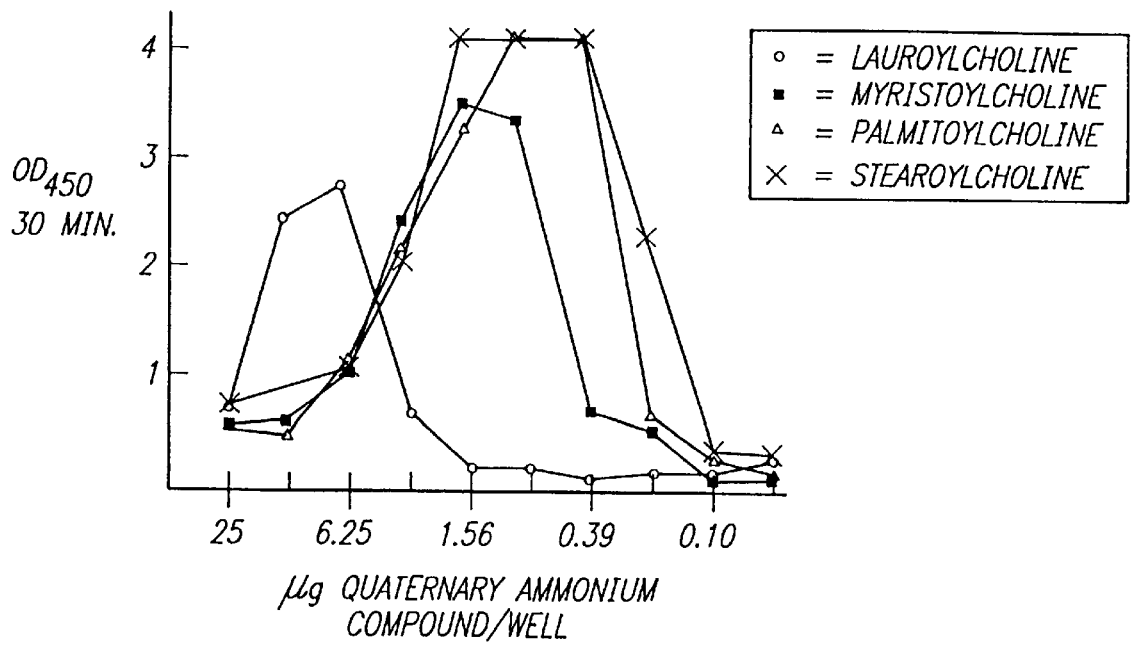
FIG. 15—Level of IgA which specifically binds to atherosclerotic plaque antigen for persons with mild CAD vs. age.
Figure 16:
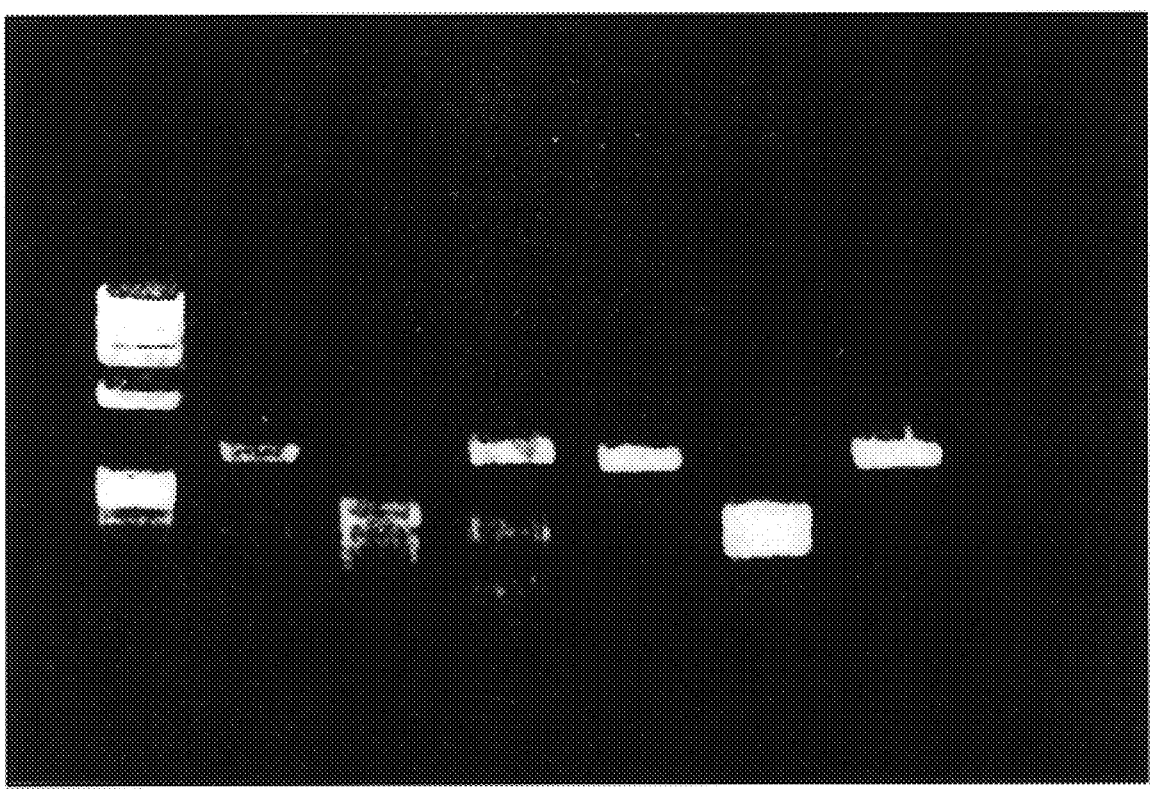
FIG. 16—Positive prevalence of atherosclerotic antigen, i.e. percent of persons above normal, vs. age group.

FIG. 15 depicts positive prevalence for the antigen in a population based on age. The persons tested were from 31 to 75 years of age.

Figure 2A:
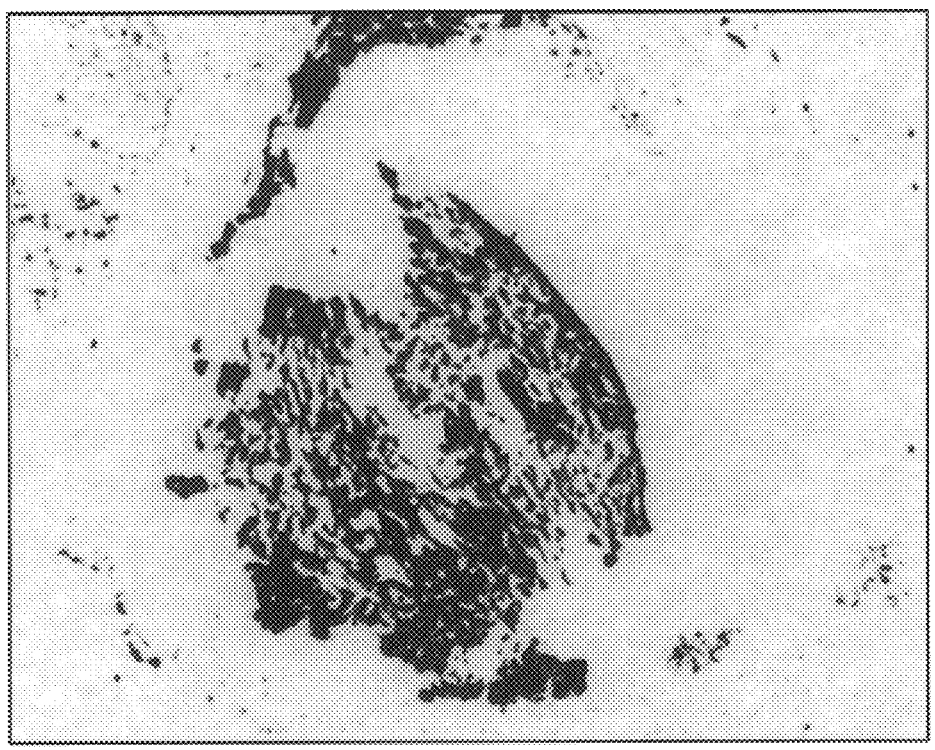
FIG. 2—DEAE Fractionation (Preparative)—Auto-Antibody Assay. The dotted line represents the amount of binding of CAD serum compared to normal serum in each fraction. The solid line represents the amount of protein in each fraction as detected by absorbance at $OD_{280}$. The dashed line represents a NaCl gradient from 0 to 1.0M NaCl.
Figure 2B:
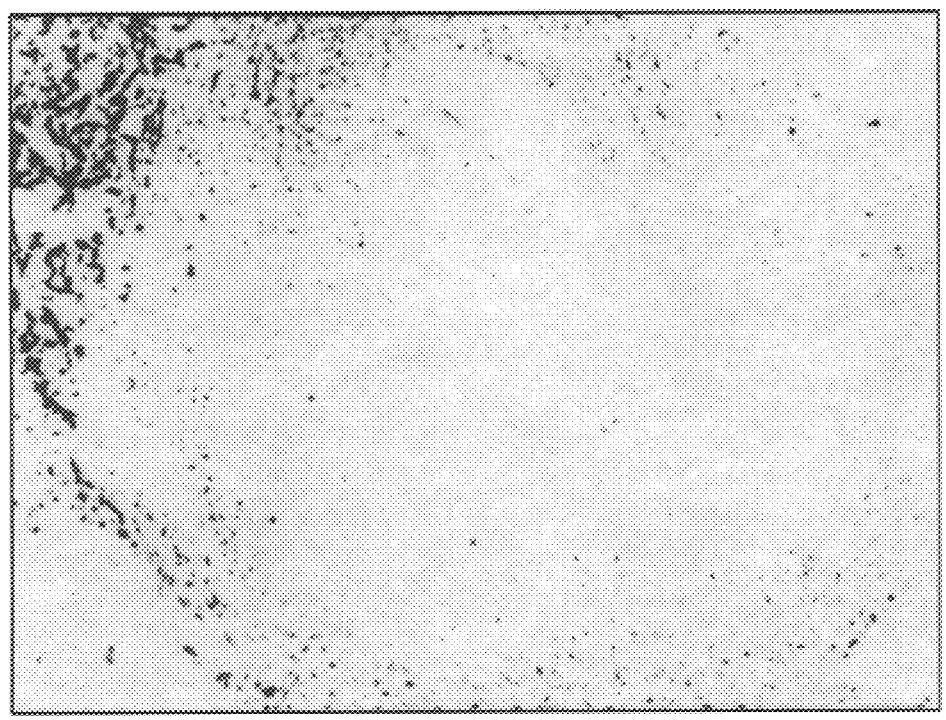
Figure 3A:
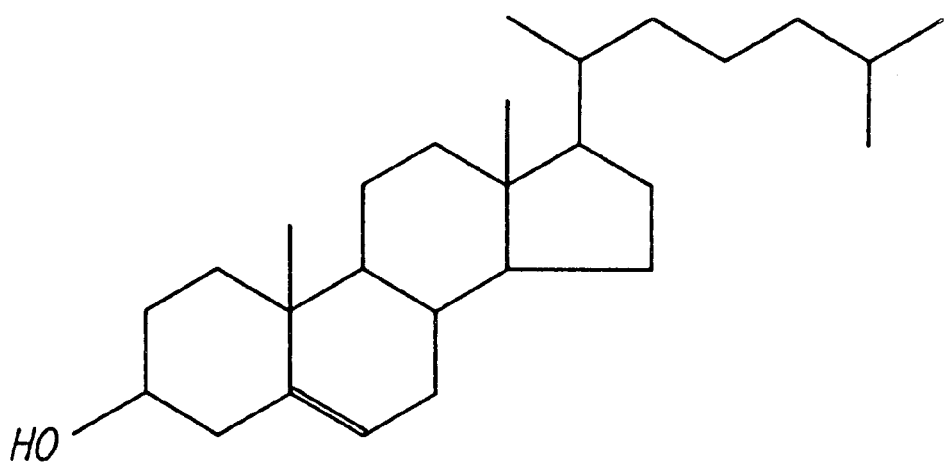
FIG. 3—DEAE fractionation (Analytical)—Antigen capture assay. The dotted line represents the amount of auto-antigen in each fraction as detected by binding to the monoclonal antibody produced by hybridoma 15H5. The results shown are for peroxidase conjugated antibody to the antigen and the plates are read at $OD_{450}$. The solid line represents the amount of protein in each fraction as detected by absorbance at $OD_{280}$. The dashed line represents a NaCl gradient from 0 to 1.0M NaCl.
Figure 3B:
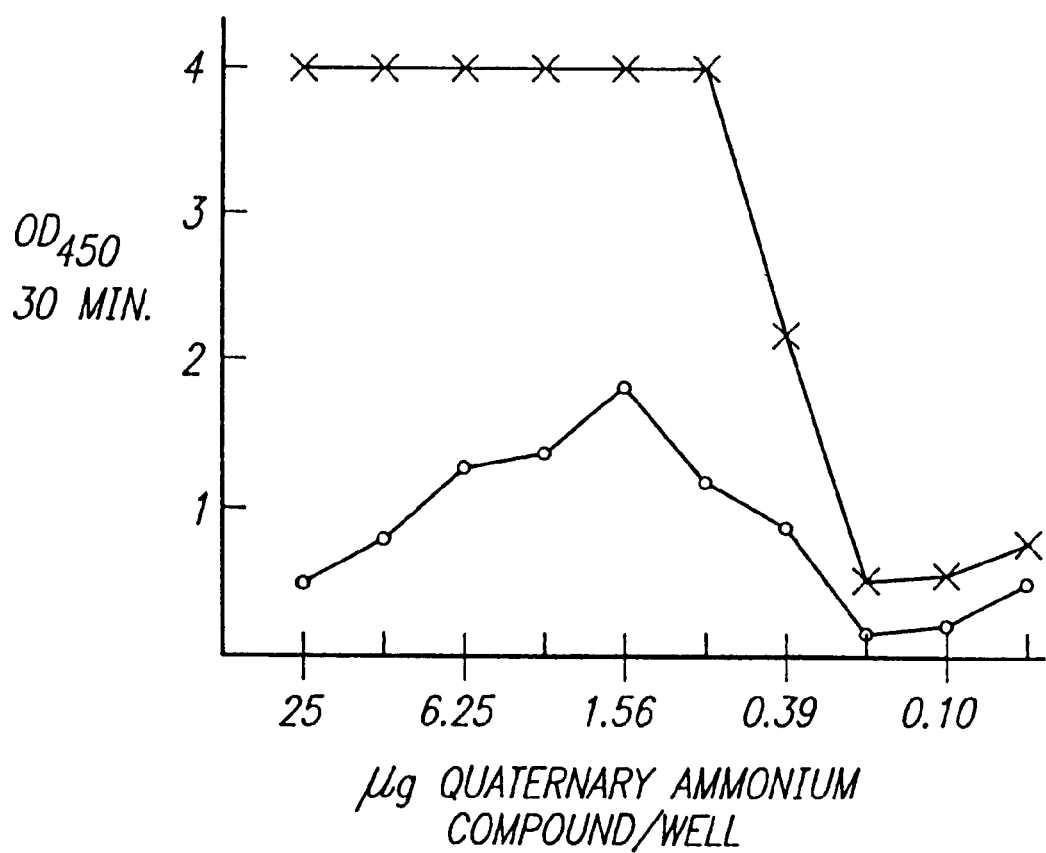
Figure 4A:
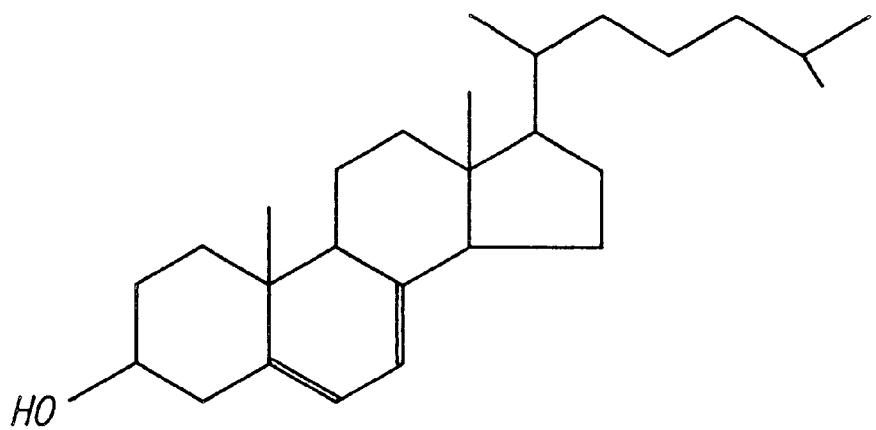
FIG. 4—Atherosclerotic plaque 15H5-antigen sizing. A mixture of the autoantigen and 4 size markers [Thyroglobulin (a); IgG (b); Ovalbumin (c); and Myoglobin (d)] were run through a BioSil analytical TSK-400 column. The auto-antigen was detected by binding with peroxidase-labeled 17H3 and 15H5. Binding is determined by measuring absorbance at $OD_{450}$.
Figure 4B:
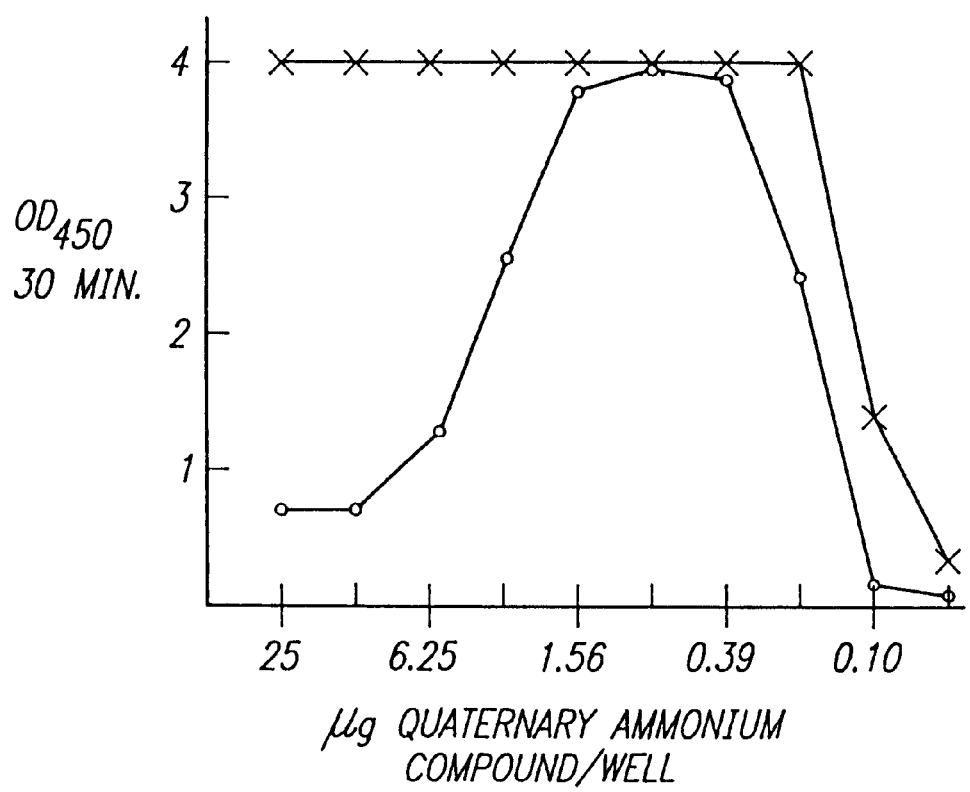

Initial studies of the atherosclerotic plaque antigen involved phosphate buffered saline (PBS) extraction of human atherosclerotic plaque. The extracts were then run through HPLC-DEAE fractionation procedures and fractions were tested to determine if they would react with serum from patients having coronary artery disease (CAD) (See FIG. 2). There existed a large amount of binding in the fractions which eluted just after the void volume. In the presence of normal serum (i.e. that obtained from patients under 35 years of age without CAD), there was no antigen-antibody binding.

The fractions which immediately followed the void volume of the column showed the highest levels of binding to CAD serum, and were used to immunize Balb C mice. Splenocytes from mice that produced antibodies were then fused with the immortal cell line SP2. One such fusion produced hybridoma 15H5.

The 15H5 monoclonal antibody was then covalently coupled to sepharose/agarose. This solid support antibody complex was then used in a number of assays to determine levels of antigen in various samples. Further, by contacting a PBS extraction of human atherosclerotic plaque with the 15H5 monoclonal antibody-solid support complex, it was possible to remove the auto-antigen from other extracted materials. The resulting complex was then washed and purified auto-antigen was then eluted from the complex.

TABLE 1

| | Characteristic | Plaque Extracted | Serum Extracted |
|---|---|---|---|
| 1. | Reacts with coronary artery patient serum | + | + |
| 2. | Reacts with 15H5 Ab | + | + |
| | Reacts with 17H3 Ab | + | + |
| | Reacts with Z2D3 Ab | – | – |
| | Reacts with Q10E7 Ab | – | – |
| 3. | Immunoreactivity following boiling for 1 hr. | + | + |
| 4. | Solubility in trichloroacetic acid | + | + |
| 5. | Immunoreactivity after trichloroacetic acid | + | + |
| 6. | Immunoreactivity after TFA | + | + |
| 7. | Immunoreactivity after TFA and heat | – | – |
| 8. | Molecular weight estimate by gel sieve chromatography | >500,000 mw | >500,000 mw |
| 9. | Molecular charge by ion exchange chromatography, ion exchange gels: | | |
| | DEAE SEPHAROSE ® QAE SEPHAROSE ® Sulfopropyl sepharoseneutralneutra | | |
| 10. | Glucosidase sensitive | +(limited) | +(limits$^d$) |
| 11. | Protease resistant | + | + |
| 12. | Acetone precipitable | yes | yes |
| 13. | Extractable with chloroform | no | no |
| 14. | Detectable primary amino groups | no | no |
| 15. | U.V. absorbance | none | none |
| 16. | Sensitive to chaotropes, SDS, or alkylation-reduction | no | no |
| 17. | Sensitive to periodate treatment | yes | yes |
| 18. | Sensitive to urea | no | no |

To further characterize the antigen, antibodies and antisera which specifically bind to the antigen were reacted with various components found in atherosclerotic plaque (see Table 2).

TABLE 2

| ANTI-SERA, MONOCLONAL ANTIBODY REACTIVITY WITH PURIFIED 15H5 ANTIGEN | |
|---|---|
| Antibody/Anti-Sera | Immuno-reactivity |
| Apolipoprotein A-I | – |
| Apolipoprotein A-II | – |
| Apolipoprotein B | – |
| Apolipoprotein C-III | – |
| Apolipoprotein E | – |
| Human collagen Type I | – |
| Human Collagen Type II | |
| Human Collagen Type III | |
| Human Collagen Type IV | – |
| Human Collagen Type V | – |
| Human Collagen Type VI | – |
| Fibronectin | |
| Keratin | – |
| Laminin | – |
| Tenascine | |
| Vitronectin | – |

As shown in Table 2, antibodies which bind specifically to the various components of atherosclerotic plaque do not bind to the 15H5 antigen showing that the antigen is not one of the components listed in Table 2.

To further characterize the antigen, the antigen was reacted with various enzymes to determine if the antigen is susceptible to degradation. It was found that proteinases, deoxyribonucleases, lipases, and ribonucleases did not degrade the 15H5 antigen. However, the 15H5 antigen was partially degraded by certain glycosidases, especially α-amylase, β-amylase, and glycoamylase. This suggests that the 15H5 antigen comprises a structure which has a carbohydrate nature. The results obtained with individual enzymes are shown in Table 3.

TABLE 3

ENZYME REACTIVITY WITH 15H5 PLAQUE ANTIGEN

| Enzyme | Reactivity |
|---|---|
| Proteinases | |
| Bromelain | − |
| Collagenase (Achromobater) | − |
| Collagenase/Dispase | − |
| Collagenase Type I | − |
| Collagenase Type II | − |
| Collagenase Type III | − |
| Chymotrypsin | − |
| Dispase | − |
| Elastase | − |
| Endoproteinase E | − |
| Endoproteinase Lys-C | − |
| Papain | − |
| Pepsin | − |
| Plasmin | − |
| Pronase | − |
| Proteinase K | − |
| Staphylococcal Protease V-8 | − |
| Thrombin | − |
| Trypsin | − |
| Glycosidases | |
| Chondroitinase ABC | − |
| Chondroitinase AC I | − |
| Chondroitinase AC II | − |
| Chondroitinase B | − |
| Heparinase | − |
| Heparinitase | − |
| Hyaluronidase | − |
| Keratanse | − |
| α-amylase | (±) |
| β-amylase | (±) |
| α-mannosidase | − |
| β-mannosidase | − |
| α-galactosidase | − |
| Endo-α-N-Acetylgalactosaminidase | − |
| Endo-β-galactosidase | − |
| α-fucosidase | − |
| β-glucoronidase | − |
| β-N-Acetyl-D-glucosaminidase | − |
| Endoglycosidase D | − |
| Endoglycosidase F | − |
| Endoglycosidase H | − |
| Glucoamylase | − |
| Invertase | − |
| Neuraminidase | − |
| Other | |
| Deoxyribonuclease | − |
| Lipase (Bacterial) | − |
| Lipase (Yeast) | − |
| ribonuclease | − |

Further characterization of the antigen was accomplished by measuring lectin binding to the auto-antigen. For example, *Conavalia ensiformis* and *Triticum Vulgaris* showed strong binding to the 15H5 antigen, whereas *Lens culinaris, Ricinus commonis*, and *Tetraaonolobus purpureai* showed moderate binding, and other lectins showed no binding. These results are summarized in Table 4.

TABLE 4

LECTIN BINDING PROFILE OF 15H5 ATHEROSCLEROSIS ANTIGEN

| Lectin | Plaque Extracted Antigen |
|---|---|
| *Arachis hypgaea* (Peanut) | − |
| *Bandeiraea simplicitolia* | − |
| *Conavalia ensiformis* (Con A) | +++ |
| *Dolichos biflorus* (Horse gram) | − |
| *Glycine max* (Soybean) | − |
| *Lens culinaris* (Lentil) | ++ |
| *Limulus polyphenus* (Limulin) | − |
| *Phaseolus vulgaris*-E (Phytohemaglutinin) | − |
| *Phaseolus vulgaris*-L (Phytohemaglutinin) | − |
| *Pisum sativum* (Pea) | − |
| *Ricinus commonis* (RCA I) | ++ |
| *Sophova japonica* (Pagoda Tree) | − |
| *Tetragonolobus purpureas* (Lotus) | ++ |
| *Triticum vulgaris* (Wheat germ) | +++ |
| *Ulex europaeus* (UEA-I) | − |
| *Ulex europaeus* (UEA-II) | − |
| *Vicia villosa* (Isolectin $B_4$) | − |

The antigen was also characterized by hydrolysis using 2M trifluoroacetic acid heated for 104° C. for 4 hrs followed by carbohydrate analysis. (Results are shown under Carbohydrate Analysis of Human Plasma Antigen in the Experimental Details Section).

Accordingly, the atherosclerotic plaque antigen may be characterized by the carbohydrate profile shown in FIGS. 20–22.

Figure 25:
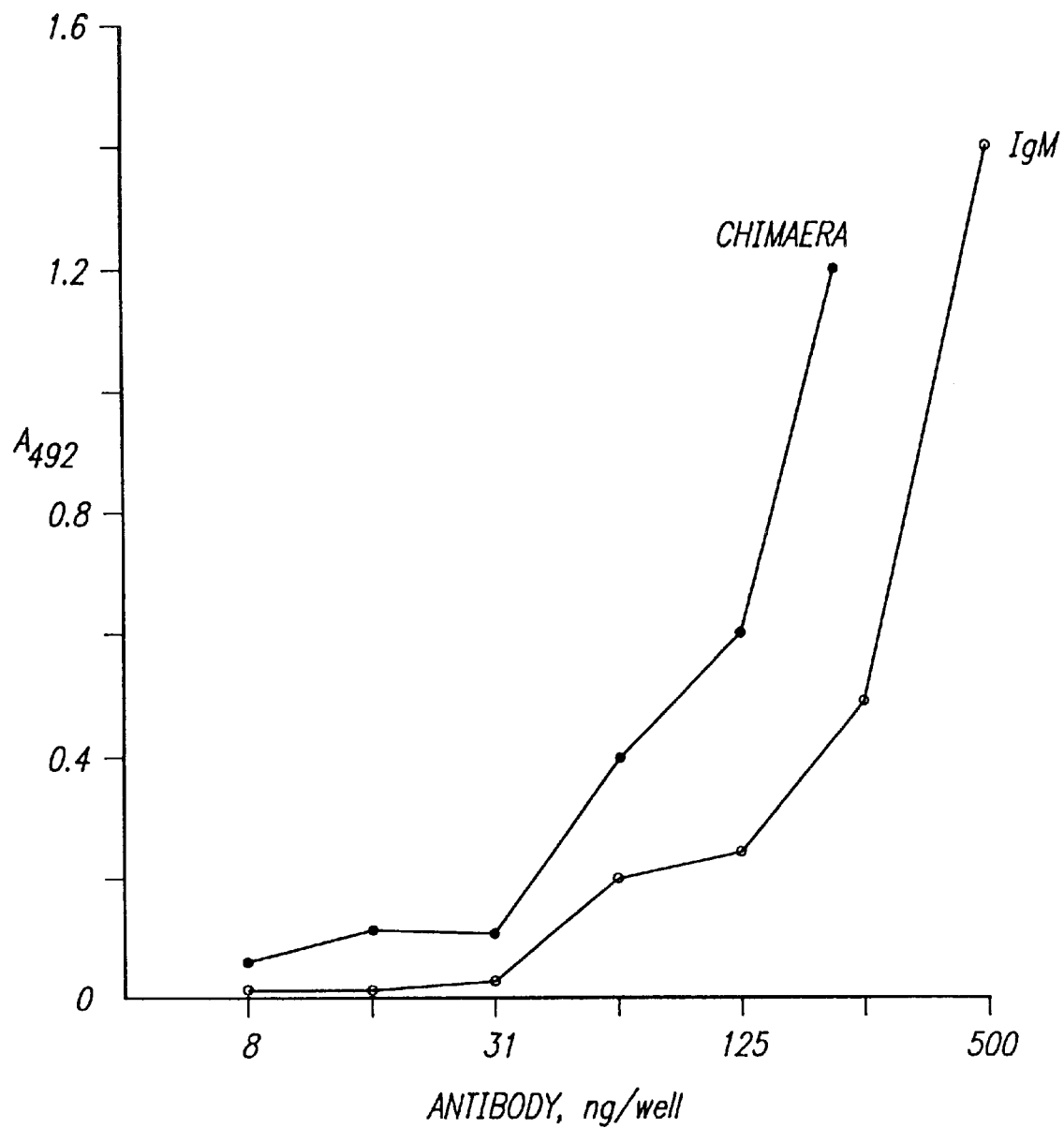
FIG. 25—Antigen binding inhibitions percent inhibition of binding for antibodies produced by hybridoma 15H5 and 17H3 shown after pretreatment of antigen covered microbes with various dilutions of CAD serum.
Figure 26A:
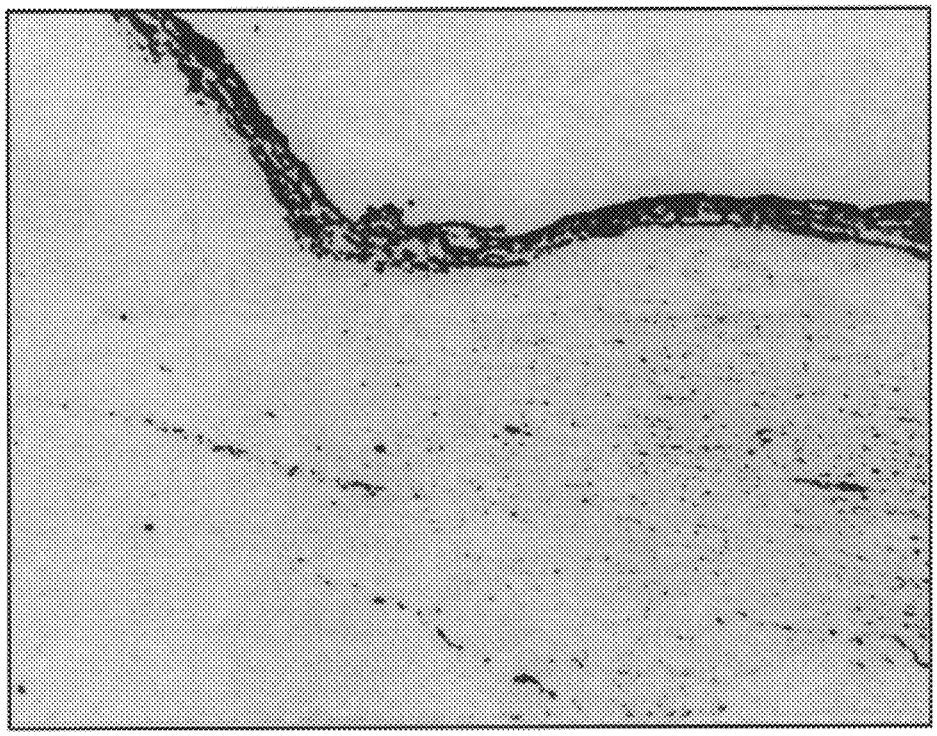
FIG. 26—Antigen binding inhibition percent inhibition of binding of CAD serum after pretreatment of antigen covered microwells with various amounts of the antibodies produced by hybridoma 15H5 and 17H3.
Figure 26B:
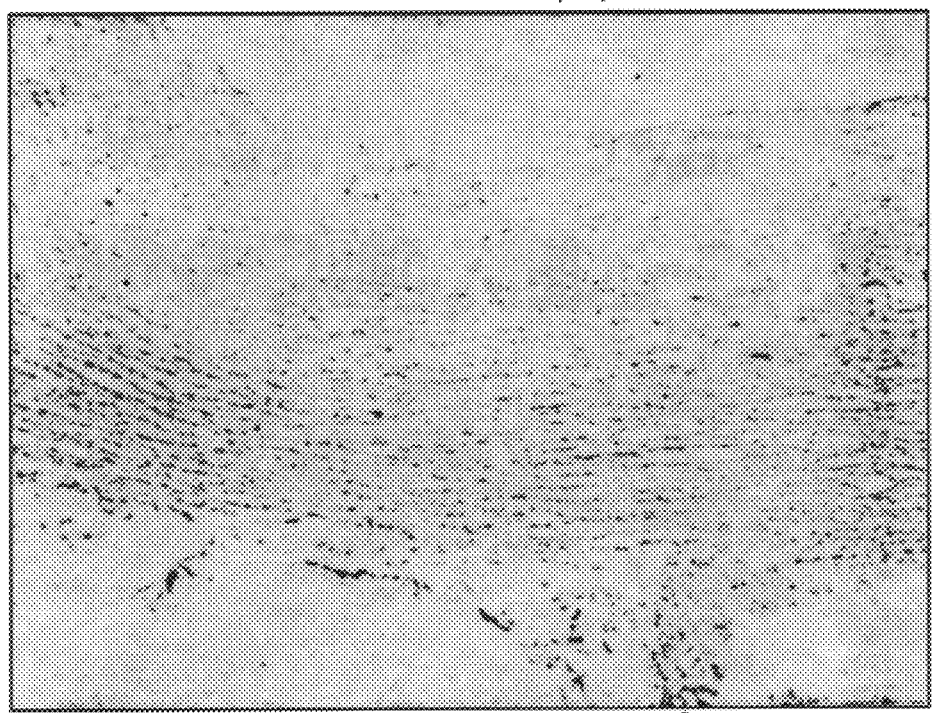
Figure 27A:
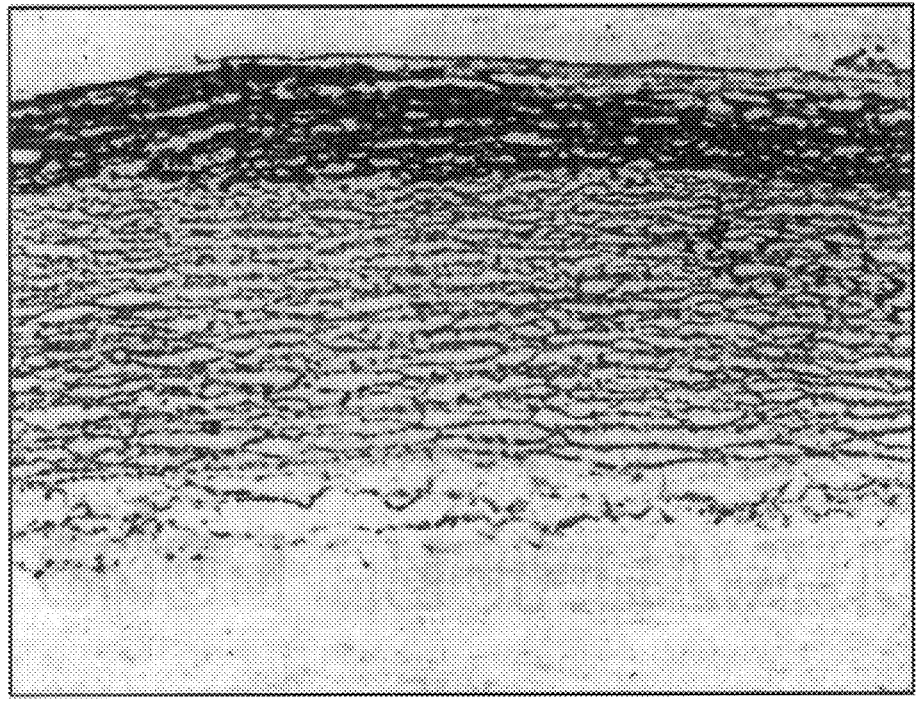
FIG. 27—Schematic representation of method No. 1 for purifying the forms of the atherosclerotic plaque antigen recognized by the antibodies produced by hybridomas Z2D3 and Q10E7.
Figure 27B:
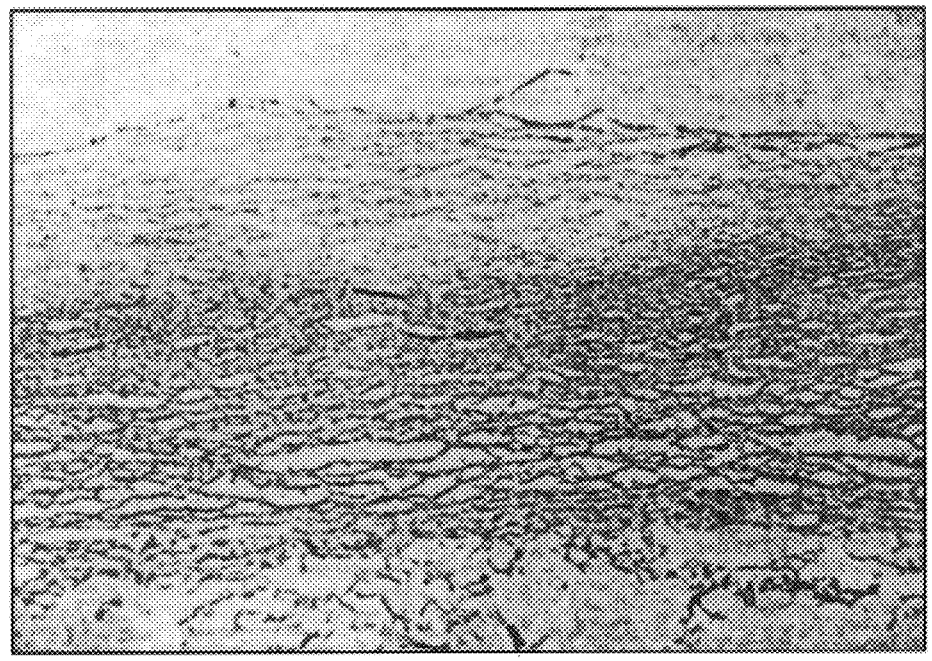
Figure 28A:
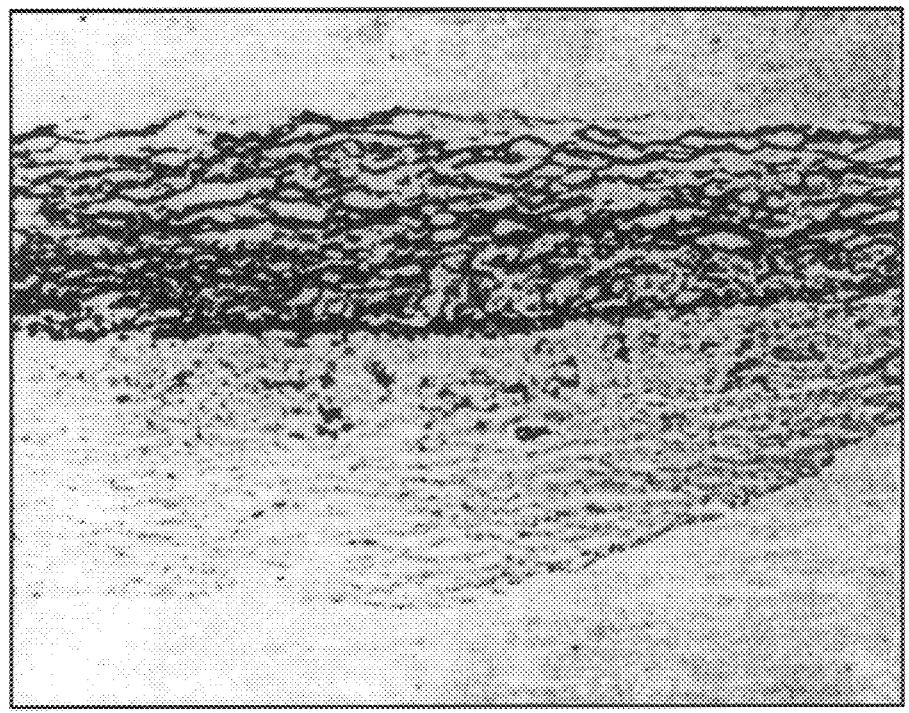
FIG. 28—DEAE ion exchange chromatography for CsCl fraction 1. The peak representing the antigen form which binds to Z2D3 is determined by the ELISA method using the antibody produced by hybridoma Z2D3.
Figure 28B:
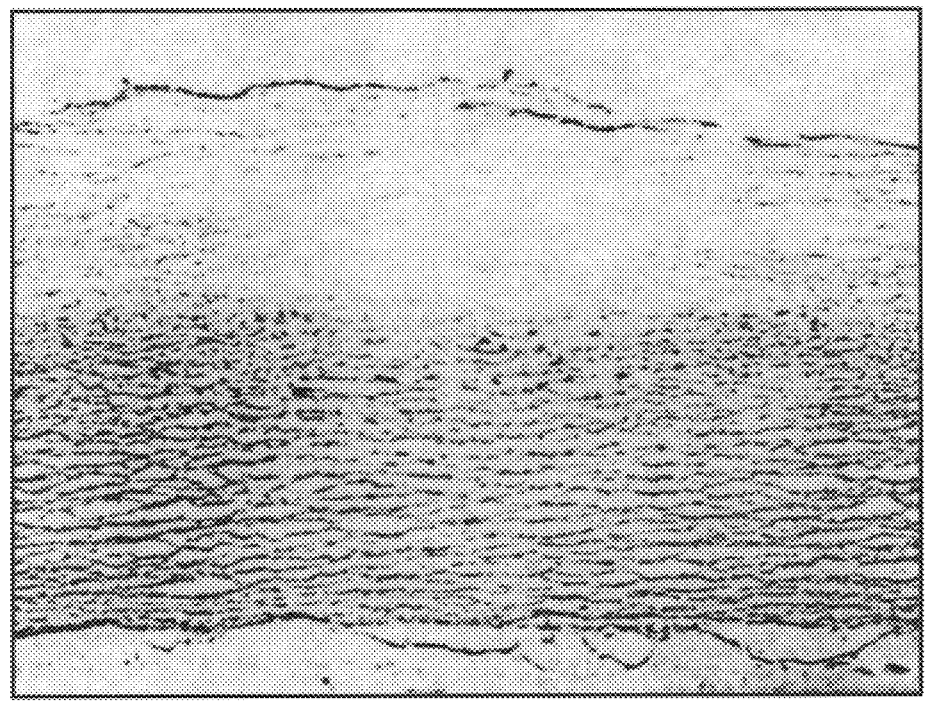
Figure 29:
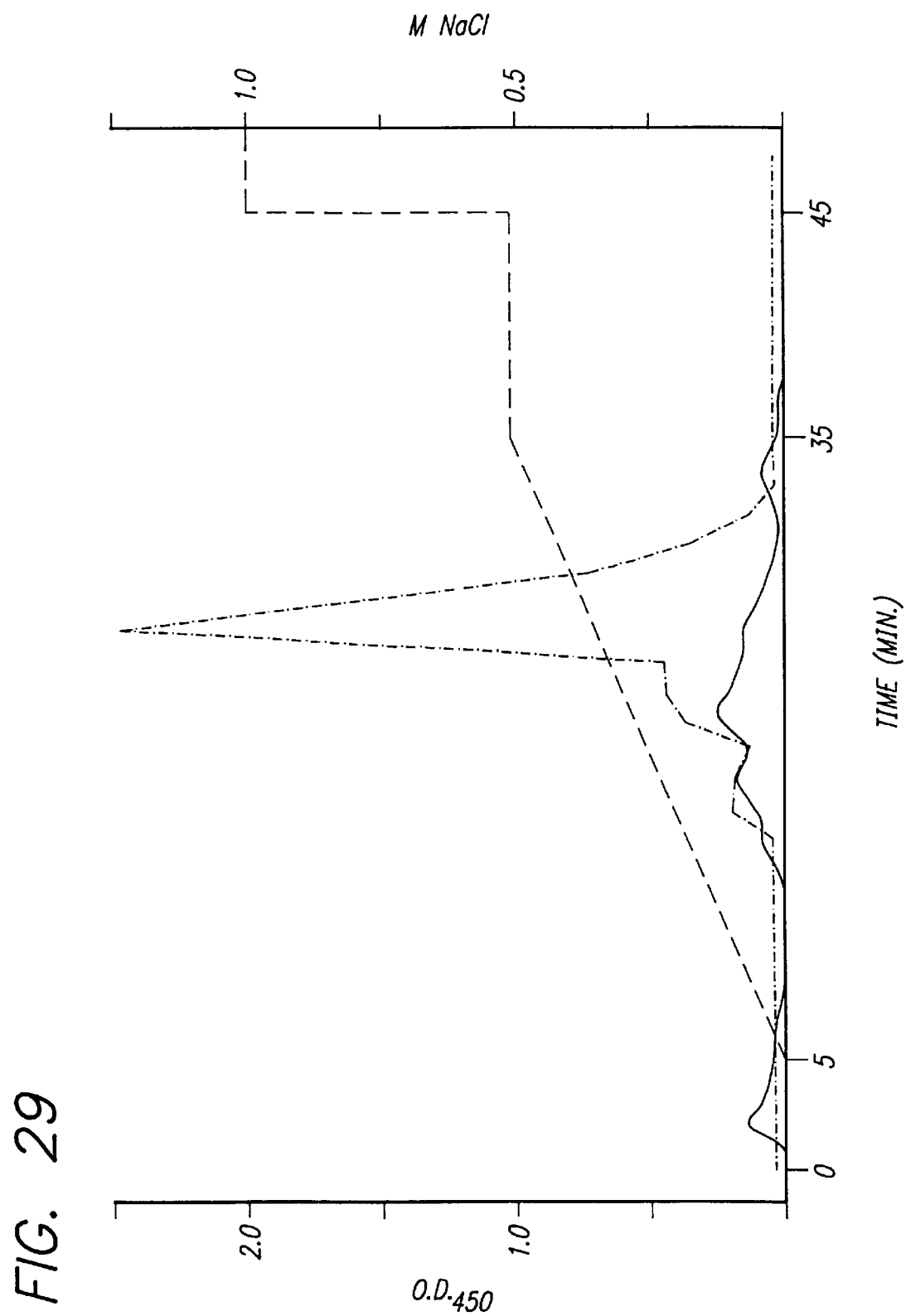
FIG. 29—DEAE ion exchange chromatography for CsCl fraction 4. The peak representing the antigen form which binds to Q10E7 is determined by the ELISA method using the antibody produced by hybridoma Q10E7.

The antibodies produced by hybridomas 15H5, Z2D3, Q10E7, and 17H3 were tested for binding to various tissues to determine if the antigens are plaque specific. The results of this testing, which was performed using the histological methods described in Procedures for Histology in the Experimental Detail section, are set forth in Table 5. Table 6 further characterizes the antibodies by cross reactivity and inhibition of antigens present in CAD serum. Actual inhibition assay results are depicted in FIG. 25. FIG. 26 shows the effect of binding inhibition using monoclonal antibodies instead of CAD serum.

TABLE 5

IMMUNOHISTOCHEMICAL SCREENING OF MONOCLONAL ANTIBODIES

| Tissue | 15H5 | Z2D3 | Q10E7 | 17H3 |
|---|---|---|---|---|
| Cerebellum | − | − | 2–3+* | − |
| Cerebral cortex | − | − | 2–3+* | − |
| Medulla | − | − | 1–2+* | − |
| Spinal cord | − | − | − | − |
| Dura | − | − | − | − |
| Peripheral nerve | − | − | − | − |
| Heat | − | − | − | − |
| Lung | − | − | − | − |
| Trachea | − | − | − | ± |
| Bronchus | − | − | − | ± |
| Breast | − | − | − | 1+ |
| Pectoral muscle | − | − | − | − |
| Esophagus | − | − | − | − |

TABLE 5-continued

IMMUNOHISTOCHEMICAL SCREENING OF MONOCLONAL ANTIBODIES

| Tissue | 15H5 | Z2D3 | Q10E7 | 17H3 |
|---|---|---|---|---|
| Diaphragm | − | − | − | − |
| Stomach | − | − | − | ± |
| Liver | − | − | − | − |
| Spleen | − | 3–4+*a | − | ± |
| Pancreas | − | − | − | ± |
| Small Bowel | − | − | − | − |
| Colon | − | − | − | − |
| Ovary | − | 1–2+*b | − | − |
| Uterus | − | − | − | − |
| Kidney | − | − | − | − |
| Bladder | − | − | − | ± |
| Rectum | − | − | − | ± |
| Psoas muscle | − | − | − | ± |
| Lymphnode | − | − | − | ± |
| Skin | − | 1–3+*c | − | − |
| Coronary artery lesions: | | | | |
| early lesions | − | ±–1+ | ± | − |
| advanced lesions | ± | 3–4+ | − | ±–1+ |
| Normal Arteries | − | − | 4+ | − |

*Intracellular staining only
aFibromyocytes only
bFocal luteal cells only
cSebaceous glands only

TABLE 6

MONOCLONAL ANTIBODY CHARACTERIZATION

| | 15H5 | Z2D3 | Q10E7 | 17H3 |
|---|---|---|---|---|
| Isotype | IgM | IgM | IgG$_1$ | IgM |
| pI | (5.2–5.9) | (5.0–5.7) | (5.1–5.8) | (4.5–5.1) |
| Auto-antigen reactivity | + | + | − | + |
| Z2D3 antigen reactivity | − | + | − | + |
| Q10E7 antigen reactivity | | | | |
| Inhibition of auto-antigen specific human antibodies | + | − | − | ± |
| Apparent binding constant | 10$^9$ | 10$^9$ | ? | 10$^{10}$ |

TABLE 7

IMMUNOHISTOCHEMICAL SCREENING OF Z2D3 MONOCLONAL ANTIBODY

| Tissue | Staining |
|---|---|
| Cerebellum | − |
| Cerebral cortex | − |
| Medulla | − |
| Spinal cord | − |
| Dura | − |
| Peripheral nerve | − |
| Heart | − |
| Lung | − |
| Trachea | − |
| Bronchus | − |
| Breast | − |
| Pectoral muscle | − |
| Esophagus | − |
| Diaphragm | − |
| Stomach | − |
| Liver | − |
| Spleen | +*a |
| Pancreas | − |
| Small bowel | − |
| Colon | − |
| Ovary | +*a |
| Uterus | − |
| Kidney | − |
| Bladder | − |
| Rectum | − |
| Psoas muscle | − |
| Lymph node | − |
| Skin | +*c |
| Coronary arteries: | |
| lesions | + |
| normal artery | − |
| Aorta: | |
| lesions | + |
| normal artery | − |

*Intracellular staining only
aFibromyocytes only
bFocal luteal cells only
cSebaceous glands only

What is claimed is:

1. A monoclonal antibody which specifically binds to an epitope of an antigen indicative of the presence of atherosclerotic plaque, to which epitope the monoclonal antibody produced by hybridoma Z2D3 (ATCC Accession No. HB 9840) or by hybridoma Z2D3/3E5 (ATCC Accession No. HB 10485) selectively binds.

2. The monoclonal antibody of claim 1 produced by hybridoma Z2D3 (ATCC Accession No. HB 9840) or by hybridoma Z2D3/3E5 (ATCC Accession No. HB 10485), or a fragment of said monoclonal antibody which specifically binds to the epitope to which said monoclonal antibody specifically binds.

3. A recombinant polypeptide which comprises an amino acid sequence which is substantially the same as the amino acid sequence of the hypervariable region of the monoclonal antibody of claim 2.

4. A chimeric antibody or an epitope-binding fragment thereof comprising the recombinant polypeptide of claim 3 or such polypeptide modified by site-directed mutagenesis.

5. The chimeric antibody of claim 4 or an epitope-binding fragment thereof comprising the amino acid sequences of a human framework region and of a constant region from a human antibody.

6. The monoclonal antibody of claim 2, bound to a solid support.

7. The recombinant polypetide of claim 3, bound to a solid support.

* * * * *